United States Patent
Wertz et al.

(10) Patent No.: US 12,053,471 B2
(45) Date of Patent: Aug. 6, 2024

(54) AMORPHOUS NILOTINIB MICROPARTICLES AND USES THEREOF

(71) Applicant: NANOCOPOEIA, LLC, New Brighton, MN (US)

(72) Inventors: Christian F. Wertz, Saint Louis Park, MN (US); Tzehaw Chen, Cocoran, MN (US); Joseph McTarsney, Shakopee, MN (US)

(73) Assignee: NANOCOPOEIA, LLC, New Brighton, MN (US)

( * ) Notice: Subject to any disclaimer, the term of this patent is extended or adjusted under 35 U.S.C. 154(b) by 0 days.

(21) Appl. No.: 18/094,050

(22) Filed: Jan. 6, 2023

(65) Prior Publication Data

US 2023/0181585 A1    Jun. 15, 2023

Related U.S. Application Data

(63) Continuation of application No. 17/866,939, filed on Jul. 18, 2022, which is a continuation of application No. 17/238,869, filed on Apr. 23, 2021, now Pat. No. 11,389,450, which is a continuation of application No. PCT/US2021/015864, filed on Jan. 29, 2021.

(60) Provisional application No. 62/968,749, filed on Jan. 31, 2020.

(51) Int. Cl.
| | | |
|---|---|---|
| *A61K 31/506* | (2006.01) | |
| *A61K 9/00* | (2006.01) | |
| *A61K 9/10* | (2006.01) | |
| *A61K 47/10* | (2017.01) | |
| *A61K 47/38* | (2006.01) | |

(52) U.S. Cl.
CPC .......... *A61K 31/506* (2013.01); *A61K 9/0053* (2013.01); *A61K 9/10* (2013.01); *A61K 47/10* (2013.01); *A61K 47/38* (2013.01)

(58) Field of Classification Search
CPC ........ A61K 31/506; A61K 9/10; A61K 47/38; A61P 35/02
See application file for complete search history.

(56) References Cited

U.S. PATENT DOCUMENTS

| | | |
|---|---|---|
| 5,178,878 A | 1/1993 | Wehling et al. |
| 5,464,632 A | 11/1995 | Cousin et al. |
| 5,648,093 A | 7/1997 | Gole et al. |
| 6,024,981 A | 2/2000 | Khankari et al. |
| 6,106,861 A | 8/2000 | Chauveau et al. |
| 6,221,392 B1 | 4/2001 | Khankari et al. |
| 6,316,029 B1 | 11/2001 | Jain et al. |
| 6,328,994 B1 | 12/2001 | Shimizu et al. |
| 6,350,786 B1 | 2/2002 | Albano et al. |
| 6,423,342 B1 | 7/2002 | Jordan et al. |
| 6,746,869 B2 | 6/2004 | Pui et al. |
| 6,764,720 B2 | 7/2004 | Pui et al. |
| 7,169,791 B2 | 1/2007 | Breitenstein et al. |
| 7,189,415 B2 | 3/2007 | Takagi et al. |
| 7,279,322 B2 | 10/2007 | Pui et al. |
| 7,431,942 B2 | 10/2008 | Shimizu et al. |
| 7,498,063 B2 | 3/2009 | Pui et al. |
| 7,569,566 B2 | 8/2009 | Breitenstein et al. |
| 7,875,292 B2 | 1/2011 | Shimizu et al. |
| 7,919,115 B2 | 4/2011 | Venkatesh et al. |
| 7,951,428 B2 | 5/2011 | Hoerr et al. |
| 7,972,661 B2 | 7/2011 | Pui et al. |
| 8,163,904 B2 | 4/2012 | Manley et al. |
| 8,293,756 B2 | 10/2012 | Bruneau |
| 8,389,537 B2 | 3/2013 | Manley et al. |
| 8,415,363 B2 | 4/2013 | Manley et al. |
| 8,501,760 B2 | 8/2013 | Bruneau |
| 8,518,446 B2 | 8/2013 | Ashraf et al. |
| 8,545,879 B2 | 10/2013 | Burns et al. |
| 8,557,995 B2 | 10/2013 | Miller et al. |
| 8,613,950 B2 | 12/2013 | Serno et al. |
| 8,703,196 B2 | 4/2014 | Babcock et al. |
| 8,840,925 B2 | 9/2014 | Venkatesh et al. |
| 8,841,303 B2 | 9/2014 | Breitenbach et al. |
| 8,883,209 B2 | 11/2014 | Babcock et al. |
| 8,940,800 B2 | 1/2015 | Babcock et al. |
| 8,974,827 B2 | 3/2015 | Bloom et al. |
| 8,992,471 B2 | 3/2015 | Dugas et al. |

(Continued)

FOREIGN PATENT DOCUMENTS

| | | |
|---|---|---|
| JP | 2020055838 | 4/2020 |
| WO | 2004005281 | 1/2004 |

(Continued)

OTHER PUBLICATIONS

Yin et al. (Cancer Chemother Pharmacol, 2012, 70(2), 345-350). (Year: 2012).*
Abdelbary et al., "Determination of the In Vitro Disintegration Profile of Rapidly Disintegrating Tablets and Correlation with Oral Disintegration," International Journal of Pharmaceutics 292 (2005) 29-41.
Ali et al., "Tackling the Challenges with Poorly Soluble Drugs," Journal of Analytical & Pharmaceutical Research, 2015: 1 (1) 1-3.
Bikiaris, Dimitrios, "Solid Dispersions, Part 1: Recent Evolutions and Future Opportunities in Manufacturing Methods for Dissolution Rate Enhancement of Poorly Water-Soluble Drugs," Expert Opin. Drug Deliv (2011) 8(11): 1501-1519.
Bikiaris, Dimitrios, "Solid Dispersions, Part II: New Strategies in Manufacturing Methods for Dissolution Rate Enhancement of Poorly Water-Soluble Drugs,", Expert Opin. Drug Deliv. (2011) 8(12).

(Continued)

*Primary Examiner* — Genevieve S Alley
(74) *Attorney, Agent, or Firm* — Mueting Raasch Group

(57) ABSTRACT

Amorphous solid dispersions and pharmaceutical compositions of the protein kinase inhibitor nilotinib. The pharmaceutical compositions may be used in methods of treating a proliferative disorder such as cancer. In some embodiments, the pharmaceutical compositions can be administered without regard to food consumption. In other embodiments, the pharmaceutical compositions can be administered at a significantly lower dose as compared to a commercially available immediate-release nilotinib formulation, while providing a comparable therapeutic effect.

22 Claims, 7 Drawing Sheets

(56) References Cited

U.S. PATENT DOCUMENTS

| | | |
|---|---|---|
| 8,992,603 B2 | 3/2015 | Dugas et al. |
| 9,040,816 B2 | 5/2015 | Gupta |
| 9,050,611 B2 | 6/2015 | Pui et al. |
| 9,061,029 B2 | 6/2015 | Gallagher et al. |
| 9,108,217 B2 | 8/2015 | Hoerr et al. |
| 9,211,261 B2 | 12/2015 | Appel et al. |
| 9,241,910 B2 | 1/2016 | Kurasawa et al. |
| 9,248,217 B2 | 2/2016 | Hoerr et al. |
| 9,301,957 B2 | 4/2016 | Bhardwaj et al. |
| 9,339,504 B2 | 5/2016 | Venkatesh et al. |
| 9,456,992 B2 | 10/2016 | Brisander et al. |
| 9,642,694 B2 | 5/2017 | Hoerr et al. |
| 9,827,230 B2 | 11/2017 | Brisander et al. |
| 9,833,442 B2 | 12/2017 | Brisander et al. |
| 9,833,443 B2 | 12/2017 | Brisander et al. |
| 10,034,882 B2 | 7/2018 | Gupta et al. |
| 10,076,494 B2 | 9/2018 | Pevzner et al. |
| 10,143,683 B2 | 12/2018 | Brisander et al. |
| 10,166,183 B2 | 1/2019 | Sommer et al. |
| 10,195,150 B2 | 2/2019 | Djordjevic et al. |
| 10,252,289 B2 | 4/2019 | Hoerr et al. |
| 10,265,301 B2 | 4/2019 | Miller et al. |
| 10,314,829 B2 | 6/2019 | Brisander et al. |
| 10,314,830 B2 | 6/2019 | Brisander et al. |
| 10,426,732 B2 | 10/2019 | Hashikawa et al. |
| 10,555,937 B2 | 2/2020 | Brisander et al. |
| 10,561,643 B2 | 2/2020 | Brisander et al. |
| 10,561,644 B2 | 2/2020 | Brisander et al. |
| 10,561,645 B2 | 2/2020 | Brisander et al. |
| 10,562,048 B2 | 2/2020 | Chen et al. |
| 10,772,877 B2 | 9/2020 | Brisander et al. |
| 10,821,375 B2 | 11/2020 | Fonseca et al. |
| 10,925,829 B2 | 2/2021 | Liu |
| 11,389,450 B2 | 7/2022 | Wertz et al. |
| 2005/0112196 A1 | 5/2005 | Xie et al. |
| 2009/0203709 A1 | 8/2009 | Steinberg et al. |
| 2010/0143459 A1 | 6/2010 | Liepold et al. |
| 2010/0266692 A1 | 10/2010 | Bloom et al. |
| 2011/0111018 A1 | 5/2011 | Ashraf et al. |
| 2011/0229627 A1 | 9/2011 | Hoerr et al. |
| 2011/0238163 A1 | 9/2011 | Andrews et al. |
| 2013/0096116 A1 | 4/2013 | Dalziel et al. |
| 2013/0274342 A1 | 10/2013 | Ginski et al. |
| 2013/0323403 A1 | 12/2013 | Hoerr et al. |
| 2014/0212487 A1 | 7/2014 | Mogalian et al. |
| 2015/0110871 A1 | 4/2015 | Wong |
| 2015/0190253 A1 | 7/2015 | Dugas et al. |
| 2015/0273070 A1 | 10/2015 | Li et al. |
| 2016/0120809 A1 | 5/2016 | Djordjevic et al. |
| 2016/0175881 A1 | 6/2016 | Lasch et al. |
| 2016/0235677 A1 | 8/2016 | Hoerr et al. |
| 2016/0346198 A1 | 12/2016 | Marota et al. |
| 2017/0209372 A1 | 7/2017 | Temtem et al. |
| 2019/0193109 A1 | 6/2019 | Hoerr et al. |
| 2019/0270735 A1 | 9/2019 | Rao et al. |
| 2020/0113903 A1 | 4/2020 | Liu et al. |
| 2020/0179963 A1 | 6/2020 | Chen et al. |
| 2020/0188400 A1 | 6/2020 | Liu et al. |
| 2020/0261426 A1 | 8/2020 | Park et al. |
| 2020/0261449 A1 | 8/2020 | Jain et al. |
| 2021/0353534 A1 | 11/2021 | Wertz et al. |
| 2022/0362246 A1 | 11/2022 | Wertz et al. |
| 2022/0378788 A1 | 12/2022 | Wertz et al. |

FOREIGN PATENT DOCUMENTS

| | | |
|---|---|---|
| WO | 2007015870 | 2/2007 |
| WO | 2007015871 | 2/2007 |
| WO | 2008037716 | 4/2008 |
| WO | 2010081443 | 7/2010 |
| WO | 2011062927 | 5/2011 |
| WO | 2012035074 | 3/2012 |
| WO | 2012164578 | 12/2012 |
| WO | 2013/105894 | 7/2013 |
| WO | 2013105894 | 7/2013 |
| WO | 2015181573 | 12/2015 |
| WO | 2016/016665 | 2/2016 |
| WO | 2016016665 | 2/2016 |
| WO | 2016/086193 | 6/2016 |
| WO | 2016097011 | 6/2016 |
| WO | 2017064538 | 4/2017 |
| WO | 2017108605 | 6/2017 |
| WO | 2020172120 | 8/2020 |

OTHER PUBLICATIONS

Budha et al., "Drug Absorption Interactions Between Oral Targeted Anticancer Agents and PPIs: Is PH-Dependent Solubility the Achilles Heel of Targeted Therapy?", Clinical Pharmacology & Therapeutics, vol. 92, No. 2, Aug. 2012, pp. 203-213.

Chaudhari, et al., "Evaluating the Effects of Different Molecular Weights of Polymers in Stabilizing Supersaturated Drug Solutions and Formulations Using Various Methodologies of the Model Drug: Fenofibrate," Journal of Pharmaceutical Sciences and Pharmacology, vol. 2, 259-276, 2015.

Cheng et al., "Food Effects on Oral Drug-Absorption: Application of Physiologically-Based Pharmacokinetic Modeling as a Predictive Tool", Pharmaceutics, 2020, 12, 672, 18 pages.

Chu et al., "Gastric Acid Suppression is Associated with Decreased Erlotinib Efficacy in Non-Small-Cell Lung Cancer", Clinical Lung Cancer, vol. 16, No. 1, pp. 33-39 (2015).

Cilurzo et al., "Orodispersible Dosage Forms: Biopharmaceutical Improvements and Regulatory Requirements," Drug Delivery Today, vol. 23, No. 2, Feb. 2018, pp. 251-259.

Colombo et al., "Matrix Effects in Nilotinib Formulations with pH-Responsive Polymer Produced by Carbon Dioxide-Mediated Preciptation," International Journal of Pharmaceutics, 494 (2015) 2015-217.

Gala et al., "Harnessing the Therapeutic Potential of Anticancer Drugs Through Amorphous Solid Dispersions", BB—Reviews on Cancer 1873 (2020) 188319.

Guidance for Industry, Orally Disintegrating Tablets, U.S. Department of Health and Human Services, Food and Drug Administration, Dec. 2008 (6 pages).

Gurunath et al., "Amorphous Solid Dispersion Method for Improving Oral Bioavailability of Poorly Water-Soluble Drugs", Journal of Pharmacy Research 6 (2013) 476-480.

Ha et al., "Does Gastric Acid Suppression Affect Sunitinib Efficacy in Patients with Advanced or Metastatic Renal Cell Cancer?", J Oncol Pharm Practice,, 2015, vol. 21(3), 194-200.

Haouala et al., "Drug Interactions with the Tyrosine Kinase Inhibitors Imatinib, Dasatinib, and Nilotinib", Blood, Feb. 24, 2011, vol. 117, No. 8.

Herbrink et al., Accepted Manuscript: Improving the Solubility of Nilotinib Through Novel Spray-Dried Solid Dispersions, 2017, 28 pages.

Herbrink, et al., "Inherent Formulation Issues of Kinase Inhibitors", Journal of Controlled Release, 239 (2016) 118-127.

Herbrink, Maikel, Thesis of Pharmaceutics of Oral Anticancer Agents and Stimulants, Feb. 2, 1990, pp. 1-315.

Hoshino-Yoshino et al., "Bridging from Preclinical to Clinical Studies for Tyrosine Kinase Inhibitors Based on Pharmacokinetics/Pharmacodynamics and Toxicokinetics/Toxicdynamics", Drug Metab. Pharmacokinet. 26(6): 612-620 (2011).

https://biorelevant.com/fassif-fessif-fassgf/buy/ (4 pages).

Huang et al., "Fundamental Aspects of Solid Dispersion Technology for Poorly Soluble Drugs", Acta Pharmaceutica Sinica B 2014; 4(1):18-25.

Hughey et al., "The Use of Inorganic Salts to Improve the Dissolution Characteristics of Tablets Containing Soluplus-Based Solid Dispersions," European Journal of Pharma Sciences, 48 (2013) 758-766.

Tevbare et al., "Liquid-Liquid Phase Separation in Highly Supersaturated Aqueous Solutions of Poorly Water-Soluble Drugs: Implications for Solubility Enhancing Formulations,", Cryst. Growth Des. 2013, 13, 1497-1509.

Indian Patent Application No. 201941006393 filed Feb. 18, 2019 for "Pharmaceutical Compositions of Nilotinib", 48 pages.

(56) References Cited

OTHER PUBLICATIONS

Jesson et al., "Carbon Dioxide-Mediated Generation of Hybrid Nanoparticles for Improved Bioavailability of Protein Kinase Inhibitors", Pharm Res (2014) 31:694-705.
Karagianni et al., "Co-Amorphous Solid Dispersions for Solubility and Absorption Improvement of Drugs: Composition, Preparation, Characterization and Formulations for Oral Delivery", Pharmaceutics 2018, 10, 98.
Klancke et al., "Application of a Modified Disk for Testing Orally Disintegrating Tablets by USP <701>," Dissolution Technologies, May 2018, pp. 10-13.
Mitra et al., "Impaired Drug Absorption Due to High Stomach pH: A Review of Strategies for Mitigation of Such Effect to Enable Pharmaceutical Product Development", Molecular Pharmaceutics, 2013, 10, 3970-3979.
Nguyen et al., "Pharmaceutical Applications of Electrospraying", Journal of Pharmaceutical Sciences 105 (2016) 2601-2620.
Nikghalb et al., "Solid Dispersion: Methods and Polymers to Increase the Solubility of Poorly Soluble Drugs," Journal of Applied Pharma Science, vol. 2 (10), pp. 170-175, Oct. 2012.
Nilausen et al., "The Perception and Pharmacokinetics of a 20-mg Dose of Escitalopram Orodispersible Tablets in a Relative Bioavailability Study in Healthy Men," Clinical Therapeutics, vol. 33, No. 10, 2011 (pp. 1493-1502).
Non Final Office Action dated Sep. 10, 2021 for U.S. Appl. No. 17/328,548, (38 pages).
Non Final Office Action issued Aug. 20, 2021 for U.S. Appl. No. 17/238,869, (31 pages).
O'Shea et al., "Food for Thought: Formulating Away the Food Effect-A PEARRL Review", Journal of Pharmacy and Pharmacology, 71 (2019), pp. 510-535.
PCT International Search Report and Written Opinion for PCT/US2021/015864 dated May 7, 2021 (15 pages).
PCT Search Report and Written Opinion for PCT/US2021/015864 dated May 7, 2021 (11 pages).
PCT Search Report and Written Opinion for PCT/US2021/030154 dated Aug. 17, 2021 (14 pages).
Purohit et al., "Phase Separation Kinetics in Amorphous Solid Dispersions Upon Exposure of Water," Mol. Pharmaceutics 2015, 12, 1623-1635.
Raina et al., "Enhancements and Limits in Drug Membrane Transport Using Supersaturated Solutions of Poorly Water Soluble Drugs," Journal of Pharmaceutical Sciences, 103:2736-2748, 2014.
Raina et al., "Impact of Polymers on the Crystallization and Phase Transition Kinetics of Amorphous Nifedipine During Dissolution in Aqueous Media,", Mol. Pharmaceutics 2014, 11, 3565-3576.
Ratain et al., "Importance of Food Effects for Oral Oncology Drugs," Clinical Advances in Hematology & Oncology, vol. 10, Issue 6, Jun. 2012. 397-398.
Sane et al., "Development and Evaluation of a Novel Microemulsion Formulation of Elacridar to Improve its Bioavailability," J Pharm Sci, Apr. 2013, 102(4): 1343-1354.
Segal et al., "Oral Chemotherapy Food and Drug Interactions: A Comprehensive Review of the Literature", Journal of Oncology Practice, vol. 10, Issue 4, 2014, pp. 255-268.
Smelick et al., "Prevalence of Acid-Reducing Agents (ARA) in Cancer Populations and ARA Drug-Drug Interaction Potential for Molecular Targeted Agents in Clinical Development", Mol. Pharmaceutics 2013, 10, 4055-4062.
Sridhar et al., "Electrosprayed Nanoparticles for Drug Delivery and Pharmaceutical Applications", Biomatter 3:3, 24281, Jul./Aug./Sep. 2013.
Szakonyi et al., "Prediction of Oral Disintegration Time of Fast Disintegrating Tablets Using Texture Analyzer and Computational Optimization," International Journal of Pharmaceutics, 448 (2013) 346-353.
Tasigna-Nilotinib Capsule, Novartis Pharmaceuticals Corporation, Sep. 2019 (46 pages).
Taylor et al., "Physical Chemistry of Supersaturated Solutions and Implications for Oral Absorption," Advanced Drug Delivery Reviews 101 (2016) 122-142.
Tran et al., "Overview of the Manufacturing Methods of Solid Dispersion Technology for Improving the Solubility of Poorly Water-Soluble Drugs and Application to Anticancer Drugs", Pharmaceutics 2019, 11, 132.
U.S. Appl. No. 17/206,823, filed Mar. 19, 2021.
U.S. Appl. No. 17/328,548, filed May 24, 2021, Orally Disintegrating Tablet Comprising Amorphous Solid Dispersion of Nilotinib.
Van Leeuwen et al., "Drug-Drug Interactions with Tyrosine-Kinase Inhibitors: A Clinical Perspective", Review, www.thelancet.com/oncology, vol. 15, Jul. 2014 e315-326.
Wegiel et al., "Crystallization of Amorphous Solid Dispersions of Resveratrol During Preparation and Storage-Impact of Different Polymers," Journal of Pharmaceutical Sciences, vol. 102, No. 1, Jan. 2013.
Willemsen et al., "Effect of Food and Acid-Reducing Agents on the Absorption of Oral Targeted Therapies in Solid Tumors", Drug Discovery Today, vol. 21, No. 6, Jun. 2016, 962-976.
Xia et al., "Nilotinib Preclinical Pharmacokinetics and Practical Application Toward Clinical Projections of Oral Absorption and Systemic Availability," Biopharm. Drug Dispos. 33: 536-549 (2012).
XSpray Announces Positive Phase I Data for HyNap Nilotinib, Stockholm, May 8, 2014, Karolinska Development, 2 pages.
Yago et al., "Gastric Re-Acidification with Betaine HCI in Healthy Volunteers with Rabeprazole—Induced Hypochlorhydria", Mol. Pharm., Nov. 4, 2013.
Yago et al., "The Use of Betaine HCI to Enhance Dasatinib Absorption in Healthy Volunteers with Rabeprazole—Induced Hypochlorhydria", The AAPS Journal, vol. 16, No. 6, Nov. 2014, 1358-1365.
Yin et al., "Effects of Yogurt and Applesauce on the Oral Bioavailability of Nilotinib in Healthy Volunteers," J Clin Pharmacol 2011; 51: 1580-1586.
Zhang et al., "pH-Dependent Drug-Drug Interactions for Weak Base Drugs: Potential Implications for New Drug Development", Nature, vol. 96, No. 2, Aug. 2014, 266-277.
Zhang et al., "Processing Impact on Performance of Solid Dispersions", Pharmaceutics 2018, 10, 142.

\* cited by examiner

AMORPHOUS NILOTINIB MICROPARTICLES AND USES THEREOF

REFERENCE TO RELATED APPLICATION

The present application is a continuation of U.S. application Ser. No. 17/866,939, filed Jul. 18, 2022, which is a continuation application of U.S. application Ser. No. 17/238,869, filed Apr. 23, 2021, now issued U.S. Pat. No. 11,389,450, which is a continuation application of International Application No. PCT/US2021/015864, filed Jan. 29, 2021, which claims the benefit of U.S. Provisional App. No. 62/968,749 (filed Jan. 31, 2020), the entire disclosures of which are hereby incorporated by reference.

BACKGROUND

Protein kinase inhibitors (PKIs) have been studied for their potential use in treating various disorders of cellular proliferation, including cancer. The potential for PKIs as a treatment is based on the role that protein kinases are known to play in regulating many cellular pathways, including those involved in signal transduction. Dysregulation of protein kinases has been implicated in the development and progression of many cancers, which suggests that PKIs may be useful as a treatment for disorders or diseases such as cancer that are caused by uncontrolled overexpression or upregulation of protein kinases.

One such PKI is nilotinib, which is currently marketed as an immediate-release formulation for oral administration under the brand name TASIGNA. TASIGNA is indicated for (a) treatment of adult and pediatric patients greater than or equal to 1 year of age with newly diagnosed Philadelphia chromosome positive chronic myeloid leukemia (Ph+ CML) in chronic phase; (b) treatment of adult patients with chronic phase and accelerated phase Ph+ CML resistant or intolerant to prior therapy that included imatinib; and (c) treatment of pediatric patients greater than or equal to 1 year of age with chronic phase Ph+ CML with resistance or intolerance to prior tyrosine-kinase inhibitor therapy.

Presently, oral dosage of TASIGNA is accompanied by a food effect. In fact, the prescribing information for TASIGNA contains a boxed warning that includes the statement, "[a]void food 2 hours before and 1 hour after taking the dose." According to the prescribing information, "[s]ignificant prolongation of the QT interval may occur when TASIGNA is inappropriately taken with food and/or strong CYP3A4 inhibitors and/or medicinal products with a known potential to prolong QT. Therefore, co-administration with food must be avoided . . . ." This effect on the QT interval is likely due to the increase in exposure (expressed as area-under-the-curve, or AUC) and/or maximum plasma concentration ($C_{max}$) that can occur when TASIGNA is taken with food. For example, a single 400-mg dose of TASIGNA taken 30 minutes after a high-fat meal, increased AUC and $C_{max}$ by 82% and 112%, respectively, as compared to levels obtained under fasting conditions. Such an increase in serum levels may also exacerbate or increase the prevalence of common side effects such as nausea, diarrhea, rash, headache, muscle and joint pain, tiredness, vomiting, and fever; as well as more serious side effects such as low blood cell counts, decreased blood flow to the heart or brain, pancreas inflammation, liver problems, and bleeding problems.

The current prescribing information for TASIGNA instructs the patient to dose TASIGNA twice daily on an empty stomach, and avoid food 2 hours before and 1 hour after taking a dose. The requirement to take TASIGNA twice-α-day without food (for a three-hour period for each dose) is a considerable burden to patients. Further, in light of the side effects that can occur with TASIGNA, poor adherence to the dosing recommendations can be very detrimental to patients.

In addition, the solubility of nilotinib significantly decreases with increasing pH, and therefore nilotinib absorption may be compromised if TASIGNA is administered along with gastric acid-reducing agents. Use of TASIGNA with common gastric acid-reducing agents is restricted in accordance with prescribing information. For example, the prescribing information for TASIGNA states, "[a]void concomitant use of [proton pump inhibitor] with Tasigna." The prescribing information further suggests to "[u]se short-acting antacids or H2 blockers as an alternative to proton pump inhibitors" because "[c]oncomitant use with a [proton pump inhibitor] decreased nilotinib concentrations compared to Tasigna alone . . . which may reduce Tasigna efficacy." For safe use of TASIGNA with gastric acid-reducing agents, the following instruction is provided in the prescribing information: "As an alternative to PPIs, use H2 blockers approximately 10 hours before or approximately 2 hours after the dose of Tasigna, or use antacids approximately 2 hours before or approximately 2 hours after the dose of Tasigna." These restrictions on how patients can address indigestion or excess gastric acidity while treated with TASIGNA are burdensome, especially in light of how often such symptoms can occur within the patient population. Moreover, poor adherence to the prescribing information's warnings about taking gastric acid-reducing agents while being treated with TASIGNA can be detrimental to the patient.

Thus, there remains a need in the art for a means for patients to receive the full benefits of nilotinib while minimizing the risk of experiencing adverse side effects, especially those that are associated with TASIGNA's food effect, as well as for a nilotinib treatment that does not require such restricted co-administration of nilotinib with a gastric acid-reducing agent.

SUMMARY OF DISCLOSURE

An aspect of the disclosure relates to an amorphous solid dispersion ("ASD") comprising nilotinib. The ASD comprises nilotinib and one or more polymers. In some embodiments, the ASD comprises nilotinib and one or more polymers that exhibits pH-dependent solubility.

In another aspect, the disclosure provides pharmaceutical compositions comprising the ASDs.

Yet another aspect of the disclosure relates to a method of treating a disease which responds to an inhibition of protein kinase activity, such as a proliferative disorder. In some embodiments, the method comprises administration of an ASD or pharmaceutical composition of the present disclosure to a patient. In some embodiments, the composition is administered without regard to consumption of food. In some embodiments, the composition is administered without regard to whether the patient is in a fasted state or a fed state.

In another embodiment, the disclosure provides a method of safely delivering nilotinib to a patient in need thereof, the method comprising: (a) administering to the patient a therapeutically effective amount of a pharmaceutical composition of the disclosure; and (b) administering a meal to the patient; wherein steps (a) and (b) occur within less than two hours of each other.

In other embodiments, the disclosure provides kits for sale to a user. The kits comprise a pharmaceutical composition according to the disclosure, and a package insert. In one embodiment, the package insert informs the user that the pharmaceutical composition can be administered with food. In another embodiment, the package insert informs the user that the pharmaceutical composition can be administered with or without food. In another embodiment, the package insert does not include a warning that the pharmaceutical composition should not be administered with food.

DETAILED DESCRIPTION

Figure 1:
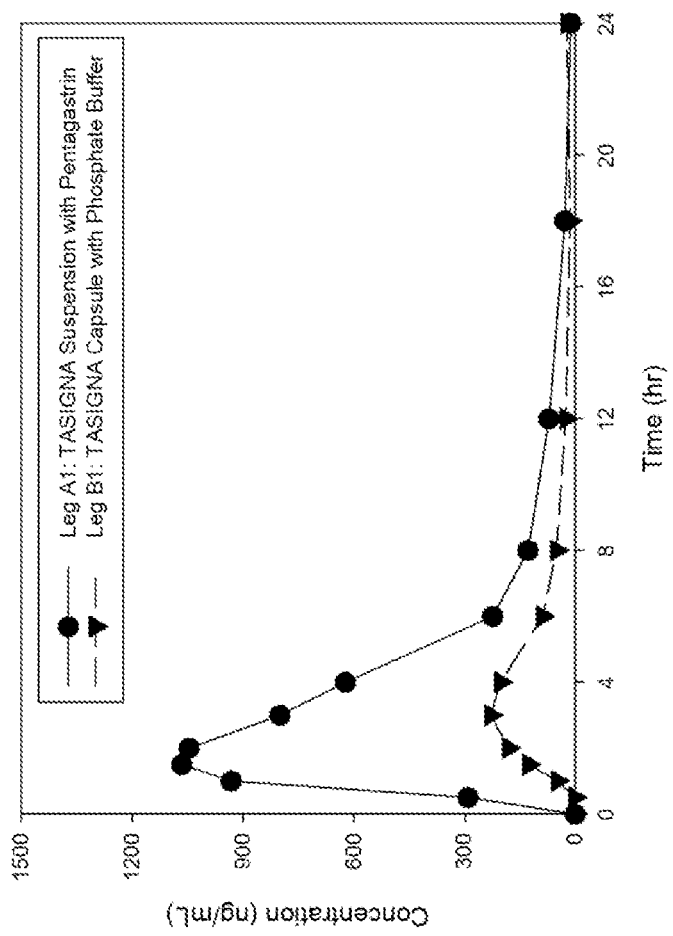
FIG. 1 shows pharmacokinetic profiles for (a) male beagles in a fasted state administered TASIGNA Suspension after pretreatment with pentagastrin (pH 1-2) (Leg A1); or (b) male beagles in a fasted state administered TASIGNA Capsule after pretreatment with phosphate buffer (pH ~2.5) (Leg B1); as described in Example 4.

The present disclosure relates to nilotinib ASDs, pharmaceutical compositions of nilotinib ASDs, and methods of use comprising administration of nilotinib ASDs or the pharmaceutical compositions. The nilotinib ASDs and the pharmaceutical compositions of the present disclosure may provide particular advantages over conventional immediate-release crystalline nilotinib formulations, such as TASIGNA. For instance, as described herein, the prescribing information for TASIGNA warns to avoid food 2 hours before and 1 hour after taking a dose. In contrast, certain ASDs and pharmaceutical compositions of the present disclosure can be administered without regard to food consumption.

Moreover, certain ASDs and pharmaceutical compositions of the present disclosure unexpectedly provide a pharmacokinetic profile similar to that of TASIGNA, even when the dose of nilotinib administered by the pharmaceutical compositions is a fraction of the dose of nilotinib normally administered when using TASIGNA. Therefore, the disclosure provides pharmaceutical compositions that can be administered at a lower dose than TASIGNA, but that would be expected to provide a comparable therapeutic effect.

As another advantage, pharmaceutical compositions of the disclosure may achieve a reduced inter-subject and/or intra-subject variability, as compared to the variability observed for TASIGNA.

Thus, the ASDs and the pharmaceutical compositions of the present disclosure may offer a safer but equally effective presentation of nilotinib as compared to the currently available immediate-release product.

Nilotinib

Nilotinib is a kinase inhibitor having the following structure:

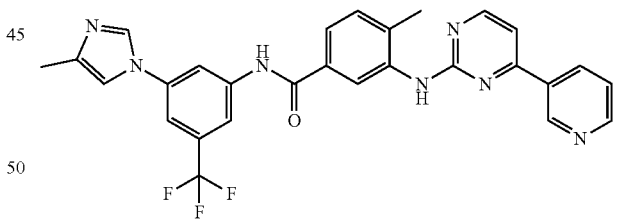

The chemical name for nilotinib is 4-methyl-N-[3-(4-methyl-1H-imidazol-1-yl)-5-(trifluoromethyl)phenyl]-3-[[4-(3-pyridinyl)-2-pyrimidinyl]amino]-benzamide. The molecular formula is $C_{28}H_{22}F_3N_7O$, which corresponds to a molecular weight of 529 g/mol (nilotinib base, anhydrous).

Nilotinib is marketed under the tradename TASIGNA, as an immediate-release formulation containing nilotinib monohydrochloride monohydrate. It is thought that the nilotinib monohydrochloride monohydrate in TASIGNA is in a crystalline form. Currently available TASIGNA capsules (marketed in the United States under New Drug Application 22-068) are labeled as containing 50 mg, 150 mg, or 200 mg nilotinib base, anhydrous (equivalent to 55 mg, 166 mg, and 221 mg nilotinib monohydrochloride monohydrate, respectively.) As used herein, "TASIGNA IR Capsule" refers to commercially available TASIGNA immediate-release capsules.

Nilotinib monohydrochloride monohydrate is characterized as a Class IV compound (low/moderate aqueous solubility and low permeability) according to the Biopharmaceutical Classification System ("BCS"). A preparation of nilotinib in a form that is intended to enhance its solubility could increase its bioavailability. One approach for enhancing solubility is to produce an amorphous solid dispersion.

Amorphous Solid Dispersions of Nilotinib

One aspect of the present disclosure relates to amorphous solid dispersions ("ASDs") comprising nilotinib and one or more polymers. A pharmaceutically suitable amorphous solid dispersion generally comprises a pharmaceutically active ingredient, such as nilotinib, dispersed in a pharmacologically inert carrier, such as a polymer. One aim of a pharmaceutically suitable amorphous solid dispersion is to improve the bioavailability of the pharmaceutically active ingredient. This improvement can occur, for example, because of enhanced surface area, improved wettability or dispersibility, increased dissolution rate, or other factors.

In general, it is favorable if the pharmaceutically active ingredient is dispersed in the polymer to form what has been termed in the art as a "glass solution." However, other forms of dispersion, such as those termed as "solid solution" or "glass suspension," may also be suitable. The precise characterization of the solid dispersion is not important, provided that the amorphous solid dispersion is capable of providing desired characteristics and performance.

In the ASDs of the disclosure, the nilotinib may be as a free base or as a salt such as a hydrochloride. In some embodiments, the nilotinib is as a free base and is anhydrous. Such forms of nilotinib and processes of preparing nilotinib are disclosed, for example, in WO 2004/005281 and WO 2007/015871. In the description of the amorphous solid dispersions and pharmaceutical compositions below, and in the claims, any reference to "nilotinib" refers broadly to nilotinib free base, salts of nilotinib, anhydrous nilotinib (or salts thereof), hydrates or solvates of nilotinib, and hydrates or solvates of nilotinib salts as suitable alternatives, unless specified.

The one or more polymers, which should be pharmacologically inert, should be suitable to provide structure and stability to the ASD. By "pharmacologically inert," it is meant that the material does not initiate a pharmacological response or an adverse reaction when introduced to a relevant biological system (such as the gastrointestinal tract).

In some embodiments, the ASD comprises nilotinib and one or more polymers. In certain embodiments, the ASD consists of nilotinib and the one or more polymers. In certain other embodiments, the ASD consists essentially of nilotinib and the one or more polymers.

Polymers that can be used in the ASDs of the present disclosure may include, but are not limited to, those described below. The term "polymer" includes, but is not limited to, organic homopolymers, copolymers (such as for example, block, graft, random, and terpolymers, etc.), and blends and modifications thereof. The term "copolymer" refers to polymers containing two or more different monomeric units or segments, and includes terpolymers, tetrapolymers, etc. Information regarding suitable polymers, and commercial sources therefor, can be found in Sheskey PJ (ed.) *Handbook of Pharmaceutical Excipients, 9th Ed.* London: Pharmaceutical Press; 2020 (ISBN 0857113755); alternatively, the most up-to-date edition of the same title may be consulted.

Polymers that can be used in the ASDs of the present disclosure may include ionizable or non-ionizable polymers, or a combination thereof.

In some embodiments, the one or more polymers may be non-ionizable polymers. In certain embodiments, the ASD consists of nilotinib and one or more non-ionizable polymers. In certain other embodiments, the ASD consists essentially of nilotinib and one or more non-ionizable polymers.

In some embodiments, the one or more polymers may be ionizable polymers. In certain embodiments, the ASD consists of nilotinib and one or more ionizable polymers. In certain other embodiments, the ASD consists essentially of nilotinib and one or more ionizable polymers.

In yet other embodiments, a combination of ionizable and non-ionizable polymers may be used. In certain embodiments, the ASD consists of nilotinib and a combination of one or more non-ionizable polymers and one or more ionizable polymers. In certain other embodiments, the ASD consists essentially of nilotinib and a combination of one or more non-ionizable polymers and one or more ionizable polymers.

Polymers that can be used in the ASDs of the present disclosure may include polymers that exhibit pH-dependent solubility, or polymers that are generally insensitive to pH, or a combination thereof.

In some embodiments, the one or more polymers may exhibit pH-dependent solubility. In certain embodiments, the ASD consists of nilotinib and one or more polymers that exhibits pH-dependent solubility. In certain other embodiments, the ASD consists essentially of nilotinib and one or more polymers that exhibits pH-dependent solubility.

In other embodiments, the one or more polymers may be generally insensitive to pH. In certain embodiments, the ASD consists of nilotinib and one or more polymers generally insensitive to pH. In certain other embodiments, the ASD consists essentially of nilotinib and one or more polymers generally insensitive to pH.

In yet other embodiments, a combination of polymers may include one or more polymers exhibiting pH-dependent solubility and one or more polymers generally insensitive to pH. In certain embodiments, the ASD consists of nilotinib and a combination of one or more polymers exhibiting pH-dependent solubility and one or more polymers generally insensitive to pH. In certain other embodiments, the ASD consists essentially of nilotinib and a combination of one or more polymers exhibiting pH-dependent solubility and one or more polymers generally insensitive to pH.

Non-ionizable polymers. Suitable non-ionizable polymers may include: polysaccharides and polysaccharide derivatives (including cellulose ethers and non-ionizable cellulose esters); polymers or copolymers of N-vinylpyrrolidone and/or vinyl acetate; polymers of ethylene oxide; homopolymers or copolymers of lactic acid and/or glycolic acid; maleic anhydride copolymers; polyvinyl caprolactam-polyvinyl acetate-polyethylene glycol graft copolymer; and poloxamers.

Suitable non-ionizable polysaccharides and polysaccharide derivatives may include cellulose ethers and non-ionizable cellulose esters. Examples of suitable cellulose ethers include methylcellulose ("MC"; e.g., METHOCEL A15 LV, METHOCEL A4M), ethylcellulose ("EC"; e.g., ETHOCEL), hypromellose or hydroxypropyl methylcellulose ("HPMC"; e.g., METHOCEL E3, METHOCEL E5, METHOCEL E6, METHOCEL E15, AFFINISOL IPMC HME), hydroxyethyl cellulose ("HEC"; e.g., NATROSOL 250 Pharm), and hydroxypropyl cellulose ("HPC"; e.g., HPC EF, HPC LF, HPC JF, HPC L, KLUCEL).

Examples of non-ionizable cellulose esters that may be suitable include cellulose acetate, cellulose propionate, cellulose butyrate, and cellulose acetate butyrate.

Examples of suitable polymers or copolymers of N-vinylpyrrolidone and/or vinyl acetate include polyvinylpyrrolidone ("PVP"; e.g., PVP K25, PVP K90, VIVAPHARM PVP), crospovidone or crosslinked polyvinylpyrrolidone (e.g., KOLLIDON CL, VIVAPHARM PVPP), copovidone or vinylpyrrolidone/vinyl acetate copolymer ("PVP/VA"; e.g., KOLLIDON VA 64, VIVAPHARM PVP/VA 64), and polyvinyl alcohol ("PVA"; e.g., VIVAPHARM PVA).

Examples of suitable polymers of ethylene oxide include polyethylene glycol ("PEG"; e.g., KOLLISOLV PEG 8000) and poly(ethylene oxide) ("PEO"; e.g., POLYOX).

Examples of suitable homopolymers or copolymers of lactic acid and/or glycolic acid include polylactide or poly (lactic acid) ("PLA"), polyglycolide or poly(glycolic acid) ("PGA"), and poly(lactic-co-glycolic acid) ("PLGA").

Non-ionizable maleic anhydride copolymers such as poly (methyl vinyl ether/maleic anhydride) ("PVM/MA") may also be suitable. Non-ionizable poloxamers (e.g., PLURONIC, KOLLIPHOR) may also be suitable.

A polyvinyl caprolactam-polyvinyl acetate-polyethylene glycol graft copolymer (e.g., SOLUPLUS) may also be a suitable non-ionizable polymer.

Ionizable polymers. Suitable ionizable polymers may be considered "anionic" or "cationic" polymers. Anionic and cationic polymers often exhibit pH-dependent solubility.

Anionic polymers often include carboxylate (such as acetate), phthalate, succinate, or acrylate functionalities. Anionic polymers are generally insoluble at low pH and more soluble at higher pH. Suitable anionic polymers may include anionic polysaccharides and polysaccharide derivatives (such as ionizable cellulose esters), copolymers of methacrylic acid and/or alkyl acrylate, and derivatized vinyl acetate polymers, for example.

An example of an ionizable polysaccharide that may be suitable is xanthan gum. Examples of suitable ionizable cellulose esters may include carboxymethylcellulose ("CMC"; carboxymethylcellulose sodium), hypromellose acetate succinate, or hydroxypropyl methylcellulose acetate succinate ("HPMC-AS"; e.g., AFFINISOL HPMC-AS, AQUASOLVE, AQOAT), hydroxypropyl methylcellulose phthalate ("HPMC-P"; e.g., HP-50, HP-55), and cellulose acetate phthalate ("CAP"; e.g., EASTMAN C-A-P).

Suitable copolymers of methacrylic acid and/or alkyl methacrylate may include methacrylic acid/methyl methacrylate copolymer (e.g., EUDRAGIT L100) and methacrylic acid/ethyl acrylate copolymer (e.g., EUDRAGIT L100-55, KOLLICOAT MAE).

An example of a derivatized vinyl acetate polymer that may be suitable is polyvinyl acetate phthalate (PVA-P; PHTHALAVIN).

Cationic polymers often include amine functionalities. Cationic polymers are generally soluble at low pH and less soluble at higher pH. Suitable cationic polymers may include cationic polysaccharides and polysaccharide derivatives, and amine-functionalized copolymers of methacrylic acid and/or alkyl acrylate, for example.

An example of a cationic polysaccharide that may be suitable is chitosan.

Suitable amine-functionalized copolymers of methacrylic acid and/or alkyl acrylate include, for example, dimethylaminoethyl methacrylate/butyl methacrylate/methyl methacrylate copolymer (e.g., EUDRAGIT E100) and aminoalkyl methacrylate copolymer such as poly(ethyl acrylate-co-methyl methacrylate-co-trimethylammonioethyl methacrylate chloride (e.g., EUDRAGIT RL100, EUDRAGIT RL PO, EUDRAGIT RS PO).

In some embodiments, the one or more polymers comprise polymers that are characterized by pH-dependent solubility. In some embodiments, the one or more polymers comprise an anionic polymer characterized by pH-dependent solubility. In some embodiments, the one or more polymers consist essentially of one or more anionic polymers characterized by pH-dependent solubility. In some embodiments, the one or more polymers consist of one or more anionic polymers characterized by pH-dependent solubility.

HPMC-AS and EUDRAGIT L100-55 are examples of suitable anionic polymers that demonstrate pH-dependent solubility, but other polymers that demonstrate pH-dependent solubility may also be employed.

In certain embodiments, the one or more polymers comprise HPMC-AS. In certain embodiments, the polymer consists of HPMC-AS. In certain embodiments, the polymer consists essentially of HPMC-AS.

HPMC-AS is available in a variety of grades, which each demonstrate pH-dependent aqueous solubility. Generally speaking, HPMC-AS is largely insoluble in an aqueous medium at pH of 4 or lower, and largely soluble in an aqueous medium at pH 7 or greater. It is insoluble in normal gastric fluid, but swells and dissolves in the higher pH environment of the upper small intestine. The grades of HPMC-AS are differentiated by the relative proportion of acetyl/succinyl substituents. Low-grade HPMC-AS comprises 5-9% acetyl substituents and 14-18% succinyl substituents; mid-grade HPMC-AS comprises 7-11% acetyl substituents and 10-14% succinyl substituents; high-grade HPMC-AS comprises 10-14% acetyl substituents and 4-8% succinyl substituents. In the practice of the disclosure, any grade of HPMC-AS may be suitable, or a mixture of two or more grades may be suitable. In certain embodiments, mid-grade HPMC-AS is particularly suitable.

In certain embodiments, the ASD consists of nilotinib and HPMC-AS. In certain embodiments, the ASD consists essentially of nilotinib and HPMC-AS. In certain embodiments, the ASD consists of anhydrous, free base nilotinib and HPMC-AS. In certain embodiments, the ASD consists essentially of anhydrous, free base nilotinib and HPMC-AS. In certain embodiments, the ASD consists of nilotinib and mid-grade HPMC-AS. In certain embodiments, the ASD consists essentially of nilotinib and mid-grade HPMC-AS. In certain embodiments, the ASD consists of anhydrous, free base nilotinib and mid-grade HPMC-AS. In certain embodiments, the ASD consists essentially of anhydrous, free base nilotinib and mid-grade HPMC-AS.

In some embodiments, the one or more polymers comprise a copolymer of methacrylic acid and/or alkyl methacrylate. In some embodiments, the one or more polymers comprise methacrylic acid/methyl methacrylate copolymer (e.g., EUDRAGIT L100) or methacrylic acid/ethyl acrylate copolymer (e.g., EUDRAGIT L100-55).

In some embodiments, the one or more polymers comprise methacrylic acid/ethyl acrylate copolymer. In certain embodiments, the polymer consists of methacrylic acid/ethyl acrylate copolymer. In certain embodiments, the polymer consists essentially of methacrylic acid/ethyl acrylate copolymer.

In some embodiments, the ASD comprises nilotinib and methacrylic acid/ethyl acrylate copolymer. In certain embodiments, the ASD consists of nilotinib and methacrylic acid/ethyl acrylate copolymer. In certain other embodiments, the ASD consists essentially of nilotinib and methacrylic acid/ethyl acrylate copolymer. In certain embodiments, the ASD comprises anhydrous, free base nilotinib and methacrylic acid/ethyl acrylate copolymer. In certain embodiments, the ASD consists of anhydrous, free base nilotinib and methacrylic acid/ethyl acrylate copolymer. In certain embodiments, the ASD consists essentially of anhydrous, free base nilotinib and methacrylic acid/ethyl acrylate copolymer.

In any of the foregoing, the methacrylic acid/ethyl acrylate copolymer can be EUDRAGIT L100-55, for example. EUDRAGIT L100-55 is an anionic copolymer demonstrating pH-dependent aqueous solubility. Generally speaking, EUDRAGIT L100-55 is largely insoluble in an aqueous medium at pH of 5 or lower, and largely soluble in an aqueous medium at pH 5.5 or greater.

In some embodiments of the ASD, the one or more polymers does not comprise a polyvinyl caprolactam-polyvinyl acetate-polyethylene glycol graft co-polymer (e.g., SOLUPLUS). In some embodiments, the ASD is substantially free from a polyvinyl caprolactam-polyvinyl acetate-polyethylene glycol graft co-polymer. In some embodiments, the ASD is essentially free from a polyvinyl caprolactam-polyvinyl acetate-polyethylene glycol graft co-polymer. In some embodiments, the ASD is free from a polyvinyl caprolactam-polyvinyl acetate-polyethylene glycol graft co-polymer. In yet other embodiments, the ASD comprises nilotinib and one or more polymers, with the proviso that the one or more polymer is not a polyvinyl caprolactam-polyvinyl acetate-polyethylene glycol graft co-polymer.

In some embodiments of the ASD, the one or more polymers does not comprise a poloxamer. In some embodiments, the ASD is substantially free from a poloxamer. In some embodiments, the ASD is essentially free from a poloxamer. In some embodiments, the ASD is free from a poloxamer. In yet other embodiments, the ASD comprises nilotinib and one or more polymers, with the proviso that the one or more polymer is not a poloxamer.

In some embodiments of the ASD, the one or more polymers does not comprise an anionic polymer comprising phthalate functionalities. In some embodiments, the ASD is substantially free from an anionic polymer comprising phthalate functionalities. In some embodiments, the ASD is essentially free from an anionic polymer comprising phthalate functionalities. In some embodiments, the ASD is free from an anionic polymer comprising phthalate functionalities. In yet other embodiments, the ASD comprises nilotinib and one or more polymers, with the proviso that the one or more polymer is not an anionic polymer comprising phthalate functionalities.

In some embodiments of the ASD, the one or more polymers does not comprise a hydroxypropyl methylcellulose phthalate. In some embodiments, the ASD is substantially free from a hydroxypropyl methylcellulose phthalate. In some embodiments, the ASD is essentially free from a hydroxypropyl methylcellulose phthalate. In some embodiments, the ASD is free from a hydroxypropyl methylcellulose phthalate. In yet other embodiments, the ASD comprises nilotinib and one or more polymers, with the proviso that the one or more polymer is not a hydroxypropyl methylcellulose phthalate.

In some embodiments of the ASD, the one or more polymers does not comprise a polyvinyl acetate phthalate. In some embodiments, the ASD is substantially free from a polyvinyl acetate phthalate. In some embodiments, the ASD is essentially free from a polyvinyl acetate phthalate. In some embodiments, the ASD is free from a polyvinyl acetate phthalate. In yet other embodiments, the ASD comprises nilotinib and one or more polymers, with the proviso that the one or more polymer is not a polyvinyl acetate phthalate.

In some embodiments of the ASD, the one or more polymers does not comprise a polymer or copolymer of N-vinylpyrrolidone. In some embodiments, the ASD is substantially free from a polymer or copolymer of N-vinylpyrrolidone. In some embodiments, the ASD is essentially free from a polymer or copolymer of N-vinylpyrrolidone. In some embodiments, the ASD is free from a polymer or copolymer of N-vinylpyrrolidone. In yet other embodiments, the ASD comprises nilotinib and one or more polymers, with the proviso that the one or more polymer is not a polymer or copolymer of N-vinylpyrrolidone. In the foregoing, the polymer or copolymer of N-vinylpyrrolidone can be polyvinylpyrrolidone, crospovidone or crosslinked polyvinylpyrrolidone, copovidone or vinylpyrrolidone/vinyl acetate copolymer.

As used herein, the phrase "substantially free from" means that the stated component represents not more than 10% of the ASD, based on weight. The phrase "essentially free from" means that the stated component represents not more than 5% of the ASD, based on weight. The term "free from" means that the stated component represents not more than 2% of the ASD, based on weight.

In the ASDs described in the disclosure, the amount of nilotinib as compared to the amount of the one or more polymers may vary. For example, nilotinib and the one or more polymers may be present in a w/w ratio (nilotinib: polymer) of 20:80 to 95:5. In certain embodiments, nilotinib and the one or more polymers may be present in a w/w ratio of 25:75 to 90:10, or 30:70 to 85:15, or 35:65 to 80:20. In some embodiments, nilotinib and the one or more polymers may be present in a w/w ratio of 40:60 to 70:30. In particular embodiments, the w/w ratio is 20:80, 25:75, 30:70, 35:65, 40:60, 45:55, 50:50, 55:45, 60:40, 65:35, 70:30, 75:25, 80:20, 85:15, 90:10, or 95:5.

In some embodiments, the ASD consists of nilotinib and one or more polymers. In some embodiments, the ASD consists essentially of nilotinib and one or more polymers. In other embodiments, the ASDs of the present disclosure may additionally comprise one or more other pharmaceutically acceptable functional components, such as one or more antioxidants, wetting agents, or solubilizers.

As used herein, the phrase "pharmaceutically acceptable" means that the component does not initiate a pharmacological response or an adverse reaction when introduced to a relevant biological system. By way of non-limiting example only, a substance found in the U.S. Food & Drug Administration's "Generally Recognized as Safe" ("GRAS") list, or a substance used in accordance with guidelines in its Inactive Ingredient Database, would be considered pharmaceutically acceptable. Similarly, a substance in a corresponding database or list maintained by a parallel regulatory body, such as the European Medicines Agency, would be considered pharmaceutically acceptable. In general, in the pharmaceutical compositions of the disclosure, it is desirable to employ only components that do not cause an unacceptable level of physical or chemical instability in the resulting composition.

Examples of antioxidants that that may be used in the ASDs of the present disclosure include, but are not limited to, acetylcysteine, ascorbyl palmitate, butylated hydroxyanisole ("BHA"), butylated hydroxytoluene ("BHT"), monothioglycerol, potassium nitrate, sodium ascorbate, sodium formaldehyde sulfoxylate, sodium metabisulfite, sodium bisulfite, vitamin E or a derivative thereof, propyl gallate, ethylenediaminetetraacetic acid ("EDTA") (e.g., disodium edetate), diethylenetriaminepentaacetic acid ("DTPA"), bismuth sodium triglycollamate, or a combination thereof. Antioxidants may also comprise amino acids such as methionine, histidine, cysteine and those carrying a charged side chain, such as arginine, lysine, aspartic acid, and glutamic acid. Any stereoisomer (e.g., l-, d-, or a combination thereof) of any particular amino acid (e.g., methionine, histidine, arginine, lysine, isoleucine, aspartic acid, tryptophan, threonine and combinations thereof) or combinations of these stereoisomers, may be present so long as the amino acid is present either in its free base form or its salt form.

In some embodiments, the one or more antioxidants comprise BHT. In some embodiments, the one or more antioxidants consist of BHT.

The one or more antioxidants may be present in the ASD in an amount of 0.001% to 2.0%, or 0.01% to 1.5%, or 0.05% to 1.0%, or 0.1% to 0.5%, or 0.3% to 0.4%, by weight. Examples of the amount of the one or more antioxidants in the ASD include 0.001%, or 0.003%, or 0.005%, or 0.008%, or 0.01%, or 0.015%, or 0.02%, or 0.025%, or 0.03%, or 0.035%, or 0.04%, or 0.05%, or 0.075%, or 0.1%, or 0.2%, or 0.3%, or 0.4%, or 0.5%, or 0.75%, or 1.0%, or 1.5%, or 2.0%, by weight.

A variety of pharmaceutically acceptable wetting agents may be included. As a non-limiting example of a wetting agent, poloxamers, such as poloxamer 407 (e.g., PLURONIC F-127) or poloxamer 188 (e.g., PLURONIC F-68), may be suitable. Other known pharmaceutically acceptable wetting agents may be suitably employed. A wetting agent may be included in the ASD in an amount of 0.5% to 10%, or 1% to 8%, or 2% to 6%, by weight.

A variety of pharmaceutically acceptable solubilizers may be included. Non-limiting examples of suitable solubilizers include vitamin E TPGS (D-α-tocopherol polyethylene glycol succinate), SLS (sodium lauryl sulfate), and docusate sodium. Other known pharmaceutically acceptable solubilizers may be suitably employed. A solubilizer may be included in the ASD in an amount of 0.1% to 10%, or 0.25% to 5%, or 0.5 to 1%, by weight.

In some embodiments, the ASD comprises nilotinib, one or more polymers, and one or more antioxidants. In certain embodiments, the ASD consists essentially of nilotinib, one or more polymers, and one or more antioxidants. In certain embodiments, the ASD consists of nilotinib, one or more polymers, and one or more antioxidants.

In some embodiments, the ASD comprises nilotinib, HPMC-AS, and BHT. In certain embodiments, the ASD consists essentially of nilotinib, HPMC-AS, and BHT. In certain embodiments, the ASD consists of nilotinib, HPMC-AS, and BHT. In some embodiments, the ASD comprises nilotinib, mid-grade HPMC-AS, and BHT. In certain embodiments, the ASD consists essentially of nilotinib, mid-grade HPMC-AS, and BHT. In certain embodiments, the ASD consists of nilotinib, mid-grade HPMC-AS, and BHT.

In particular embodiments, the ASD consists essentially of nilotinib and HPMC-AS at a ratio of 50:50, and BHT in at a level of 0.1-0.5% by weight of the ASD. In particular embodiments, the ASD consists of nilotinib and HPMC-AS at a ratio of 50:50, and BHT in at a level of 0.1-0.5% by weight of the ASD.

In some embodiments, the ASD comprises nilotinib, methacrylic acid/ethyl acrylate copolymer (such as EUDRAGIT L100-55), and BHT. In certain embodiments, the ASD consists essentially of nilotinib, a methacrylic acid/ethyl acrylate copolymer, and BHT. In certain embodiments, the ASD consists of nilotinib, methacrylic acid/ethyl acrylate copolymer, and BHT.

In particular embodiments, the ASD consists essentially of nilotinib, methacrylic acid/ethyl acrylate copolymer (such as EUDRAGIT L100-55), and BHT at a level of 0.1-0.5%, by weight of the ASD. In particular embodiments, the ASD consists of nilotinib, methacrylic acid/ethyl acrylate copolymer, and BHT at a level of 0.1-0.5%, by weight of the ASD.

The drug load of nilotinib in the ASDs of the present disclosure may suitably range from 20% to 95%, or 25% to 90%, or 30% to 80%, or 35% to 70%, or 40% to 60%, or 45% to 55%. As used herein, the phrase "drug load" refers to the ratio (by weight %) of nilotinib in an ASD to the total solids weight of the ASD. By way of example, for an ASD consisting of nilotinib and a polymer, a 1:1 w/w ratio of nilotinib:polymer would represent a 50% drug load; a 1:2 w/w ratio of nilotinib:polymer would represent a 33.3% drug load, etc. Examples of the drug load of nilotinib in specific embodiments of the ASDs include 40%, or 45%, or 50%, or 55%, or 60%, or 65%, or 70%, or 75%, or 80%, or 85%, or 90%.

The nilotinib ASDs may be in the form of particles. In some embodiments, the particles do not comprise a surfactant. In other embodiments, the particles do not comprise a wetting agent. In other embodiments, the particles do not comprise a solubilizer. In other embodiments, the particles comprise neither a surfactant nor a solubilizer. In other embodiments, the particles are free from surfactants, wetting agents, and solubilizers. In other embodiments, the particles consist of polymer and nilotinib, and no additional functional components.

Particles of the ASDs of the disclosure may generally comprise the shapes of spheroids. As measured by conventional light scattering or laser diffraction techniques, the diameter of the particles may generally range from about 0.05 m to about 100 m. The median diameter (D50 or Dv0.5) of the particle distribution may be in the range from 0.2 m to 60 m, or 0.5 m to 50 m, or 0.5 m to 40 μm.

In some embodiments, the median diameter of the particle distribution may be from 1 m to 40 μm, or from 2 m to 25 μm, or from 3 m to 20 μm. By way of example only, such particle size distributions can be achieved by known methods of spray drying.

In some embodiments, the median diameter of the particle distribution may be from 0.1 m to 10 μm, or from 0.2 μm to 5 μm, or from 0.5 m to 2 μm. By way of example only, such particle size distributions can be achieved by methods involving electrospraying, discussed further below.

The nilotinib ASDs of the present disclosure may demonstrate a desirable level of physical and/or chemical stability, which can be assessed by different measures. Stability is generally assessed using conventional analytical techniques commonly known in pharmaceutical sciences.

Physical and chemical stability is generally assessed after storage under controlled, elevated environmental conditions ("accelerated conditions") over a specified period of time. The storage conditions may be one or more of 25° C./60% relative humidity ("RH"), or 25° C./protected, or 30° C./65% RH, or 40° C./75% RH, or 40° C./protected, or 50° C./80% RH. (As used herein in this context, "protected" means samples were sealed in foil pouches and placed in a controlled chamber for the storage period). The period of time may be one or more of 1 week, or 2 weeks, or 4 weeks or 1 month, or 2 months, or 3 months, or 4 months, or 6 months, or 9 months, or 12 months, or 15 months, or 18 months, or 21 months, or 24 months, or any period of time therebetween.

The nilotinib ASDs may demonstrate stability by having a particular assay value or a particular level of total related substances (e.g., impurities), as measured by high performance liquid chromatography ("HPLC"), after storage under accelerated conditions over a specified period of time. The assay value is generally presented as a percentage of the quantity of analyte (e.g., nilotinib) detected relative to the quantity expected, where 100% is a favorable result and large deviations from 100% are unfavorable. The total related substances is generally presented as a percentage relative to the total quantity of substances detected (i.e., analyte plus impurities), where near 0% is favorable and large deviations from 0% are unfavorable.

In some embodiments, the nilotinib ASDs may have an assay as measured by HPLC of at least 90%, or at least 93%, or at least 95%, or at least 97%, or at least 98%, or at least 99%. In some embodiments, the nilotinib ASDs may have a level of total related substances as measured by HPLC of no more than 3%, no more than 2.5%, no more than 2%, or no more than 1.5%, or no more than 1%, or no more than 0.9%, or no more than 0.8%, or no more than 0.7%, or no more than 0.6%, or no more than 0.5%.

In some embodiments, the nilotinib ASDs may have an assay as measured by HPLC of at least 90%, or at least 93%, or at least 95%, or at least 97%, or at least 98%, after storage at 25° C./60% RH for 1 month, or 2 months, or 3 months, or 6 months, or 9 months, or 12 months; or after storage at 40° C./75% RH for 1 month, or 2 months, or 3 months, or 6 months.

In some embodiments, the nilotinib ASDs may have a level of total related substances as measured by HPLC of no more than 2%, or no more than 1.5%, or no more than 1%, or no more than 0.9%, or no more than 0.8%, or no more than 0.7%, or no more than 0.6%, or no more than 0.5%, after storage at 25° C./60% RH for 1 month, or 2 months, or 3 months, or 6 months, or 9 months, or 12 months; or after storage at 40° C./75% RH for 1 month, or 2 months, or 3 months, or 6 months.

Stability may also be assessed by evaluating changes in glass transition temperature of the nilotinib ASDs under different storage conditions over time. Glass transition temperature can be evaluated by modulated DSC ("mDSC") using conventional techniques. In some embodiments, the ASD is characterized by a single glass transition, the transition observed in the range from 25° C. to 200° C., or more suitably from 40° C. to 150° C., by DSC or mDSC. In other embodiments, the ASD is characterized by more than one transition, the transitions observed in the range from 25° C. to 200° C., or more suitably from 40° C. to 150° C., by DSC or mDSC.

In some embodiments, the glass transition temperature as measured by mDSC does not change by more than 5° C., or more than 4° C., or no more than 3° C., or no more than 2° C., after storage at 25° C./60% RH for 1 month, or 2 months, or 3 months, or 6 months, or 9 months, or 12 months. In some embodiments, the glass transition temperature as measured by mDSC does not change by more than 6° C., or more than 5° C., or more than 4° C., or more than 3° C., or more than 2° C., or no more than 1° C., after storage at 40° C./75% RH for 1 month, or 2 months, or 3 months, or 6 months.

Further, stability may be assessed by evaluating changes in crystallinity of the nilotinib ASDs under different storage conditions over time, such as by suitable conventional x-ray diffraction ("XRD") techniques (also known in the art as powder XRD or PXRD). In the practice of the present disclosure, it is preferred (but not required) that the nilotinib ASDs remain amorphous or essentially amorphous. In some embodiments, "amorphous" may be defined as having no detectable crystallinity as determined using methods known in the art, for instance, by using XRD. An example of using XRD to determine amorphicity is provided in Example 1.

In some embodiments, "amorphous" may be defined as having a percent crystallinity no more than 5%, or no more than 4%, or no more than 3%, or no more than 2%, or no more than 1%, as determined by XRD. In some embodiments, "essentially amorphous" may be defined as having a percent crystallinity of no more than 8%, or no more than 7%, or no more than 6%, as measured by XRD.

The ASDs of the disclosure may be amorphous or essentially amorphous when analyzed promptly after preparation, i.e., at t=0. For these purposes, the phrase "promptly after preparation" means that the ASD is analyzed within a few days after preparation, and stored under protected conditions at ambient temperature and humidity after preparation and before analysis.

The ASDs may be amorphous or essentially amorphous after storage under various storage conditions (e.g., 25° C./60% RH, 25° C./protected, 40° C./75% RH, 40° C./protected, 50° C./80% RH, etc.) for a period of at least 1 week, or a period of at least 2 weeks, or a period of at least 3 weeks, or a period of at least 4 weeks or 1 month, or a period of at least 2 months, or a period of at least 3 months, or a period of at least 4 months, or a period of at least 5 months, or a period of at least 6 months, or a period of at least 9 months, or a period of at least 12 months or 1 year. In some embodiments, the ASDs of the disclosure may be amorphous or essentially amorphous under conditions of high temperature and humidity (e.g., 40° C./75% RH) for a period of at least 1 month, or a period of at least 2 months, or a period of at least 3 months, or a period of at least 6 months.

The nilotinib ASDs of the present disclosure can be characterized for water content, such as by using standard Karl Fischer coulometric titration methods. In some embodiments, the nilotinib ASDs may comprise a water content as assessed by Karl Fischer coulometric titration method of no more than 3%, or no more than 2.5%, or no more than 2%, or no more than 1.5%, or no more than 1%.

In some embodiments, the nilotinib ASDs may comprise a water content as assessed by Karl Fischer coulometric titration method of no more than 5%, or no more than 4.5%, or no more than 4%, or no more than 3.5%, or no more than 3%, or no more than 2.5%, or no more than 2%, after storage at 25° C./60% RH for 1 month, or 2 months, or 3 months, or 6 months, or 9 months, or 12 months. In some embodiments, the nilotinib ASDs may comprise a water content as assessed by Karl Fischer coulometric titration method of no more than 8%, or no more than 7%, or no more than 6%, or no more than 5%, or no more than 4.5%, or no more than 4%, or no more than 3.5%, or no more than 3%, or no more than 2.5%, or no more than 2%, after storage at 40° C./75% RH for 1 month, or 2 months, or 3 months, or 6 months, or 9 months, or 12 months.

Methods of Making Amorphous Solid Dispersions

The nilotinib ASDs of the present disclosure may be prepared by a variety of methods known in the art. Suitable methods generally include mixing, dissolving, or compounding the nilotinib and the one or more polymers and, if present, one or more other functional components (such as antioxidants, wetting agents, or solubilizers) to integrate the various components. In the practice of the various methods, the nilotinib may be introduced as nilotinib free base, or as a salt of nilotinib, or as a solvate or hydrate of nilotinib.

Suitable methods are generally known in the art, and include kneading, co-grinding, melting, melt extrusion, melt agglomeration, dropping, and the like. After the integration step, the material can be further processed by drying, grinding or crushing, sieving, etc.

In the practice of certain methods, nilotinib and the one or more polymers (and other functional components, if present) may be mixed or dissolved with one or more solvents to provide a liquid feedstock. Suitable solvents may include, but are not limited to, water; an alcohol, such as ethanol, methanol, propanol or isopropanol; an ether, such as ethyl ether or methyl tert-butyl ether; acetonitrile; tetrahydrofuran or methyl tetrahydrofuran; an acetate, such as methyl acetate or ethyl acetate; a ketone, such as acetone or 2-butanone (methyl ethyl ketone, or "MEK"); toluene; ethyl formate; 1,4-dioxane; dimethylsulfoxide; N-methyl 2-pyrrolidone; volatile halogenated solvents such as chloroform or dichloromethane; and combinations thereof. The mixing or dissolving of these contents may be by methods known in the art. For example, the contents may be mixed by manually mixing, or may be mixed with a mixing device continuously, periodically, or a combination thereof. Examples of mixing devices may include, but are not limited to, a magnetic stirrer, shaker, a paddle mixer, homogenizer, and any combination thereof.

After the nilotinib and the one or more polymers (and other functional components, if present) are mixed, the liquid feedstock may be formed into an amorphous solid dispersion, such as through solvent evaporation, lyophilization, precipitation or co-precipitation, spray drying, electrospraying, supercritical fluid extraction, etc. These methods are known and commonly understood in the art.

In certain embodiments of the disclosure, the liquid feedstock may be formed into an amorphous solid dispersion through electrospraying. Electrospraying, which has also been referred to as electrohydrodynamic atomization, has been used to produce amorphous solid dispersion particles on a micron or sub-micron scale from suitable liquid feedstocks.

In one suitable electrospraying technique, the liquid feedstock is emitted through one or more nozzles toward a substrate in the presence of an electric potential applied between the nozzles and the substrate. The liquid feedstock experiences electrical shear stress due to the applied potential. When the shear stress overcomes the surface tension of the liquid feedstock, droplets are emitted from the tips of the nozzles.

Conditions are controlled such that a cone jet of droplets is emitted at the tip of the nozzles. The droplets take on an electric charge and repel one another, which prevents their coagulation and promotes self-dispersion. The charged droplets accelerate toward the substrate as a result of the applied electric field.

During the short flight path, the solvent "flashes off" from the charged droplets. This fast evaporation creates a situation in which the charged droplets shrink in size but increase in charge density. At a critical limit, the droplets will break up into yet smaller droplets. An essentially monodisperse population of fine droplets is ultimately produced. The size of the droplets can range from sub-micron to several microns.

The essentially complete evaporation of solvent from the charged droplets results in the formation of relatively uniform particles of the non-volatile components from the liquid feedstock. The evaporation process occurs at a timescale that does not permit crystallization of the non-volatile components. Additionally, evaporative cooling associated with the extremely rapid solvent evaporation contributes a quenching effect to preserve the particles in an amorphous state. Furthermore, electrospray conditions can be selected and the system can be configured such that the amorphous particles contain little residual solvent.

In some embodiments of the disclosure, the liquid feedstock may be formed into an ASD using electrospray techniques and/or devices. Suitable methods and equipment are described, for example, in U.S. Pat. Nos. 6,746,869, 6,764,720, 7,279,322, 7,498,063, 7,951,428, 7,972,661, 8,992,603, 9,040,816, 9,050,611, 9,108,217, 9,642,694, 10,562,048, U.S. Patent Publication No. 2014-0158787, U.S. Patent Publication No. 2015-0190253, U.S. Patent Publication No. 2016-0038968, U.S. Patent Publication No. 2016-0175881, U.S. Patent Publication No. 2016-0235677, U.S. Patent Publication No. 2019-0193109, and U.S. Patent Publication No. 2020-0179963.

As noted above, by using an electrospray technique, the median diameter of the nilotinib ASD particle distribution may be from 0.1 m to 10 m, or from 0.2 m to 5 m, or from 0.5 m to 2 m. It should further be noted that the nilotinib in the amorphous particles is generally not considered to be solvated. Even where the liquid feedstock may have been prepared using a solvate or hydrate form of nilotinib, the solvate or hydrate is understood to flash off with the other solvents, and the electrosprayed amorphous particles comprise non-solvated nilotinib (such as anhydrous nilotinib).

In some embodiments, the electrospray technique may be performed at room temperature. In certain embodiments, no heated air is used. In other embodiments, the liquid feedstock is held at an elevated temperature during the electrospray process.

In some embodiments, the electrospray technique may be performed using one or more capillary nozzles. In certain embodiments, the electrospray technique does not use pneumatic nozzles such as nozzles that rely on kinetic energy; pressure nozzles; rotary nozzles; or nozzles that rely on centrifugal energy; or ultrasonic nozzles such as nozzles that rely on acoustic energy. In some embodiments, the electrospray technique generates a yield of over 85%, or over 90%, or over 95%, or over 98%.

In other embodiments, the liquid feedstock may be formed into an ASD through spray drying. Generally speaking, spray drying involves the atomization of a liquid feedstock into very small droplets within a hot drying gas. The feedstock is pumped or otherwise propelled through a nozzle or other atomizing apparatus to form droplets within a drying chamber. Within the drying chamber, the droplets are exposed to an environment of the heated drying gas (usually flowing air or nitrogen), leading to flash drying of the droplets (by evaporative removal of solvent) and resultant production of solid particles. The dried particles are collected, generally at an output port in the drying chamber.

Various apparatus and methods of spray drying may be employed to form an ASD of the disclosure. In the practice of the present disclosure, the median diameter of the ASD particle distribution achieved by spray drying may be from 1 µm to 40 µm, or from 2 µm to 25 µm, or from 3 µm to 20 µm.

In some embodiments, the process for forming an ASD does not require a secondary drying step, i.e., a drying step that occurs after the particles are produced. In other embodiments, a secondary drying step is employed to further remove most or all of the residual solvents. The secondary drying step can be done under suitable conditions that allow for the removal of solvent but do not result in the recrystallization of the nilotinib. For example, a secondary drying step can be done below a glass transition temperature. A secondary drying step can also be done at reduced pressure. A combination of elevated temperature and reduced pressure can also be used for a secondary drying step.

Pharmaceutical Compositions

An aspect of the present disclosure relates to pharmaceutical compositions comprising nilotinib ASD. The pharmaceutical compositions of the present disclosure may be in a dosage form appropriate for oral administration. In some embodiments, the pharmaceutical compositions may be in the form of granules, or may be prepared as granules as an intermediate step to forming another oral dosage form, such as tablets, sprinkles, or pellets. In some embodiments, the pharmaceutical compositions may be in a solid dosage form for oral administration, such as a capsule, tablet, sprinkle, or pellet. The pharmaceutical composition may also be in the form of an aqueous or nonaqueous suspension or solution. Such compositions may be prepared using known excipients and known preparation methods.

The compositions may comprise a nilotinib ASD of the present disclosure and one or more pharmaceutically acceptable excipients, such as one or more solubilizers, one or more buffering agent(s), one or more pH-adjusting agents, one or more surfactants, one or more antioxidants, and/or one or more carriers. Pharmaceutical compositions in the form of solid oral dosage forms may also comprise one or more filling agents, one or more binding agents, one or more lubricants, one or more disintegrants, and/or other conventional excipients such as one or more glidants, for example.

Information regarding suitable excipients, and commercial sources therefor, can be found in Sheskey PJ (ed.) *Handbook of Pharmaceutical Excipients*, 9$^{th}$ Ed. London: Pharmaceutical Press; 2020 (ISBN 0857113755); alternatively, the most up-to-date edition of the same title may be consulted.

The pharmaceutical compositions of the present disclosure may be prepared using methods known in the art. For example, the nilotinib ASD and the one or more pharmaceutically acceptable additives may be mixed by simple mixing, or may be mixed with a mixing device continuously, periodically, or a combination thereof. Examples of mixing devices may include, but are not limited to, a magnetic stirrer, shaker, a paddle mixer, homogenizer, and any combination thereof.

Solubilizers that may be used in the pharmaceutical compositions of the present disclosure include, but are not limited to, polyvinyl caprolactam-polyvinyl acetate-polyethylene glycol copolymer (SOLUPLUS), d-α-tocopherol acid polyethylene glycol (PEG) 1000 succinate (TPGS), PEG-40 hydrogenated castor oil (CREMOPHOR RH40), PEG-35 castor oil (CREMOPHOR EL), PEG-40 stearate (MYRJ 540), hard fat (such as GELUCIRE 33/01), polyoxylglycerides (such as GELUCIRE 44/14), stearoyl polyoxylglycerides (such as GELUCIRE 50/13), PEG-8 caprylic/capric glycerides (such as LABRASOL) and poloxamers (such as PLURONIC, KOLLIPHOR).

In some embodiments, the pharmaceutical compositions may comprise a nilotinib ASD and one or more pharmaceutically acceptable excipients, with the proviso that the pharmaceutically acceptable excipients do not comprise polyvinyl caprolactam-polyvinyl acetate-polyethylene glycol graft co-polymer (e.g., SOLUPLUS).

Buffering agents that that may be used in the pharmaceutical compositions of the present disclosure include, but are not limited to, triethylamine, meglumine, diethanolamine, ammonium acetate, arginine, lysine, histidine, a phosphate buffer (e.g., sodium phosphate tribasic, sodium phosphate dibasic, sodium phosphate monobasic, or o-phosphoric acid), sodium bicarbonate, a Britton-Robinson buffer, a Tris buffer (containing Tris(hydroxymethyl)-aminomethane), a HEPES buffer (containing N-(2-hydroxyethyl)piperazine-N'-(2-ethanesulfonic acid), acetate, a citrate buffer (e.g., citric acid, citric acid anhydrous, citrate monobasic, citrate dibasic, citrate tribasic, citrate salt), ascorbate, glycine, glutamate, lactate, malate, formate, sulfate, and mixtures thereof.

Further, pH-adjusting agents that that may be used in the pharmaceutical compositions of the present disclosure include pharmaceutically acceptable acids or bases. For example, acids may include, but are not limited to, one or more inorganic mineral acids such as hydrochloric, hydrobromic, sulfuric, phosphoric, nitric, and the like; or one or more organic acids such as acetic, succinic, tartaric, ascorbic, citric, glutamic, benzoic, methanesulfonic, ethanesulfonic, trifluoroacetic, and the like. The bases may be one or more inorganic bases or organic bases, including, but not limited to, alkaline carbonate, alkaline bicarbonate, alkaline earth metal carbonate, alkaline hydroxide, alkaline earth metal hydroxide, or amine. For example, the inorganic or organic base may be an alkaline hydroxide such as lithium hydroxide, potassium hydroxide, cesium hydroxide, sodium hydroxide, or the like; an alkaline carbonate such as calcium carbonate, sodium carbonate, or the like; or an alkaline bicarbonate such as sodium bicarbonate, or the like; the organic base may also be sodium acetate.

Surfactants that that may be used in the pharmaceutical compositions of the present disclosure may include, but are not limited to, sodium lauryl sulfate, docusate sodium, dioctyl sodium sulfosuccinate, dioctyl sodium sulfonate, benzalkonium chloride, benzethonium chloride, lauromacrogol 400, polyoxyl 40 stearate, polyoxyethylene hydrogenated castor oil (e.g., polyoxyethylene hydrogenated castor oil 10, 50, or 60), glycerol monostearate, polysorbate (e.g., polysorbate 40, 60, 65, or 80), sucrose fatty acid ester, methyl cellulose, polyalcohols and ethoxylated polyalcohols, thiols (e.g., mercaptans) and derivatives, poloxamers, polyethylene glycol-fatty acid esters (e.g., KOLLIPHOR RH40, KOLLIPHOR EL), lecithins, and mixtures thereof.

Antioxidants that that may be used in the pharmaceutical compositions of the present disclosure include, but are not limited to, acetylcysteine, ascorbyl palmitate, BHA, BHT, monothioglycerol, potassium nitrate, sodium ascorbate, sodium formaldehyde sulfoxylate, sodium metabisulfite, sodium bisulfite, vitamin E or a derivative thereof, propyl gallate, EDTA (e.g., disodium edetate), DTPA, bismuth sodium triglycollamate, or a combination thereof. Antioxidants may also comprise amino acids such as methionine, histidine, cysteine and those carrying a charged side chain, such as arginine, lysine, aspartic acid, and glutamic acid. Any stereoisomer (e.g., l-, d-, or a combination thereof) of any particular amino acid (e.g., methionine, histidine, arginine, lysine, isoleucine, aspartic acid, tryptophan, threonine and combinations thereof) or combinations of these stereoisomers, may be present so long as the amino acid is present either in its free base form or its salt form.

Carriers that that may be used in the pharmaceutical compositions of the present disclosure include, but are not limited to, water, salt solutions (e.g., Ringer's solution and the like), alcohols, oils, gelatins, and carbohydrates such as lactose, amylose or starch, fatty acid esters, methylcellulose, hydroxyethylcellulose, hydroxypropyl cellulose, polyvinyl pyrrolidine, and mixtures or solutions including any of the foregoing. The carrier may be used in combination with a buffering agent.

In some embodiments, the composition of the present disclosure may comprise a carrier at a pH from 5 to 9, or from 6 to 8. In certain embodiments, the composition may comprise a carrier having a neutral pH. In certain embodiments, the pH of the carrier may be at or near physiological pH.

In some embodiments, the pharmaceutical compositions of the present disclosure may include other suitable pharmaceutical additives such tonicity-adjusting agents, preservatives, emulsifiers, sweeteners, flavoring agents, suspending agents, thickening agents, colors, viscosity regulators, stabilizers, and osmo-regulators.

Pharmaceutical compositions in solid form may comprise one or more filling agents, one or more binding agents, one or more lubricants, one or more disintegrants, and/or other conventional excipients such as one or more glidants, for example.

Suitable filling agents include acacia, calcium carbonate, calcium sulfate, calcium sulfate dihydrate, compressible sugar, dibasic calcium phosphate anhydrous (e.g., FUJICALIN, EMCOMPRESS), dibasic calcium phosphate dihydrate, tribasic calcium phosphate, monobasic sodium phosphate, dibasic sodium phosphate, lactose monohydrate, lactose anhydrous, magnesium oxide, magnesium carbonate, silicon dioxide, magnesium aluminum silicate, maltodextrin, mannitol, methyl cellulose, microcrystalline cellulose (e.g., AVICEL PH-101, AVICEL PH-102), powdered cellulose, starches, sorbitol, dextrose, dextrates, dextrin, sucrose, xylitol and mixtures thereof.

Suitable binding agents include various celluloses and cross-linked polyvinylpyrrolidone, microcrystalline cellulose (e.g., AVICEL PH-101, AVICEL PH-102, AVICEL PH-105), or silicified microcrystalline cellulose (e.g., PROSOLV SMCC), for example.

One or more lubricants may be included to reduce friction with and adherence to processing equipment during processing. Examples of suitable lubricants include, but are not limited to, magnesium stearate, calcium stearate, zinc stearate, stearic acid, stearyl alcohol, glyceryl monostearate, sodium stearyl fumarate, talc, glyceryl behenate, sodium benzoate, sodium lauryl sulfate, and the like. When included, the one or more lubricant is generally present in the range of 0.1% to 5%, by weight of the pharmaceutical composition. In some embodiments, the one or more lubricant is generally present in the range of 0.25% to 2%, by weight of the pharmaceutical composition. In certain embodiments, the lubricant is magnesium stearate.

Suitable disintegrants in the practice of the disclosure include natural, modified or pre-gelatinized starch, sodium starch glycolate, sodium carboxymethyl cellulose, calcium carboxymethyl cellulose, croscarmellose sodium, crospovidone, polyvinylpolypyrrolidone, and mixtures thereof.

Glidants are employed to improve flow properties of a powder or granule mixture prior to further processing (such as tablet compression, for example). Suitable glidants that may be employed in the compositions of the present disclosure include, but are not limited to, colloidal silica (e.g., hydrophobic colloidal silica, such as AEROSIL), silica gel, precipitated silica, and the like. When included, the one or more glidant is generally present in the range of 0.1% to 5%, by weight of the pharmaceutical composition. In some embodiments, the one or more glidant is generally present in the range of 0.25% to 2%, by weight of the pharmaceutical composition.

In some cases, a single excipient may provide more than one function. For example, microcrystalline cellulose (when present) can function as both a filling agent and a binding agent. Alternatively, such multi-functional excipients can be used in combination with other functional excipients. (For example, microcrystalline cellulose may be used with other filling agents and/or other binding agents.)

In some embodiments, the pharmaceutical compositions may be in the form of granules, or may be prepared as granules as an intermediate step to forming another oral dosage form, such as a tablet or pellet, or as a fill for a capsule. In some embodiments, the granules may comprise one of more of the pharmaceutically acceptable excipients described above. In certain embodiments, the granules may comprise the ASD in an amount of 50% to 70% by weight of the granule; one or more filling agents in an amount of 20% to 40% by weight of the granule; one or more disintegrants in an amount of 1% to 15% by weight of the granule; and one or more lubricants in an amount of 0.2% to 5% by weight of the granule. In particular embodiments, the granule may comprise the components as set forth in Table 1.

TABLE 1

Components of an exemplary granule formulation in accordance with particular embodiments of the disclosure.

| Component | % By Weight of the Granule |
| --- | --- |
| Nilotinib ASD | 50-70% |
| Mannitol | 20-40% |
| Croscarmellose Sodium | 2-10% |
| Hydrophobic Colloidal Silica | 0.2-5% (optional) |
| Magnesium stearate | 0.2-5% (optional) |

In some embodiments, the pharmaceutical compositions are in the form of a tablet. In certain embodiments, the tablet may comprise the ASD in an amount of 20% to 40% by weight of the tablet; one or more filling agents (such a mannitol and/or microcrystalline cellulose) in an amount of 40% to 70% by weight of the tablet; one or more disintegrants (such as croscarmellose sodium) in an amount of 5% to 15% by weight of the tablet; one or more lubricants and/or glidants (such as hydrophobic colloidal silica and/or magnesium stearate) in an amount of 0.5% to 5% by weight of the tablet; one or more binding agents (such as crospovidone) in an amount of 1% to 10% by weight of the tablet.

Pharmaceutical compositions of the disclosure in the form of a tablet may be prepared using methods known in the art. For example, the nilotinib ASD and the one or more pharmaceutically acceptable additives may be blended to provide a tableting blend by hand or bag blending, or using a suitable device. Examples of suitable blending devices may include, but are not limited to, a tumble blender, v-blender, acoustic blender, paddle mixer, screw mixer, and the like.

Suitable tableting blends may then be compressed into tablets weighing from 100 to 1000 mg using, for example, a manual tablet press or a conventional mechanical tablet press. Compression force is selected to achieve desired mechanical properties of the tablet without compromising performance.

In some embodiments, it may be desirable to form granules as an intermediate step to forming a tableting blend. Granules typically have improved flow, handling, blending, and compression properties relative to ungranulated materials. The granules may be prepared from the ASD particles by processes known in the art, including wet granulation and dry granulation. In some embodiments, a granule blend is formed by dry-blending granule components, and then the granule blend is densified using a roller compactor which typically forms ribbons of material. The ribbons are then reduced in size by milling to form granules.

Wet granulation techniques may also be employed to form granules, provided the solvents and process selected do not alter the properties of the ASD. Improved wetting, disintegrating, dispersing and dissolution properties may be obtained by the inclusion of suitable excipients, as described above.

The granule blend (and accordingly the resulting granules) can include some or all of the components of the tablet. In some embodiments, the granules may comprise one of more of the pharmaceutically acceptable excipients described above. After granulation, the granules can be included into a tableting blend and compressed into tablets, as described above.

The pharmaceutical compositions of the present disclosure may demonstrate a desirable level of physical and/or chemical stability over some suitable period of time, and optionally under accelerated conditions. The stability of the pharmaceutical compositions can be assessed by different measures. For instance, the pharmaceutical compositions may demonstrate chemical stability by having a particular assay value or a particular level of total related substances (e.g., impurities), measured after storage under accelerated conditions over a specified period of time. In some embodiments, the pharmaceutical compositions may be amorphous as assessed using XRD (i.e., no crystalline character detected) after storage under the specified conditions.

In some embodiments, the pharmaceutical compositions may be substantially amorphous as assessed using XRD, after storage under the specified conditions. The storage conditions may be one or more of 25° C./60% RH, or 30° C./65% RH, or 40° C./75% RH. The period of time may be one or more of 1 week, or 2 weeks, or 1 month, or 2 months, or 3 months, or 4 months, or 6 months, or 9 months, or 12 months, or 15 months, or 18 months, or 21 months, or 24 months, or any period of time therebetween.

In some embodiments, pharmaceutical compositions of the present disclosure are "gastric acid-insensitive compositions," as further described below. In some embodiments, pharmaceutical compositions of the present disclosure are "food-insensitive compositions," as further described below. In some embodiments, pharmaceutical compositions of the present disclosure are "improved variability compositions," as further described below.

Treatment of Proliferative Disorders

Aspects of the present disclosure relate to uses of the nilotinib ASDs of the present disclosure, or pharmaceutical compositions comprising the ASDs. In the practice of such embodiments of the present disclosure, the nilotinib ASDs or pharmaceutical compositions may be suitably administered to subjects or to patients.

In some embodiments, the nilotinib ASD or pharmaceutical composition is administered to a subject. The subject in the methods of the present disclosure may be a mammal, which includes, but is not limited to, a human, monkey, cow, hog, sheep, horse, dog, cat, rabbit, rat, and mouse. In certain embodiments, the subject is a human. As used herein, the phrase "healthy human subject" means a human that is generally healthy and is not being treated for the disease or condition for which the pharmaceutically active component (e.g., nilotinib) is generally used for therapy. Selection of suitable healthy human subjects for pharmacokinetic assessment is within the expertise of one skilled in the art of clinical trial design.

In other embodiments, the pharmaceutical composition is administered to a human patient. The human patient may be adult or of a pediatric age, e.g., younger than 17 years old. In certain embodiments, the human patient is 1 year of age or older. As used herein, a "patient" is a subject, particularly a human, who is being treated for a disease or condition for which the pharmaceutically active component (e.g., nilotinib) is generally used for therapy.

An aspect of the present disclosure relates to the use of the nilotinib ASDs of the present disclosure or pharmaceutical compositions of the present disclosure to treat a proliferative disorder. Some embodiments relate to a method of treating a proliferative disorder, the method comprising administering a nilotinib ASD of the present disclosure, or a pharmaceutical composition of the present disclosure, to a patient in need thereof. Some embodiments relate to a use of a nilotinib ASD or a pharmaceutical composition of the present disclosure for treating a proliferative disorder in a patient in need thereof, the use comprising administering the nilotinib ASD or pharmaceutical composition to the patient. Some embodiments relate to a nilotinib ASD or a pharmaceutical composition of the present disclosure for use in treating a proliferative disorder in a patient in need thereof, the use comprising administering the nilotinib ASD or the pharmaceutical composition to the patient. Some embodiments relate to a use of a nilotinib ASD or pharmaceutical composition of the present disclosure in the manufacture of a medicament for treating a proliferative disorder.

In one aspect, the present disclosure relates to a method of treating a proliferative disorder in a patient in need thereof, the method comprising administering a therapeutically effective amount of an ASD of the present disclosure or of a pharmaceutical composition of the present disclosure to the patient.

The proliferative disorder may be cancer. Examples of such proliferative disorders may include, but are not limited to, leukemias such as acute lymphocytic leukemia (or acute lymphoblastic leukemia), acute myeloid leukemia (or acute myelogenous leukemia), chronic lymphocytic leukemia (or chronic lymphoblastic leukemia), chronic myeloid leukemia (or chronic myelogenous leukemia); age-related macular degeneration and diabetic retinopathy, anal and oral cancers, angiosarcoma, basal cell carcinoma and squamous cell carcinoma, bladder cancer, brain cancer, glioma, breast cancer, cancer of the central nervous system, cervical, cervix uteri cancer, choriocarcinoma, colon cancer, gastrointestinal stromal tumor, corpus uteri cancer, esophageal cancer, Ewing's Sarcoma, eye or ocular cancer, head and neck cancer, hemangioendothelioma, hemangiomas and lymphangiogenesis, Kaposi's Sarcoma, larynx cancer, liver cancer, lung cancer, lymphoma, mouth/pharynx cancer, multiple myeloma; cardiac hypertrophy, neuroblastoma, neurofibromatosis, ovary cancer, pancreatic cancer, prostate cancer, rectal cancer, renal cancer, rhabdomyosarcoma, skin melanoma, small cell lung cancer, stomach cancer, testis cancer, throat cancer, tuberous sclerosis, and Wilms Tumor.

In certain embodiments, the proliferative disorder may be Philadelphia chromosome-positive ("Ph+") chronic myeloid leukemia ("CML") in chronic phase. In certain embodiments, the proliferative disorder may be Ph+ CML in accelerated phase. In certain embodiments, the proliferative disorder may be Ph+ CML with resistance or intolerance to prior tyrosine-kinase inhibitor therapy. In certain embodiments, the proliferative disorder may be chronic phase or accelerated phase Ph+ CML with resistance or intolerance to prior therapy that included imatinib.

Nilotinib has further been investigated for use in treating Parkinson's Disease, Huntington's Disease, Alzheimer's Disease, dementia with Lewy bodies, cerebellar ataxia, and other non-proliferative disorders. The compositions, regimens, kits and other embodiments disclosed herein could suitably be employed in the treatment of such non-proliferative conditions.

In the methods and uses of the present disclosure, a therapeutically effective amount of the pharmaceutical composition of the present disclosure will be based on, among other factors, the route of administration, the age and size of the patient, and the proliferative disorder being treated. As used herein, the term "therapeutically effective amount" means that amount that is expected to elicit the biological or medical response that is being sought by a clinician.

In some embodiments, a therapeutically effective amount may be from 50 mg/m$^2$ to 250 mg/m$^2$ of nilotinib, or from 50 mg/m$^2$ to 150 mg/m$^2$ of nilotinib, or from 60 to 120 mg/m$^2$ of nilotinib. In other embodiments, a therapeutically effective amount may be fixed dose. For instance, the fixed dose may be 20 mg to 400 mg, or 30 mg to 300 mg, or 40 mg to 200 mg, per day of nilotinib. In certain embodiments, the fixed dose may be 50 mg, or 55 mg, or 60 mg, or 65 mg, or 70 mg, or 75 mg, or 80 mg, or 85 mg, or 90 mg, or 95 mg or 100 mg, or 110 mg, or 120 mg, or 125 mg, or 130 mg, or 140 mg, or 150 mg, or 160 mg, or 170 mg, or 175 mg, or 180 mg, or 190 mg, or 200 mg, or 210 mg, or 220 mg, or 225 mg, or 230 mg, or 240 mg, or 250 mg, or 260 mg, or 270 mg, or 275 mg, or 280 mg, or 290 mg, or 300 mg, of nilotinib.

Depending on the treatment regimen, the quantity of nilotinib dosed per day may be dosed twice-per-day, or may be dosed all at once (once-daily dosing), based on labeling guidelines or physician's recommendation. In some embodiments, dosing is twice daily at approximately 12-hour intervals.

As described further below, pharmaceutical compositions of the present disclosure may provide enhanced or otherwise desirable bioavailability under a variety of administration conditions. The term "bioavailability" refers to the rate and extent to which an active ingredient is absorbed from a pharmaceutical composition and becomes available at the site of action. In the case of orally administered pharmaceuticals, bioavailability is generally assessed by monitoring a subject's blood plasma over time for the presence of an active ingredient (or suitable surrogate, such as a metabolite) after administration of a pharmaceutical composition, to evaluate the pharmacokinetic profile.

From the pharmacokinetic profile, certain relevant pharmacokinetic parameters can be established. Such pharmacokinetic parameters can include $C_{max}$, $T_{max}$, and/or AUC, for example. $C_{max}$ indicates the maximum observed plasma concentration over the observed time period. $T_{max}$ indicates the time point at which the maximum plasma concentration is observed.

AUC indicates the numerical area-under-the-curve ("AUC") for the concentration-time curve, and can be assessed for a specified time interval 0-t, denoted as $AUC_{0-t}$ (alternatively denoted as $AUC_t$). $AUC_{0-t}$ is generally obtained by numerical integration of the concentration-time curve over the period t=0 to the time "t" (e.g., $AUC_{0-24h}$ or $AUC_{24h}$ indicates the integral over the time period from t=0 to t=24 hours). $AUC_{0-last}$ (alternatively denoted as $AUC_{last}$) indicates the integral from t=0 to the last time point sampled in the observed time period. $AUC_{0-inf}$ (alternatively denoted as $AUC_{inf}$) indicates the integral from t=0 to t="infinity," which is determined by extrapolation of obtained data using commonly employed pharmacokinetic statistical modeling techniques.

Typically, plasma concentration data is log-transformed for analysis. For most pharmacokinetic analyses, data for a number of test subjects is pooled for analysis. When data is pooled, the relevant pharmacokinetic parameters may be expressed as a population geometric mean, in accordance with conventional pharmacokinetic statistical analyses and methods.

Administration of an ASD or pharmaceutical composition of the present disclosure can be characterized by the pharmacokinetic profile, or by the observed or calculated pharmacokinetic parameters resulting from the administration of the ASD or pharmaceutical composition at certain dosages to a subject or patient, under stated administration conditions. By way of example only (and as further described below), administration of the ASD or pharmaceutical composition of the present disclosure under a fasted state or fasting conditions can be characterized by the pharmacokinetic profile resulting from the administration, or by observed pharmacokinetic parameters.

Methods of Administering with Food

An aspect of the present disclosure relates to a method of treating a proliferative disorder in a patient in need thereof, the method comprising administering a therapeutically effective amount of a pharmaceutical composition of the present disclosure to the patient without a food effect.

In another aspect, the present disclosure relates to a method of treating a proliferative disorder in a patient in need thereof, the method comprising administering a therapeutically effective amount of a pharmaceutical composition of the present disclosure to the patient without regard to consumption of food.

In another aspect, the present disclosure relates to a method of treating a proliferative disorder in a patient in need thereof, the method comprising administering a therapeutically effective amount of a pharmaceutical composition of the present disclosure to the patient without regard to whether the patient is in a fasted state or in a fed state.

In yet another aspect, the present disclosure relates to a method of safely delivering nilotinib to a patient in need thereof, comprising step (a), administering a therapeutically effective amount of a pharmaceutical composition of the present disclosure to the patient; and step (b), administering a meal to the patient. In some embodiments, step (b) occurs before step (a). In other embodiments, step (a) occurs before step (b). In some embodiments, steps (a) and (b) occur within less than two hours of each other. In some embodiments, steps (a) and (b) occur within 90 minutes of each other. In some embodiments, steps (a) and (b) occur within one hour of each other. In some embodiments, steps (a) and (b) occur within thirty minutes of each other. In some embodiments, steps (a) and (b) occur within fifteen minutes of each other.

In some embodiments, step (b) occurs less than one hour after step (a). In some embodiments, step (b) occurs less than 30 minutes after step (a). In some embodiments, step (b) occurs less than 15 minutes after step (a).

In some embodiments, step (a) occurs less than two hours after step (b). In some embodiments, step (a) occurs less than 90 minutes after step (b). In some embodiments, step (a) occurs less than one hour after step (b). In some embodiments, step (a) occurs less than 30 minutes after step (b). In some embodiments, step (a) occurs less than 15 minutes after step (b).

In some embodiments, the "meal" is any solid food that is consumed that provides at least 200 calories to the patient or subject. In other embodiments, the meal is any solid food that is consumed that provides at least 400 calories to the patient or subject. In yet other embodiments, the meal is any solid food that is consumed that provides at least 600 calories to the patient or subject. In some embodiments, the meal is a high-fat test meal as described below. In other embodiments, the meal is a low-fat test meal as described below.

In another aspect, the present disclosure relates to a method of delivering a therapeutically effective amount of nilotinib to a patient without regard to a food effect, comprising administering a therapeutically effective amount of a pharmaceutical composition of the present disclosure to the patient.

In a further aspect, the present disclosure relates to a method of delivering a therapeutically effective amount of nilotinib to a patient without regard to consumption of food, comprising administering a therapeutically effective amount of a pharmaceutical composition of the present disclosure to the patient.

In another aspect, the present disclosure relates to a method of delivering a therapeutically effective amount of nilotinib to a patient without regard to whether the patient is in a fed state or in a fasted state, comprising administering a therapeutically effective amount of a pharmaceutical composition of the present disclosure to the patient.

As generally interpreted, "food effect" broadly refers to all aspects of interactions of food on drug dissolution, absorption, distribution, metabolism and elimination. The implications of food effect include changes in bioavailability, rate of on-set, duration of therapeutic effect and incidence and seriousness of side effects. The magnitude of a food effect is generally greatest when the drug product is administered shortly after a meal is ingested. An example of a drug product is with a food effect is TASIGNA, which as described above can produce an increase of AUC and $C_{max}$ by 82% and 112%, respectively, when orally taken 30 minutes after a high-fat meal as compared to levels obtained under fasting conditions.

In practice, a food effect is generally assessed by measuring standard pharmacokinetic parameters observed upon administration of a drug product to a subject in a fasted state, versus the same measurements observed upon administration to the same subject in a fed state. Relevant pharmacokinetic parameters can include AUC, $C_{max}$, and/or $T_{max}$. AUC can be assessed for a specified time interval (such as $AUC_{0-12h}$ or $AUC_{0-24h}$, for example), or as $AUC_{0-last}$ or $AUC_{0-inf}$. Typically, data for a number of test subjects is pooled for analysis.

For further information about food effect studies, refer to "Guidance for Industry: Food-Effect Bioavailability and Fed Bioequivalence Studies" (Center for Drug Evaluation and Research (CDER), Food and Drug Administration (FDA), December 2002), which is hereby incorporated by reference in its entirety. Reference is also made to "Guidance for Industry: Assessing the Effects of Food on Drugs in INDs and NDAs—Clinical Pharmacology Considerations (Draft Guidance)" (CDER, FDA, February 2019), which is hereby incorporated by reference in its entirety.

As used in relation to the methods of the present disclosure the phrase "food effect" refers to a relative difference in one or more of AUC, $C_{max}$, and/or $T_{max}$ for an active substance, when said substance or a formulation thereof (such as a solid dispersion or pharmaceutical composition) is administered orally to a human subject, concomitantly with food or in a fed state, as compared to the measured value for the same parameter when the same formulation is administered to the same subject in a fasted state. The food effect F is calculated as $$F=(Y_{fed}-Y_{fasted})/Y_{fasted}$$

wherein $Y_{fed}$ and $Y_{fasted}$ are the measured values of AUC, $C_{max}$ or $T_{max}$ in the fed and fasted state, respectively.

The phrase "positive food effect" refers to a food effect where the AUC and/or $C_{max}$ is higher when the drug product is administered orally in a fed state than when it is administered in a fasted state. The phrase "negative food effect" refers to a food effect where the AUC and/or $C_{max}$ is lower when the drug product is administered orally in the fed state than when it is administered in the fasted state.

In assessing food effect, data obtained from fasted and fed studies is processed using conventional pharmacokinetic statistical analyses and methods. Fasted and fed studies may be single-dose studies or steady-state studies, as appropriate. Using pooled data from a suitable number of subjects, an absence of food effect is indicated when the 90 percent confidence interval ("CI") for the ratio of population geometric means between fed and fasted administrations, based on log-transformed data, is contained in the equivalence limits of 80% to 125% for $AUC_{0-inf}$ (or $AUC_{0-t}$ when appropriate) and $C_{max}$. On the other hand, an absence of food effect is not established if the 90 percent CI for the ratio of population geometric means between fed and fasted administrations, based on log-transformed data, is not contained in the equivalence limits of 80% to 125% for either $AUC_{0-inf}$ (or $AUC_{0-t}$ when appropriate) or $C_{max}$.

In the methods of the present disclosure, "without a food effect" means that the relative difference is not substantially large, e.g., less than 20%, or less than 15%, or less than 10%, for AUC (which can be, for example, $AUC_{0-24h}$, $AUC_{0-last}$ or $AUC_{0-inf}$) and/or $C_{max}$, for nilotinib when the ASD or pharmaceutical composition of the present disclosure is administered orally, concomitantly with food or in a fed state, as compared to the measured value for the same parameter when the same ASD or pharmaceutical composition is administered in a fasted state. (As used herein, for a relative difference stated as a percentage, each stated range is with respect to the absolute value of that relative difference; i.e., "less than 20%" means that the relative difference F falls in the range −20%<F<+20%.)

In the methods of the present disclosure, "without regard to consumption of food" means that no consideration has to be made whether the ASD or pharmaceutical composition of the present disclosure is being administered to the subject or patient concomitantly with food, or whether the patient or subject is in a fed state or fasted state. The administration will be expected to provide a therapeutically relevant exposure, and will not be expected to cause an unsafe overexposure, regardless of whether the patient or subject is in a fed state or fasted state.

"Therapeutically relevant exposure" as used herein means an exposure that provides $AUC_{0-t}$ (such as $AUC_{0-24h}$) and/or $C_{max}$, in the subject's plasma that would be expected to produce the desired therapeutic effect. One way to determine a similar therapeutic effect is if the $AUC_{0-t}$ or $C_{max}$ is within the 80% to 125% bioequivalence criteria compared to administration of an appropriate strength (determined with reference to the product's labeling) of a conventional immediate-release nilotinib composition to the same subject or subjects, dosed according to its labeled instructions.

As used herein, the phrase "conventional immediate-release nilotinib composition" refers to a commercially available composition comprising nilotinib monohydrochloride monohydrate, generally in crystalline form. The conventional immediate-release nilotinib composition may be in a capsule dosage form. One suitable conventional immediate-release nilotinib composition is TASIGNA IR Capsule (marketed in the United States under New Drug Application 22-068). TASIGNA is understood to contain crystalline nilotinib monohydrochloride monohydrate in an immediate-release capsule formulation.

The phrase "concomitantly with food," as used herein, refers to administration to the subject from 30 minutes after the subject ingests food to 1 hour after the subject ingests food. The phrase "administration in a fed state" (or equivalently "administration under fed conditions") as used herein, refers to administration to the subject from 30 minutes after the subject starts ingesting a meal to 1 hour after complete ingestion of a meal. Similarly, "fed state" or "fed conditions" refers to the condition of a subject 30 minutes after the subject starts ingesting a meal to 1 hour after complete ingestion of a meal.

In some embodiments, the meal is a "high-fat test meal" (or alternatively, "high-fat meal"), which in accordance with FDA's Guidance for Industry (December 2002) referenced above, is a high-fat and high-calorie (approximately 800 to 1000 calories) meal comprising approximately 150 calories from protein, 250 calories from carbohydrate, and 500-600 calories from fat. In other embodiments, the meal is a "low-fat test meal," which in accordance with FDA's Draft Guidance for Industry (February 2019) referenced above, is a lower-calorie (approximately 400 to 500 calories) meal comprising approximately 11-14 grams of fat and approximately 25% calories from fat (with the balance from protein and carbohydrate).

The phrase "administration in a fasted state" (or equivalently "administration under fasting conditions") as used herein refers to administration to the subject at least 2 hours, more suitably at least 4 hours, or more suitably at least 8 hours after the subject's previous meal. Preferably, administration in a fasted state or under fasting conditions follows an overnight fast of at least 10 hours. Similarly, "fasted state" or "fasting conditions," as used herein, refers to the condition in which the subject has not eaten for at least two hours, more suitably at least 4 hours, or more suitably at least 8 hours; or the condition of the subject following an overnight fast of at least 10 hours. Moreover, administration in a fasted state or under fasting conditions may also require continued fasting for at least 1 hour, more suitably at least 2 hours, or more suitably at least 4 hours following the administration.

In certain embodiments, the ASD or pharmaceutical composition is administered without regard to whether the subject is in a fasted state. In certain embodiments, the ASD or pharmaceutical composition is administered without regard to whether the subject is in a fed state. In certain embodiments, the ASD or pharmaceutical composition is administered without regard to whether the subject is in a fasted state or in a fed state. In certain embodiments, the ASD or pharmaceutical composition is administered without regard to a food effect. In certain embodiments, the ASD or pharmaceutical composition is administered concomitantly with food.

Some embodiments relate to a method of delivering nilotinib to a subject without regard to whether the subject is in a fasted state, the method comprising administering to the subject an ASD or pharmaceutical composition according to the disclosure.

Some embodiments relate to a method of delivering nilotinib to a subject without regard to whether the subject is in a fed state, the method comprising administering to the subject an ASD or pharmaceutical composition according to the disclosure.

Some embodiments relate to a method of delivering nilotinib to a subject without regard to whether the subject is in a fasted state or a fed state, the method comprising administering to the subject an ASD or pharmaceutical composition according to the disclosure.

Administration of the ASD or pharmaceutical composition of the present disclosure can be characterized by the pharmacokinetic profile or by calculated pharmacokinetic parameters (such as $C_{max}$ and/or $AUC_{0-t}$, which can be, for example, $AUC_{0-24h}$, $AUC_{0-last}$ or $AUC_{0-inf}$) resulting from the administration of the ASD or pharmaceutical composition at certain dosages to a subject in a fasted state or a fed state.

For example, in some embodiments, administration to a healthy human subject in a fasted state of the ASD or pharmaceutical composition of the disclosure at a dose of 40 mg to 80 mg nilotinib may result in a plasma $C_{max}$ of nilotinib of 501 ng/mL to 621 ng/mL; a plasma $AUC_{0-12h}$ of nilotinib of 3790 ng·h/mL to 4820 ng·h/mL; a plasma $AUC_{0-24h}$ of nilotinib of 5590 ng·h/mL to 7340 ng·h/mL; a plasma $AUC_{0-last}$ of nilotinib of 7610 ng·h/mL to 10600 ng·h/mL; and/or a plasma $AUC_{0-inf}$ of nilotinib of 7760 ng·h/mL to 11000 ng·h/mL.

In some embodiments, administration to a healthy human subject in fed state of the ASD or pharmaceutical composition of the disclosure at a dose of 40 mg to 80 mg nilotinib may result in a plasma $C_{max}$ of nilotinib of 456 ng/mL to 525 ng/mL; a plasma $AUC_{0-12h}$ of nilotinib of 3770 ng·h/mL to 4320 ng·h/mL; a plasma $AUC_{0-24h}$ of nilotinib of 6310 ng·h/mL to 7130 ng·h/mL; a plasma $AUC_{0-last}$ of nilotinib of 9490 ng·h/mL to 11000 ng·h/mL; and/or a plasma $AUC_{0-inf}$ of nilotinib of 9840 ng·h/mL to 11300 ng·h/mL.

Administration of the ASD or pharmaceutical composition of the present disclosure can also be characterized by how the pharmacokinetic profile resulting from administration of the ASD or pharmaceutical composition to a subject in a fed state compares to the pharmacokinetic profile resulting from administration of the ASD or pharmaceutical composition to a subject in a fasted state. As an example, for some embodiments, administration of the ASD or pharmaceutical composition of the present disclosure to a subject in a fed state and in a fasted state may result in a relative difference in the plasma exposure of nilotinib between the fed state and the fasted state of less than 50%, less than 40%, or less than 35%, or less than 30%, or less than 25%, or less than 20%, or less than 15%, or less than 10%, or less than 5%. Exposure may be expressed as $AUC_{0-12h}$, $AUC_{0-24h}$, $AUC_{0-last}$, or $AUC_{0-inf}$, for example. Exposure can be demonstrated for an individual subject, or alternatively for a suitable number of subjects (n>1). When comparing a number of subjects for which data is pooled, the exposure may be expressed as a population geometric mean, in accordance with conventional pharmacokinetic statistical analyses and methods.

In certain embodiments, administration of the ASD or pharmaceutical composition of the present disclosure to a subject in a fed state may result in plasma $AUC_{0-12h}$ of nilotinib that is less than the plasma $AUC_{0-12h}$ of nilotinib that may result from administration of the pharmaceutical composition to the subject in a fasted state. In certain embodiments, administration of the ASD or pharmaceutical composition of the present disclosure to a subject in a fed state may result in plasma $AUC_{0-12h}$ of nilotinib that is within 25%, or within 20%, of the plasma $AUC_{0-12h}$ of nilotinib that may result from administration of the pharmaceutical composition to the subject in a fasted state. Plasma $AUC_{0-12h}$ can be for an individual subject, or a geometric mean from a number of subjects.

In certain embodiments, administration of the ASD or pharmaceutical composition of the present disclosure to a subject in a fed state may result in plasma $AUC_{0-24h}$ of nilotinib that is less than the plasma $AUC_{0-24h}$ of nilotinib that may result from administration of the pharmaceutical composition to the subject in a fasted state. In certain embodiments, administration of the ASD or pharmaceutical composition of the present disclosure to a subject in a fed state may result in plasma $AUC_{0-24h}$ of nilotinib that is within 50%, or within 40%, or within 35%, or within 30%, or within 25%, or within 20%, or within 15%, or within 10%, of the plasma $AUC_{0-24h}$ of nilotinib that may result from administration of the pharmaceutical composition to the subject in a fasted state. Plasma $AUC_{0-24h}$ can be for an individual subject, or a geometric mean from a number of subjects.

In certain embodiments, administration of the ASD or pharmaceutical composition of the present disclosure to a subject in a fed state may result in plasma $AUC_{0-last}$ of nilotinib that is less than the plasma $AUC_{0-last}$ of nilotinib that may result from administration of the pharmaceutical composition to the subject in a fasted state. In certain embodiments, administration of the ASD or pharmaceutical composition of the present disclosure to a subject in a fed state may result in plasma $AUC_{0-last}$ of nilotinib that is within 50%, or within 40%, or within 35%, or within 30%, or within 25%, or within 20%, or within 15%, or within 10%, of the plasma $AUC_{0-last}$ of nilotinib that may result from administration of the pharmaceutical composition to the subject in a fasted state. Plasma $AUC_{0-last}$ can be for an individual subject, or a geometric mean from a number of subjects.

In certain embodiments, administration of the ASD or pharmaceutical composition of the present disclosure to a subject in a fed state may result in plasma $AUC_{0-inf}$ of nilotinib that is less than the plasma $AUC_{0-inf}$ of nilotinib that may result from administration of the pharmaceutical composition to the subject in a fasted state. In certain embodiments, administration of the ASD or pharmaceutical composition of the present disclosure to a subject in a fed state may result in plasma $AUC_{0-inf}$ of nilotinib that is within 50%, or within 40%, or within 35%, or within 30%, or within 25%, or within 20%, or within 15%, or within 10%, of the plasma $AUC_{0-inf}$ of nilotinib that may result from administration of the pharmaceutical composition to the subject in a fasted state. Plasma $AUC_{0-inf}$ can be for an individual subject, or a geometric mean from a number of subjects.

For some embodiments, administration of an ASD or pharmaceutical composition of the present disclosure to a subject in a fed state and in a fasted state may result in a relative difference in the plasma $C_{max}$ of nilotinib between the fed state and the fasted state of less than 50%, less than 30%, or less than 25%, or less than 20%, or less than 15%, or less than 10%, or less than 5%. In certain embodiments, administration of the ASD or pharmaceutical composition of the present disclosure to a subject in a fed state may result in plasma $C_{max}$ of nilotinib that is less than the $C_{max}$ of nilotinib that may result from administration of the ASD or pharmaceutical composition of the present disclosure to the subject in a fasted state. $C_{max}$ can be demonstrated for an individual subject, or alternatively for a suitable number of subjects (n>1). When comparing a number of subjects for which data is pooled, the $C_{max}$ may be expressed as a population geometric mean, in accordance with conventional pharmacokinetic statistical analyses and methods.

In yet other embodiments, administration of the ASD or pharmaceutical composition to a subject in a fed state provides an exposure of nilotinib that is similar to the exposure resulting from administration of the pharmaceutical composition to the subject in a fasted state. Exposure may be expressed as $AUC_{0-12h}$, $AUC_{0-24h}$, $AUC_{0-last}$, or $AUC_{0-inf}$, for example; exposure can be for an individual subject, or a geometric mean from a number of subjects.

In some embodiments, administration of the ASD or pharmaceutical composition to a subject in a fed state provides a plasma $C_{max}$ of nilotinib that is similar to the plasma $C_{max}$ of nilotinib resulting from administration of the ASD or pharmaceutical composition to the subject in a fasted state. Plasma $C_{max}$ can be for an individual subject, or a geometric mean from a number of subjects.

As used herein in this context, "similar" exposure means a relative difference in the plasma exposure of nilotinib between the fed state and the fasted state of less than 25%, or less than 20%, or less than 15%, or less than 10%, or less than 5%; and "similar" $C_{max}$ likewise means a relative difference in the plasma $C_{max}$ of nilotinib between the fed state and the fasted state of less than 25%, or less than 20%, or less than 15%, or less than 10%, or less than 5% (each stated percentage is understood to be an absolute value; i.e., "less than 20%" means that the relative difference F falls in the range −20%<F<+20%).

In some embodiments, the pharmaceutical composition of the present disclosure may provide a plasma $C_{max}$ of nilotinib of 501 ng/mL to 621 ng/mL resulting from administration of a dose of 40 mg to 80 mg nilotinib to a healthy human subject in a fasted state, and may provide a plasma $C_{max}$ of nilotinib of 456 ng/mL to 525 ng/mL resulting from administration of a dose of 40 mg to 80 mg nilotinib to a healthy human subject in fed state.

In some embodiments, the pharmaceutical composition of the present disclosure may provide a plasma $AUC_{0-12h}$ of nilotinib of 3790 ng·h/mL to 4820 ng·h/mL resulting from administration of a dose of 40 mg to 80 mg nilotinib to a healthy human subject in a fasted state, and may provide a plasma $AUC_{0-12h}$ of nilotinib of 3770 ng·h/mL to 4320 ng·h/mL resulting from administration of a dose of 40 mg to 80 mg nilotinib to a healthy human subject in fed state.

In some embodiments, the pharmaceutical composition of the present disclosure may provide a plasma $AUC_{0-24h}$ of nilotinib of 5590 ng·h/mL to 7340 ng·h/mL resulting from administration of a dose of 40 mg to 80 mg nilotinib to a healthy human subject in a fasted state, and may provide a plasma $AUC_{0-24h}$ of nilotinib of 6310 ng·h/mL to 7130 ng·h/mL resulting from administration of a dose of 40 mg to 80 mg nilotinib to a healthy human subject in fed state.

In some embodiments, the pharmaceutical composition of the present disclosure may provide a plasma $AUC_{0-last}$ of nilotinib of 7610 ng·h/mL to 10600 ng·h/mL resulting from administration of a dose of 40 mg to 80 mg nilotinib to a healthy human subject in a fasted state, and may provide a plasma $AUC_{0-last}$ of nilotinib of 9490 ng·h/mL to 11000 ng·h/mL resulting from administration of a dose of 40 mg to 80 mg nilotinib to a healthy human subject in fed state.

In some embodiments, the pharmaceutical composition of the present disclosure may provide a plasma $AUC_{0-inf}$ of nilotinib of 7760 ng·h/mL to 11000 ng·h/mL resulting from administration of a dose of 40 mg to 80 mg nilotinib to a healthy human subject in a fasted state, and may provide a plasma $AUC_{0-inf}$ of nilotinib of 9840 ng·h/mL to 11300 ng·h/mL resulting from administration of a dose of 40 mg to 80 mg nilotinib to a healthy human subject in fed state.

As used herein, the phrase "food-insensitive composition" indicates a pharmaceutical composition of the present disclosure that can be administered without regard to the patient's or subject's fed or fasted state. A food-insensitive composition provides a therapeutically relevant exposure to the patient or subject regardless of whether the patient or subject has recently ingested a meal, or whether the patient or subject ingests a meal shortly after administration of the pharmaceutical composition, or whether the patient or subject was in a fasted state at the time of administration and remains in the fasted state for some time following administration.

Methods of Administering at Reduced Dosage

In addition, administration of the ASD or pharmaceutical composition of the present disclosure can be characterized by how the pharmacokinetic profile resulting from administration of the ASD or pharmaceutical composition compares to the pharmacokinetic profile resulting from administration of a conventional immediate-release nilotinib composition.

For instance, in some embodiments, administration of an ASD or pharmaceutical composition of the present disclosure may result in a pharmacokinetic profile that is comparable to the pharmacokinetic profile obtained by orally administering a conventional immediate-release nilotinib formulation, but administered at a fraction of the dosage. For this comparison, administration must be done in a fasted state, since TASIGNA should only be administered in a fasted state.

For embodiments of the disclosure that can be administered at a fraction of the dosage as compared to the dosage required when administering a conventional immediate-release nilotinib composition, it can be reasoned that the inventive formulation is inherently safer than the corresponding conventional immediate-release nilotinib composition. By decreasing the required dosage while still providing an efficacious exposure to the patient, the risks of overexposure are reduced. Overexposure to nilotinib is associated with the risk of QT prolongation discussed above, which is currently the subject of a "black box warning" on the TASIGNA label. The risk of overexposure affects the entire patient population treated with nilotinib. As such, a reduced dosage inherently decreases the risk of sudden death in the patient population, since QT prolongation is reported to cause sudden cardiac death in approximately one out of every 300 TASIGNA patients.

In addition to reducing the overall risk of overexposure, the formulations of the disclosure may limit risk associated with an undesirably high $C_{max}$. For certain risks such as QT prolongation, $C_{max}$ may in fact be the more relevant pharmacokinetic parameter. A sizable increase in $C_{max}$, such as between fasted and fed states, may be highly undesirable and potentially unsafe. In some embodiments, the formulations of the disclosure reduce or eliminate the possibility that a patient may experience an undesirably high $C_{max}$.

With respect to the respective pharmacokinetic profiles, by "comparable," it is meant that the administration of the ASD or the pharmaceutical composition of the disclosure to the subject may provide $AUC_{0-t}$ (such as $AUC_{0-24h}$ or $AUC_{0-inf}$) or $C_{max}$ in the subject's plasma that are within the 80% to 125% bioequivalence criteria compared to administration of the immediate-release crystalline nilotinib formulation to the same subject, dosed according to its labeled instructions.

As used herein, "fraction of the dosage" may mean that the dose of nilotinib in the ASD or pharmaceutical composition of the present disclosure may be 80% less, or 75% less, or 70% less, or 65% less, or 60% less, or 55% less, or 50% less, or 45% less, or 40% less, or 35% less, or 30% less, or 25% less, or 20% less, as compared to the labeled dosage of the immediate-release crystalline nilotinib formulation.

By way of example only, a pharmaceutical composition of the present disclosure containing approximately 50 mg nilotinib free base may provide a pharmacokinetic profile that is comparable to the pharmacokinetic profile obtained by orally administering an immediate-release crystalline nilotinib formulation labeled to contain 200 mg of nilotinib (such as 200 mg TASIGNA IR Capsule). In this example, the dose of nilotinib in the inventive pharmaceutical composition is 75% less than the dosage of the immediate-release crystalline nilotinib formulation.

In some embodiments, the dose of nilotinib in the ASD or pharmaceutical composition of the present disclosure is 80% less, or 75% less, or 70% less, or 65% less, or 60% less, or 55% less, or 50% less, as compared to the labeled dosage of the immediate-release crystalline nilotinib formulation.

For some embodiments, administration of the ASD or pharmaceutical composition of the present disclosure to a subject in a fasted state may result in plasma exposure of nilotinib that is within 20%, or within 15%, or within 10%, of the plasma exposure of nilotinib that may result from administration to a subject in a fasted state of an immediate-release crystalline nilotinib formulation, where the ASD or pharmaceutical composition is administered at a fraction of the dosage. In certain embodiments, administration of the ASD or pharmaceutical composition of the present disclosure to a subject in a fasted state may result in plasma exposure of nilotinib that is greater than the plasma exposure of nilotinib that that may result from administration to a subject in a fasted state of an immediate-release crystalline nilotinib formulation, where the ASD or pharmaceutical composition is administered at a fraction of the dosage. Exposure may be expressed as $AUC_{0-12h}$, $AUC_{0-24h}$, $AUC_{0-last}$, or $AUC_{0-inf}$ for example. Exposure can be for an individual subject, or a geometric mean from a number of subjects.

For some embodiments, administration of the ASD or pharmaceutical composition of the present disclosure to a subject in a fasted state may result in plasma $C_{max}$ of nilotinib that is within 20%, or within 15%, or within 10%, of the plasma $C_{max}$ of nilotinib that may result from administration to a subject in a fasted state of an immediate-release crystalline nilotinib formulation, where the ASD or pharmaceutical composition is administered at a fraction of the dosage. In certain embodiments, administration of the ASD or pharmaceutical composition of the present disclosure to a subject in a fasted state may result in plasma $C_{max}$ of nilotinib that is greater than the plasma $C_{max}$ of nilotinib that may result from administration to a subject in a fasted state of an immediate-release crystalline nilotinib formulation, where the ASD or pharmaceutical composition is administered at a fraction of the dosage. $C_{max}$ can be for an individual subject, or a geometric mean from a number of subjects.

In the practice of some embodiments, the dosage of immediate-release crystalline nilotinib formulation is a multiple of the dose of the nilotinib contained in the pharmaceutical composition according to the disclosure. In some embodiments, the immediate-release crystalline nilotinib formulation may comprise at least two times, at least three times, at least four times, or at least five times, the amount of nilotinib as the pharmaceutical composition according to the disclosure. In some embodiments, the immediate-release crystalline nilotinib formulation may comprise from two times to five times the amount of nilotinib as the pharmaceutical composition according to the disclosure. In some embodiments, the immediate-release crystalline nilotinib formulation may comprise from two times to four times the amount of nilotinib as the pharmaceutical composition according to the disclosure.

In some embodiments, administration of the ASD or pharmaceutical composition of the present disclosure to a subject in a fasted state may result in plasma $AUC_{0-12h}$ of nilotinib that is greater than the plasma $AUC_{0-12h}$ of nilotinib that may result from the administration of an immediate-release crystalline nilotinib formulation that has four times, or three times, or twice, the amount of nilotinib as the ASD or pharmaceutical composition. Plasma $AUC_{0-12h}$ can be for an individual subject, or a geometric mean from a number of subjects.

In some embodiments, administration of the ASD or pharmaceutical composition of the present disclosure to a subject in a fasted state may result in plasma $AUC_{0-12h}$ of nilotinib that is within 20%, or within 15%, of the plasma $AUC_{0-12h}$ of nilotinib that may result from the administration of an immediate-release crystalline nilotinib formulation that has four times, or three times, or twice, the amount of nilotinib as the ASD or pharmaceutical composition. Plasma $AUC_{0-12h}$ can be for an individual subject, or a geometric mean from a number of subjects.

In some embodiments, administration of the ASD or pharmaceutical composition of the present disclosure to a subject in a fasted state may result in plasma $AUC_{0-24h}$ of nilotinib that is greater than the plasma $AUC_{0-24h}$ of nilotinib that may result from the administration of an immediate-release crystalline nilotinib formulation that has four times, or three times, or twice, the amount of nilotinib as the ASD or pharmaceutical composition. Plasma $AUC_{0-24h}$ can be for an individual subject, or a geometric mean from a number of subjects.

In some embodiments, administration of the ASD or pharmaceutical composition of the present disclosure to a subject in a fasted state may result in plasma $AUC_{0-24h}$ of nilotinib that is within 20%, or within 15%, of the plasma $AUC_{0-24h}$ of nilotinib that may result from the administration of an immediate-release crystalline nilotinib formulation that has four times, or three times, or twice, the amount of nilotinib as the ASD or pharmaceutical composition. Plasma $AUC_{0-24h}$ can be for an individual subject, or a geometric mean from a number of subjects.

In some embodiments, administration of the ASD or pharmaceutical composition of the present disclosure to a subject in a fasted state may result in plasma $AUC_{0-last}$ of nilotinib that is within 20%, or within 15%, of the plasma $AUC_{0-last}$ of nilotinib that may result from the administration of an immediate-release crystalline nilotinib formulation that has four times, or three times, or twice, the amount of nilotinib as the ASD or pharmaceutical composition. Plasma $AUC_{0-last}$ can be for an individual subject, or a geometric mean from a number of subjects.

In some embodiments, administration of the ASD or pharmaceutical composition of the present disclosure to a subject in a fasted state may result in plasma $AUC_{0-inf}$ of nilotinib that is within 25%, or within 20%, of the plasma $AUC_{0-inf}$ of nilotinib that may result from the administration of an immediate-release crystalline nilotinib formulation that has four times, or three times, or twice, the amount of nilotinib as the ASD or pharmaceutical composition. Plasma $AUC_{0-inf}$ can be for an individual subject, or a geometric mean from a number of subjects.

In some embodiments, administration of the ASD or pharmaceutical composition of the present disclosure to a subject in a fasted state may result in plasma $C_{max}$ of nilotinib that is greater than the plasma $C_{max}$ of nilotinib that may result from the administration of an immediate-release crystalline nilotinib formulation that has four times, or three times, or twice, the amount of nilotinib as the ASD or pharmaceutical composition. Plasma $C_{max}$ can be for an individual subject, or a geometric mean from a number of subjects.

In some embodiments, administration of the ASD or pharmaceutical composition of the present disclosure to a subject in a fasted state may result in plasma $C_{max}$ of nilotinib that is within 25%, or within 20%, of the plasma $C_{max}$ of nilotinib that may result from the administration of an immediate-release crystalline nilotinib formulation that has four times, or three times, or twice, the amount of nilotinib as the ASD or pharmaceutical composition. Plasma $C_{max}$ can be for an individual subject, or a geometric mean from a number of subjects.

In yet other embodiments, administration of an ASD or pharmaceutical composition of the present disclosure to a subject in a fasted state provides an exposure of nilotinib that is similar to the exposure resulting from administration of an immediate-release crystalline nilotinib formulation, but administered at a fraction of the dosage. Exposure may be expressed as $AUC_{0-12h}$, $AUC_{0-24h}$, $AUC_{0-last}$, or $AUC_{0-inf}$, for example; exposure can be for an individual subject, or a geometric mean from a number of subjects.

In yet other embodiments, administration of an ASD or pharmaceutical composition of the present disclosure to a subject in a fasted state provides plasma $C_{max}$ of nilotinib that is similar to the plasma $C_{max}$ of nilotinib resulting from administration of an immediate-release crystalline nilotinib formulation, but administered at a fraction of the dosage. Plasma $C_{max}$ can be for an individual subject, or a geometric mean from a number of subjects.

In yet other embodiments, administration of an ASD or pharmaceutical composition of the present disclosure to a subject in a fed state provides an exposure of nilotinib that is similar to the exposure resulting from administration of an immediate-release crystalline nilotinib formulation to the subject in a fasted state, but administered at a fraction of the dosage. Exposure may be expressed as $AUC_{0-12h}$, $AUC_{0-24h}$, $AUC_{0-last}$, or $AUC_{0-inf}$, for example; exposure can be for an individual subject, or a geometric mean from a number of subjects.

In yet other embodiments, administration of an ASD or pharmaceutical composition of the present disclosure to a subject in a fed state provides plasma $C_{max}$ of nilotinib that is similar to the plasma $C_{max}$ of nilotinib resulting from administration of an immediate-release crystalline nilotinib formulation to the subject in a fasted state, but administered at a fraction of the dosage. Plasma $C_{max}$ can be for an individual subject, or a geometric mean from a number of subjects.

As used herein in this context, "similar" exposure means a relative difference in the plasma exposure of nilotinib between administration of the pharmaceutical composition and administration of the immediate-release crystalline nilotinib formulation, of less than 25%, or less than 20%, or less than 15%, or less than 10%, or less than 5%; and "similar $C_{max}$" means a relative difference in the plasma $C_{max}$ of nilotinib between administration of the pharmaceutical composition and administration of the immediate-release crystalline nilotinib formulation, of less than 25%, or less than 20%, or less than 15%, or less than 10%, or less than 5% (each stated percentage is understood to be an absolute value; i.e., "less than 20%" means that the relative difference F falls in the range −20%<F<+20%).

Effective Bioequivalence to Reference Composition

In another aspect, the disclosure provides pharmaceutical compositions that are effectively bioequivalent to a suitable reference composition when administered to healthy human subjects in a fasted state, but at a lower molar dose of the active ingredient as compared to the reference composition. In some embodiments, the reference composition is a conventional immediate-release nilotinib composition comprising nilotinib monohydrochloride monohydrate. In some embodiments, the reference composition is TASIGNA IR Capsule.

Pertaining to bioequivalence studies, FDA has published "Guidance for Industry: Bioequivalence Studies with Pharmacokinetic Endpoints for Drugs Submitted Under an ANDA (Draft Guidance)" (CDER, FDA, December 2013), which is hereby incorporated by reference in its entirety. Pertaining to statistical methods for determining bioequivalence, FDA has published "Guidance for Industry: Statistical Approaches to Establishing Bioequivalence" (CDER, FDA, January 2001), which is hereby incorporated by reference in its entirety.

Per FDA guidelines, a drug product (a "test composition") is bioequivalent to a reference drug product (the "reference composition") when the rate and extent of absorption of the drug substance (i.e., the active ingredient) from the test composition do not show a significant difference from the rate and extent of absorption of the drug substance when administered using the reference composition, under similar experimental conditions. For many drug substances that are orally bioavailable, including nilotinib, the preferred method for assessing bioequivalence is by assessing the pharmacokinetic profile attained upon oral administration of the test and reference compositions.

The bioequivalence assessment frequently relies on pharmacokinetic endpoints such as $C_{max}$ and AUC that are reflective of rate and extent of absorption, respectively. Generally speaking, using pooled data from a suitable number of subjects, bioequivalence between the test composition and reference composition is established when the 90 percent confidence interval ("CI") for the ratio of population geometric means between test composition and reference composition administrations, based on log-transformed data, is contained in the equivalence limits of 80% to 125% for both $AUC_{0-inf}$ (or $AUC_{0-t}$ when appropriate) and $C_{max}$. On the other hand, bioequivalence is not established if the 90 percent CI for the ratio of population geometric means between test composition and reference composition administrations, based on log-transformed data, is not contained in the equivalence limits of 80% to 125% for either $AUC_{0-inf}$ (or $AUC_{0-t}$ when appropriate) or $C_{max}$.

As discussed above, a pharmacokinetic profile is assessed by monitoring the subject's blood plasma over time for the presence of the active ingredient (or in some cases a suitable surrogate, such as a metabolite) after administration of the pharmaceutical composition of interest. Per the FDA draft guidance for nilotinib hydrochloride monohydrate compositions, the plasma analyte of interest is nilotinib. Nilotinib is also the relevant plasma analyte for the pharmaceutical compositions of the present disclosure.

Depending on the nature of the drug substance and the reference and test compositions, the required showing may require single-dose or multiple-dose studies. The most recent FDA guidance document (draft guidance, July 2014) on bioequivalence studies pertaining to nilotinib hydrochloride monohydrate oral capsules (200 mg) recommend a single-dose two-way crossover study under fasting conditions.

Per FDA guidelines, a test composition can only be bioequivalent when dosed at the same molar dose of the active ingredient as the reference composition. As discussed above, however, administration of an ASD or pharmaceutical composition of the present disclosure may result in a pharmacokinetic profile that is comparable to the pharmacokinetic profile obtained by orally administering a conventional immediate-release nilotinib formulation, but administered at a fraction of the dosage. For such embodiments, a more appropriate comparison is to assess the relative bioavailability when the test composition is dosed at a fraction of the corresponding molar dose of the chosen reference composition. As used herein, the phrases "effectively bioequivalent" and "effective bioequivalence" are used to refer to the situation where a test composition and reference composition meet stated bioequivalence criteria, but at different molar doses.

In one embodiment, the disclosure provides a pharmaceutical composition comprising 100 mg nilotinib in an oral dosage form; wherein, when the oral dosage form is administered to a healthy human subjects in a fasted state, achieves an $AUC_{0-inf}$ and $C_{max}$ within the 80% to 125% bioequivalence criteria as compared to $AUC_{0-inf}$ and $C_{max}$ achieved upon administration of a reference composition, wherein the reference composition is a conventional immediate-release nilotinib composition comprising 200 mg nilotinib monohydrochloride monohydrate.

In another embodiment, the disclosure provides a pharmaceutical composition comprising an amorphous solid dispersion including nilotinib and one or more polymers, wherein the composition is contained in an oral dosage form comprising 100 mg nilotinib; and wherein, when the oral dosage form is administered to a healthy human subjects in a fasted state, achieves an $AUC_{0-inf}$ and $C_{max}$ within the 80% to 125% bioequivalence criteria as compared to $AUC_{0-inf}$ and $C_{max}$ achieved upon administration of a reference composition, wherein the reference composition is conventional immediate-release nilotinib composition comprising 200 mg nilotinib monohydrochloride monohydrate.

In another embodiment, the disclosure provides a pharmaceutical composition comprising 100 mg nilotinib in an oral dosage form, wherein the pharmaceutical composition is effectively bioequivalent under fasting conditions to a reference composition which is a conventional immediate-release nilotinib composition comprising 200 mg nilotinib monohydrochloride monohydrate; where effective bioequivalence is established by: (a) a 90% confidence interval for AUC which is between 80% and 125%; and (b) a 90% confidence interval for $C_{max}$, which is between 80% and 125%.

In another aspect, the disclosure provides pharmaceutical compositions that meet one or more bioequivalence criteria when administered to healthy human subjects in either a fasted or fed state, as compared to a suitable reference composition when administered to healthy human subjects in a fasted state, but at a lower molar dose of the active ingredient as compared to the reference composition.

In any of the foregoing embodiments, the AUC can be $AUC_{0-24h}$, $AUC_{0-last}$, or $AUC_{0-inf}$, for example, as appropriate.

In some embodiments, the reference composition is a conventional immediate-release nilotinib composition comprising nilotinib monohydrochloride monohydrate. In some embodiments, the reference composition comprises crystalline nilotinib monohydrochloride monohydrate. In some embodiments, the reference composition is in capsule form. In some embodiments, the reference composition is TASIGNA IR Capsule.

Methods of Co-Administering with a Gastric Acid-Reducing Agent

Other embodiments of the present disclosure relate to the use of the nilotinib ASDs and the pharmaceutical compositions of the present disclosure with a gastric acid-reducing agent.

In one aspect, the present disclosure relates to a method of delivering nilotinib concurrently with a gastric acid-reducing agent to a patient in need thereof, comprising co-administering to the patient (a) a therapeutically effective amount of a pharmaceutical composition of the present disclosure, and (b) a therapeutically effective amount of the gastric acid-reducing agent.

In another aspect, the present disclosure relates to a method of treating a patient who has a proliferative disorder and is suffering from condition caused by the overproduction of stomach acid or exacerbated by stomach acid, the method comprising co-administering to the patient (a) a therapeutically effective amount of a pharmaceutical composition of the present disclosure, and (b) a therapeutically effective amount of a gastric acid-reducing agent.

In yet another aspect, the present disclosure relates to a method of delivering a therapeutically effective amount of nilotinib to a patient without regard to whether the patient is concurrently administered a gastric acid-reducing agent, comprising administering a therapeutically effective amount of a pharmaceutical composition of the present disclosure to the patient.

"Gastric acid-reducing agent" refers herein to any agent that acts to significantly reduce the amount of acid in a subject's stomach. Acid reduction can be due to suppression or blocking of acid secretion, or by neutralization of stomach acid. Examples of gastric acid-reducing agents include, but are not limited to, proton pump inhibitors, histamine-2 receptor antagonists (or $H_2$ antagonists), and antacids.

Proton pump inhibitors reduce stomach acid production by blocking the hydrogen/potassium adenosine triphosphatase enzyme (i.e., the gastric proton pump) of the parietal cells, which are the epithelial cells that secrete stomach acid. Examples of proton pump inhibitors include, but are not limited to, rabeprazole, esomeprazole, lansoprazole, omeprazole, pantoprazole, and dexlansoprazole.

$H_2$ antagonists block histamine from binding to the $H_2$ receptors of parietal cells, thereby suppressing both the normal secretion and meal-stimulated secretion of acid by parietal cells. Examples of $H_2$ antagonists include, but are not limited to, famotidine, cimetidine, nizatidine, and ranitidine.

Antacids contain alkaline ions that chemically neutralize stomach gastric acid. Examples of antacids include, but are not limited to, aluminum hydroxide, magnesium hydroxide, sodium citrate, sodium carbonate, sodium bicarbonate, calcium carbonate, and magnesium trisilicate.

The gastric acid-reducing agent may be administered in accordance with the dosing information that is known in the art for the agent, or according to a physician's instructions. A "therapeutically effective amount" of the gastric acid-reducing agent may be the amount set forth in the dosing information that is known in the art for the gastric acid-reducing agent, or according to a physician's instructions. A "standard dosage" is a dosage in accordance with a product's labeled instructions. In particular, a standard dosage is appropriate for gastric acid-reducing agents that are available over-the-counter (i.e., without a physician's prescription), such as most antacids, certain $H_2$ antagonists, and certain proton pump inhibitors.

As used herein, a condition caused by the overproduction of stomach acid or exacerbated by stomach acid may be any condition that can be treated by reducing the amount of acid or the acidity in the subject's stomach. Examples of such a condition include, but are not limited to, dyspepsia (i.e., indigestion), gastroesophageal reflux disease, duodenal or stomach ulcers, erosive esophagitis, stress gastritis, Barrett's esophagus, and gastrinomas.

As used herein, "co-administration" (or "co-administered") refers to the administration of two or more therapeutic agents within a relevant period of time (such as one day, or 12 hours, or 8 hours, or 6 hours, for example), such that consideration must be given to whether the administration of one of the therapeutic agents may affect the absorption or efficacy of the other. Such administration may be for the treatment of two or more conditions simultaneously, such as, by way of example only, a patient requiring treatment for a proliferative disorder as described herein with nilotinib as a therapeutic agent, while also being treated for another condition, such as acid reflux or ulcers, with a second therapeutic agent such as a gastric acid-reducing agent (e.g., a proton pump inhibitor). Since both therapeutic agents are dosed at least once daily, the two therapeutic agents are "co-administered," and consideration must be given to whether the administration of one of the therapeutic agents may affect the absorption or efficacy of the other.

In the context of the present disclosure, the phrase "can be co-administered" means that the two (or more) therapeutic agents of interest can be co-administered without a detrimental reduction in the exposure of nilotinib. "Without a detrimental reduction" indicates that the realized exposure would be comparable to the exposure realized when the gastric acid-reducing agent is not co-administered. Any difference in the realized exposure would be insubstantial and/or therapeutically inconsequential. In contrast, when a detrimental reduction in exposure would be realized, then co-administration should be avoided. A "detrimental reduction" means a substantial and material reduction in the realized exposure. By way of example, if the realized exposure would be less than or equal to a level recognized as a sub-therapeutic exposure, then the co-administration would result in a detrimental reduction in exposure.

As used herein, the phrase "gastric acid-insensitive composition" indicates a pharmaceutical composition of the present disclosure that can be administered without regard to the patient or subject's gastric pH. A gastric acid-insensitive composition provides a therapeutically relevant exposure to the patient or subject across a range of gastric pH values. Accordingly, a gastric acid-insensitive composition can be administered whether or not the patient or subject has ingested a gastric acid-reducing agent, or whether or not the patient has a condition that causes elevated gastric pH (as further discussed below).

Embodiments of the disclosure relate to administering a gastric acid-reducing agent shortly before, concurrently with, or shortly after the nilotinib ASDs or pharmaceutical compositions of the disclosure. The term "shortly before" as used herein may mean that a gastric acid-reducing agent was administered to the subject 10 hours or less, or 8 hours or less, or 6 hours or less, or 5 hours or less, or 4 hours or less, or 3 hours or less, or 2 hours or less, or 1 hour or less, or 45 minutes or less, or 30 minutes or less, or 15 minutes or less, prior to the administration of the pharmaceutical composition of the disclosure. The term "concurrently" or "concomitantly" as used herein may mean that a gastric acid-reducing agent was administered to the subject within 30 minutes or less, or within 20 minutes or less, or within 15 minutes or less, or within 10 minutes or less, or within 5 minutes or less, or within 4 minutes or less, or within 3 minutes or less, or within 2 minutes or less, or within 1 minute or less, or simultaneously, of the administration of the pharmaceutical composition. The term "shortly after" as used herein means that a gastric acid-reducing agent was administered to the subject 6 hours or less, or 5 hours or less, or 4 hours or less, or 3 hours or less, or 2 hours or less, or 1 hour or less, or 45 minutes or less, or 30 minutes or less, or 15 minutes or less, after the administration of the pharmaceutical composition.

In some embodiments, administration of an ASD or pharmaceutical composition of the present disclosure to a subject who was concurrently, shortly before, or shortly after administered a gastric acid-reducing agent exhibits a pharmacokinetic profile of nilotinib that is similar to the pharmacokinetic profile resulting from administration of the ASD or pharmaceutical composition to a subject who was not concurrently, shortly before, or shortly after administered a gastric acid-reducing agent. In certain embodiments, single administration of the ASD or pharmaceutical composition to a subject who was concurrently, shortly before, or shortly after administered a gastric acid-reducing agent results in an AUC of nilotinib that is within 50%, or within 40%, or within 30%, of the AUC of nilotinib that results from administration of the ASD or pharmaceutical composition without being administered the gastric acid-reducing agent concurrently, shortly before, or shortly after. In certain embodiments, the AUC is $AUC_{0-24h}$. In other embodiments, the AUC is $AUC_{0-inf}$.

Aspects of the present disclosure further relate to treatment regimens involving the administration of pharmaceutical composition of the disclosure, and a gastric acid-reducing agent. Such treatment regimens may be for treating a proliferative disorder in a patient in need thereof, or for treating a proliferative disorder and a condition caused by the overproduction of stomach acid or exacerbated by stomach acid in a patient in need thereof.

In some embodiments, the treatment regimen may comprise (a) administering to the patient a first dose, the first dose comprising a therapeutically effective amount of a proton pump inhibitor; and (b) within 2 hours after the first dose, administering a second dose to the patient, the second dose comprising a pharmaceutical composition of the present disclosure. In certain embodiments, the treatment regimen may comprise (a) administering to the patient a first dose, the first dose comprising a therapeutically effective amount of a proton pump inhibitor; and (b) concurrently administering a second dose to the patient, the second dose comprising a pharmaceutical composition of the present disclosure.

In some embodiments, the treatment regimen may comprise (a) administering to the patient a first dose, the first dose comprising a therapeutically effective amount of an $H_2$ antagonist; and (b) within 10 hours after the first dose, administering a second dose to the patient, the second dose comprising a pharmaceutical composition of the present disclosure. In some embodiments, the treatment regimen may comprise (a) administering to the patient a first dose, the first dose comprising a pharmaceutical composition of the present disclosure; and (b) within 2 hours after the first dose, administering a second dose to the patient, the second dose comprising a therapeutically effective amount of an $H_2$ antagonist.

In some embodiments, the treatment regimen may comprise (a) administering to the patient a first dose, the first dose comprising a therapeutically effective amount of an antacid; and (b) within 2 hours after the first dose, administering a second dose to the patient, the second dose comprising a pharmaceutical composition of the present disclosure. In some embodiments, the treatment regimen may comprise (a) administering to the patient a first dose, the first dose comprising a pharmaceutical composition of the present disclosure; and (b) within 2 hours after the first dose, administering a second dose to the patient, the second dose comprising a therapeutically effective amount of an antacid.

Methods of Treating a Patient Having Elevated Gastric pH

The pharmaceutical compositions of the present disclosure may be suitably administered to subjects or patients with an elevated gastric pH.

One aspect of the present disclosure relates to the use of the nilotinib ASDs or pharmaceutical compositions of the present disclosure to deliver nilotinib to a subject or patient with elevated gastric pH. Some embodiments relate to a method of delivering nilotinib to a subject with elevated gastric pH, the method comprising administering the ASD or pharmaceutical composition of the present disclosure to the subject or patient. Some embodiments relate to a use of a nilotinib ASD or pharmaceutical composition of the present disclosure for delivering nilotinib to a subject or patient with elevated gastric pH, the use comprising administering the ASD or pharmaceutical composition to the subject or patient. Some embodiments relate to a nilotinib ASD or pharmaceutical composition of the present disclosure for use in delivering nilotinib to a subject or patient with elevated gastric pH, the use comprising administering the ASD or pharmaceutical composition to the subject or patient. Some embodiments relate to a use of a nilotinib ASD or pharmaceutical composition of the present disclosure in the manufacture of a medicament for delivering nilotinib to a subject or patient with elevated gastric pH, the delivery comprising administering the ASD or pharmaceutical composition to the subject or patient.

As used herein, "gastric pH" refers to the pH inside a subject's or patient's stomach. Gastric pH may be considered as "elevated" when it is greater than 3.5, or greater than 4, or greater than 5, measured under fasting conditions. Gastric pH can be evaluated using standard methods, or an elevated gastric pH can be inferred from the known effects of, for example, treatment with gastric acid-reducing agents or an identified condition that regularly leads to a measurable elevated gastric pH.

In the practice of the present disclosure, subject or patient may have an elevated gastric pH due to different reasons, including, but not limited to, the subject or patient was administered a gastric acid-reducing agent, or the subject or patient may have a condition that leads to elevated gastric pH. Elevated gastric pH can result from conditions such as hypochlorhydria or achlorhydria, or infection by *Helicobacter pylori* (*H. pylori*) bacteria, for example.

As used herein, the phrase "chronically elevated" in reference to gastric pH means that the subject or patient experiences elevated gastric pH on a persistent or recurring basis. Chronically elevated gastric pH can result from, for example, conditions such as hypochlorhydria or achlorhydria, or infection by *Helicobacter pylori* bacteria.

In some embodiments, the methods of the disclosure may contain a step of identifying a condition by which the patient's gastric pH is elevated (including conditions by which it is chronically elevated). Such a step may comprise diagnosing the underlying cause of the elevated gastric pH. It is known in medical practice how to diagnose hypochlorhydria or achlorhydria in patient, or how to test for a *Helicobacter pylori* bacteria infection. Hypochlorhydria or achlorhydria can be diagnosed, for example, by measuring stomach acid levels under different conditions. *Helicobacter pylori* bacterial infection can be diagnosed by an appropriate blood test, stool test, breath test, or scope test, for example.

In some embodiments, the nilotinib ASD or pharmaceutical composition may be administered to a subject or patient without regard to gastric pH. Thus, the subject or patient may be administered the nilotinib ASD or pharmaceutical composition no matter whether the subject or patient has normal gastric pH (i.e., gastric pH below 3.5, generally in the range 1.5 to 3) or has elevated gastric pH as described herein. This is beneficial when, for example, the subject or patient has gastric pH that fluctuates due to irregular or episodic use of gastric acid-reducing agents, or if the subject or patient has hypochlorhydria (resulting in a gastric pH that may fluctuate depending on factors such as whether the subject or patient has recently eaten).

In some embodiments, administration of an ASD or pharmaceutical composition of the present disclosure to a subject or patient who has elevated gastric pH exhibits a pharmacokinetic profile for nilotinib that is similar to the pharmacokinetic profile resulting from administration of the ASD or pharmaceutical composition to a subject or patient who has normal gastric pH. In certain embodiments, single administration of the ASD or pharmaceutical composition to a subject or patient with elevated gastric pH results in $AUC_{0-t}$ (such as $AUC_{0-24h}$, $AUC_{0-last}$ or $AUC_{0-inf}$) and/or $C_{max}$ of nilotinib that is within 50%, or within 40%, or within 30%, of the $AUC_{0-t}$ and/or $C_{max}$ of nilotinib that results from single administration of the ASD or pharmaceutical composition to a subject or patient with normal gastric pH. In certain embodiments, the $AUC_{0-t}$ is $AUC_{0-24h}$. In other embodiments, the $AUC_{0-t}$ is $AUC_{0-inf}$.

In certain embodiments, administration of the ASD or pharmaceutical composition of the present disclosure in a subject or patient with elevated gastric pH may provide $AUC_{0-t}$ (such as $AUC_{0-24h}$, $AUC_{0-last}$ or $AUC_{0-inf}$) and $C_{max}$ in the subject's or patient's plasma that are within the 80% to 125% bioequivalence criteria compared to administration of a conventional immediate-release nilotinib composition dosed to subjects or patients with normal gastric pH. In certain embodiments, the $AUC_{0-t}$ is $AUC_{0-24h}$. In other embodiments, the $AUC_{0-t}$ is $AUC_{0-inf}$.

In the practice of the present disclosure, administration of an ASD or a pharmaceutical composition can provide enhanced exposure as compared to standard immediate-release compositions. In some embodiments, single administration of an ASD or pharmaceutical composition of the present disclosure to a subject or patient who has elevated gastric pH exhibits greater AUC and/or $C_{max}$ as compared to single administration of a conventional immediate-release composition of nilotinib (e.g., TASIGNA) to a subject or patient who has elevated gastric pH. (It should be understood that the same molar quantity or "label claim" of nilotinib is administered in each case.) In certain embodiments, the AUC is $AUC_{0-24h}$. In other embodiments, the AUC is $AUC_{0-inf}$. In certain embodiments, single administration of the ASD or pharmaceutical composition to a subject or patient with elevated gastric pH results in $AUC_{0-t}$ and/or $C_{max}$ of nilotinib that is at least 80% greater, or at least 100% greater, or at least 150% greater, or at least 200% greater, than the $AUC_{0-t}$ and/or $C_{max}$ of nilotinib that results from administration of a conventional immediate-release composition of nilotinib to the subject or patient with elevated gastric pH. In certain embodiments, the $AUC_{0-t}$ is $AUC_{0-24h}$. In other embodiments, the $AUC_{0-t}$ is $AUC_{0-inf}$.

Further, one aspect of the present disclosure relates to the use of the nilotinib ASDs or pharmaceutical compositions of the present disclosure to deliver nilotinib to a subject without regard to the subject's gastric pH. Some embodiments relate to a method of delivering nilotinib to a subject without regard to the subject's gastric pH, the method comprising administering the ASD or pharmaceutical composition of the present disclosure to the subject. Some embodiments relate to a use of a nilotinib ASD or pharmaceutical composition of the present disclosure for delivering nilotinib to a subject without regard to the subject's gastric pH, the use comprising administering the ASD or pharmaceutical composition to the subject. Some embodiments relate to a nilotinib ASD or pharmaceutical composition of the present disclosure for use in delivering nilotinib to a subject without regard to the subject's gastric pH, the use comprising administering the ASD or pharmaceutical composition to the subject. Some embodiments relate to a use of a nilotinib ASD or pharmaceutical composition of the present disclosure in the manufacture of a medicament for delivering nilotinib to a subject without regard to the subject's gastric pH, the delivery comprising administering the ASD or pharmaceutical composition to the subject. According to these embodiments, the subject may be administered the nilotinib ASD or pharmaceutical composition no matter whether the subject has normal gastric pH or has elevated gastric pH as described herein.

Pharmaceutical Composition Having Improved Variability

The pharmaceutical compositions of the present disclosure may, in some embodiments, provide a less variable in vivo pharmacokinetic performance.

As used herein, the phrase "improved variability composition" refers to a composition of the present disclosure that exhibits a lower coefficient of variation with respect to one or more pharmacokinetic parameters when administered to an appropriate set of healthy human subjects, as compared to the coefficient of variation observed for a conventional immediate-release formulation of nilotinib (e.g., TASIGNA) when administered under similar conditions. For this assessment, the set of healthy human subjects should include a suitable number of subjects such that the study would be sufficiently powered to demonstrate bioequivalence, according to standard practices and relevant FDA guidelines.

In some embodiments, the improved variability composition provides a coefficient of variation with respect to at least one pharmacokinetic parameter that is 30% lower, 25% lower, 20% lower, 15% lower, 10% lower, or 5% lower than the coefficient of variation observed for the standard commercial, immediate-release composition of nilotinib (e.g., TASIGNA) when administered under similar conditions. The pharmacokinetic parameter can be any of $C_{max}$, $AUC_{last}$ and $AUC_{0-inf}$. In some embodiments, the improved variability composition provides an improvement with respect to $C_{max}$ and at least one of $AUC_{last}$ and $AUC_{0-inf}$. In other embodiments, the improved variability composition provides an improvement with respect to all of $C_{max}$, $AUC_{last}$ and $AUC_{0-inf}$.

In particular, it has been observed that compositions according to the present disclosure can provide a lower coefficient of variation for pharmacokinetic parameters when administered to healthy human subjects in a fasted state. As shown in Example 5 (Table 24), test compositions exhibited a lower coefficient of variation with respect to $C_{max}$, $AUC_{last}$ and $AUC_{0-inf}$ under these conditions. The observed CV for the test compositions was at least 30% lower with respect to $C_{max}$, as compared to the reference composition.

Kits Comprising a Pharmaceutical Composition and a Package Insert

In some embodiments, the disclosure provides a kit containing a pharmaceutical composition according to any of the above-described aspects of the disclosure, as well as a package insert. As used herein, a "kit" is a commercial unit of sale, which may comprise a fixed number of doses of the pharmaceutical composition. By way of example only, a kit may provide a 30-day supply of dosage units of one or more fixed strengths, the kit comprising 30 dosage units, 60 dosage units, 90 dosage units, 120 dosage units, or other appropriate number according to a physician's instruction. As another example, a kit may provide a 90-day supply of dosage units.

As used herein, "package insert" means a document which provides information on the use of the pharmaceutical composition, safety information, and other information required by a regulatory agency. A package insert can be a physical printed document in some embodiments. Alternatively, a package insert can be made available electronically to the user, such as via the Daily Med service of the National Library of Medicines of the National Institute of Health, which provides up-to-date prescribing information (see https://dailymed.nlm.nih.gov/dailymed/index.cfm).

In some embodiments, the package insert informs a user of the kit that the pharmaceutical composition can be administered with food. In some embodiments, the package insert informs a user of the kit that the pharmaceutical composition can be administered with or without food. In some embodiments, the package insert does not include a warning that the pharmaceutical composition should not be administered with food.

In some embodiments, the package insert informs a user of the kit that the pharmaceutical composition can be co-administered with a gastric acid-reducing agent. In some embodiments, the package insert does not comprise a warning that the pharmaceutical composition should not be co-administered with $H_2$ antagonists or proton pump inhibitors.

In some embodiments, the package insert informs a user of the kit that a proton pump inhibitor can be co-administered with the pharmaceutical composition. In some embodiments, the package insert does not include a warning that concomitant use of a proton pump inhibitor with the pharmaceutical composition should be avoided.

In some embodiments, the package insert informs a user of the kit that an H2 antagonist can be co-administered with the pharmaceutical composition. In some embodiments, the package insert does not inform the user to use an H2 antagonist approximately 10 hours before or approximately 2 hours after administration of the pharmaceutical composition. In some embodiments, the package insert informs the user that an H2 antagonist can be used within approximately 10 hours before or within approximately 2 hours after administration of the pharmaceutical composition.

In some embodiments, the package insert informs a user of the kit that an antacid can be co-administered with the pharmaceutical composition. In some embodiments, the package insert does not inform the user to use an antacid approximately 2 hours before or approximately 2 hours after administration of the pharmaceutical composition. In some embodiments, the package insert informs the user that an antacid can be used within approximately 2 hours before or within approximately 2 hours after administration of the pharmaceutical composition.

In some embodiments, the package insert informs a user of the kit that the pharmaceutical composition can be suitably administered to a user having chronically elevated gastric pH. In some embodiments, the package insert informs a user of the kit that the pharmaceutical composition can be suitably administered to a patient diagnosed with or afflicted by achlorhydria or hypochlorhydria. In some embodiments, the package insert informs a user of the kit that the pharmaceutical composition can be suitably administered to a patient diagnosed with or afflicted by *Helicobacter pylori* infection.

The present disclosure will be further illustrated and/or demonstrated in the following Examples, which are given for illustration/demonstration purposes only and are not intended to limit the disclosure in any way.

Embodiments of the Disclosure Include:

Embodiment ASD1 is an amorphous solid dispersion comprising nilotinib and one or more polymers.

Embodiment ASD2 is an amorphous solid dispersion comprising nilotinib and one or more polymers; wherein the nilotinib and the one or more polymers are present in the amorphous solid dispersion in a w/w ratio of 20:80 to 95:5 (nilotinib:polymer). Embodiment ASD3 is an amorphous solid dispersion comprising nilotinib and one or more polymers, wherein the nilotinib and the one or more polymers are present in the amorphous solid dispersion in a w/w ratio of 40:60 to 70:30 (nilotinib:polymer). Embodiment ASD4 is an amorphous solid dispersion comprising nilotinib and one or more polymers, wherein the nilotinib and the one or more polymers are present in the amorphous solid dispersion in a w/w ratio of 50:50 (nilotinib:polymer).

Embodiment ASD5 is the amorphous solid dispersion according to any of Embodiments ASD1 to ASD4, wherein the one or more polymers exhibits pH-dependent solubility.

Embodiment ASD6 is the amorphous solid dispersion according to any of Embodiments ASD1 to ASD5, wherein the one or more polymers comprises a hydroxypropyl methylcellulose acetate succinate. Embodiment ASD7 is the amorphous solid dispersion according to Embodiment ASD6, wherein the one or more polymers consists essentially of a hydroxypropyl methylcellulose acetate succinate. Embodiment ASD8 is the amorphous solid dispersion according to any of Embodiments ASD6 to ASD7, wherein the one or more polymers comprise a hydroxypropyl methylcellulose acetate succinate characterized by an acetyl substitution of 7 to 11% and a succinyl substitution of 10 to 14%.

Embodiment ASD9 is the amorphous solid dispersion according to any of Embodiments ASD1 to ASD5, wherein the one or more polymers comprises a methacrylic acid and ethyl acrylate copolymer. Embodiment ASD10 is the amorphous solid dispersion according to Embodiment ASD9, wherein the one or more polymers consists essentially of a methacrylic acid and ethyl acrylate copolymer. Embodiment ASD11 is the amorphous solid dispersion according to any of Embodiments ASD9 to ASD10, wherein the one or more polymers comprise a methacrylic acid and ethyl acrylate copolymer that is insoluble in an aqueous medium at pH of 5 or lower, and soluble in an aqueous medium at pH 5.5 or greater.

Embodiment ASD12 is the amorphous solid dispersion according to any of Embodiments ASD1 to ASD11 wherein the amorphous solid dispersion consists essentially of nilotinib and the one or more polymers.

Embodiment ASD13 is the amorphous solid dispersion according to any of Embodiments ASD1 to ASD12, wherein the amorphous solid dispersion comprises one or more antioxidants. Embodiment ASD14 is the amorphous solid dispersion according to any of Embodiments ASD1 to ASD13, wherein the amorphous solid dispersion comprises one or more antioxidants that are present in an amount of 0.001% to 2% by weight of the amorphous solid dispersion. Embodiment ASD15 is the amorphous solid dispersion according to any of Embodiments ASD1 to ASD14, wherein the amorphous solid dispersion comprises one or more antioxidants that are present in an amount of 0.05% to 0.5% by weight of the amorphous solid dispersion. Embodiment ASD16 is the amorphous solid dispersion according to any of Embodiments ASD1 to ASD15, wherein the amorphous solid dispersion comprises one or more antioxidants selected from butylated hydroxytoluene.

Embodiment ASD17 is the amorphous solid dispersion according to any of Embodiments ASD1 to ASD16, wherein the amorphous solid dispersion is prepared by a process comprising electrospraying. Embodiment ASD18 is the amorphous solid dispersion according to any of Embodiments ASD1 to ASD16, wherein the amorphous solid dispersion is an electrosprayed amorphous solid dispersion.

Embodiment ASD19 is the amorphous solid dispersion according to any of Embodiments ASD1 to ASD16, wherein the amorphous solid dispersion is prepared by a process comprising spray drying. Embodiment ASD20 is the amorphous solid dispersion according to any of Embodiments ASD1 to ASD16, wherein the amorphous solid dispersion is a spray-dried amorphous solid dispersion.

Embodiment ASD21 is the amorphous solid dispersion according to any of Embodiments ASD1 to ASD20, wherein the amorphous solid dispersion remains amorphous or essentially amorphous as determined by powder X-ray diffraction after storage at 40° C./75% relative humidity for 6 months. Embodiment ASD22 is the amorphous solid dispersion according to any of Embodiments ASD1 to ASD20, wherein the amorphous solid dispersion remains amorphous or essentially amorphous as determined by powder X-ray diffraction after storage at 25° C./60% relative humidity for 6 months.

Embodiment ASD23 is the amorphous solid dispersion according to any of Embodiments ASD1 to ASD20, wherein the amorphous solid dispersion comprises a water content as measured by coulometric Karl Fischer titration of not more than 4% after storage at 25° C./60% RH for 12 months. Embodiment ASD24 is the amorphous solid dispersion according to any of Embodiments ASD1 to ASD20, wherein the amorphous solid dispersion comprises a water content as measured by coulometric Karl Fischer titration of not more than 4% after storage at 40° C./75% RH for 6 months.

Embodiment ASD25 is the amorphous solid dispersion according to any of Embodiments ASD1 to ASD20, wherein the amorphous solid dispersion is characterized by an assay level of at least 90% as measured by high performance liquid chromatography (HPLC) after storage at 25° C./60% relative humidity for 12 months. Embodiment ASD26 is the amorphous solid dispersion according to any of Embodiments ASD1 to ASD20, wherein the assay level of the amorphous solid dispersion is at least 90% after storage at 40° C./75% relative humidity for 6 months.

Embodiment ASD27 is the amorphous solid dispersion according to any of Embodiments ASD1 to ASD20, wherein the amorphous solid dispersion comprises a total related substances as measured by HPLC of not more than 1% after storage at 25° C./60% RH for 12 months. Embodiment ASD28 is the amorphous solid dispersion according to any of Embodiments ASD1 to ASD20, wherein the amorphous solid dispersion comprises a total related substances as measured by HPLC of not more than 1% after storage at 40° C./75% RH for 6 months.

Embodiment ASD29 is the amorphous solid dispersion according to any of Embodiments ASD1 to ASD20, wherein the amorphous solid dispersion comprises a glass transition temperature as measured by modulated differential scanning calorimetry that does not change by more than 5° C. after storage at 25° C./60% RH for 12 months. Embodiment ASD30 is the amorphous solid dispersion according to any of Embodiments ASD1 to ASD20, wherein the amorphous solid dispersion comprises a glass transition temperature as measured by modulated differential scanning calorimetry that does not change by more than 5° C. after storage at 40° C./75% RH for 6 months.

Embodiment PC1 is a pharmaceutical composition comprising the amorphous solid dispersion according to any of Embodiments ASD1 to ASD30.

Embodiment PC2 is a pharmaceutical composition comprising the amorphous solid dispersion according to any of Embodiments ASD1 to ASD30, and one or more pharmaceutically acceptable additives. Embodiment PC3 is the pharmaceutical composition of Embodiment PC2, wherein the one or more pharmaceutically acceptable additives comprises one or more solubilizers, one or more buffering agent, one or more pH-adjusting agents, one or more surfactants, one or more antioxidants, one or more carriers, or a combination thereof. Embodiment PC4 is the pharmaceutical composition of Embodiment PC2, wherein the one or more pharmaceutically acceptable additives comprises one or more filling agents, one or more binding agents, one or more lubricants, one or more disintegrants, one or more glidants, or a combination thereof. Embodiment PC5 is the pharmaceutical composition of Embodiment PC4, wherein the pharmaceutical composition is a solid dosage form suitable for oral administration. Embodiment PC6 is the pharmaceutical composition of Embodiment PC4, wherein the pharmaceutical composition is presented as a solid dosage form suitable for oral administration, and comprising 25 to 100 mg nilotinib.

Embodiment PC7 is the pharmaceutical composition of Embodiment PC6, wherein, when the oral dosage form is administered to a healthy human subjects in a fasted state, achieves an $AUC_{0-inf}$ and $C_{max}$ within the 80% to 125% bioequivalence criteria as compared to $AUC_{0-inf}$ and $C_{max}$ achieved upon administration of a reference composition, wherein the reference composition is a conventional immediate-release nilotinib composition comprising 200 mg nilotinib monohydrochloride monohydrate.

Embodiment PC8 is the pharmaceutical composition of Embodiment PC6, wherein the pharmaceutical composition is effectively bioequivalent under fasting conditions to a reference composition which is a conventional immediate-release nilotinib composition comprising 200 mg nilotinib monohydrochloride monohydrate; where effective bioequivalence is established by: (a) a 90% confidence interval for AUC which is between 80% and 125%; and (b) a 90% confidence interval for $C_{max}$, which is between 80% and 125%.

Embodiment PC9 is the pharmaceutical composition of Embodiment PC1 to PC8, wherein the pharmaceutical composition is a food-insensitive composition.

Embodiment PC10 is the pharmaceutical composition of Embodiment PC1 to PC9, wherein the pharmaceutical composition is a gastric acid-insensitive composition.

Embodiment PC11 is the pharmaceutical composition of Embodiment PC1 to PC10, wherein the pharmaceutical composition is an improved variability composition.

Embodiment MT1 is a method of treating a proliferative disorder in a patient in need thereof, the method comprising administering to the patient a pharmaceutical composition according to any of Embodiments PC1 to PC11.

Embodiment MT2 is a method of treating a proliferative disorder in a patient in need thereof, the method comprising administering to the patient a pharmaceutical composition according to any of Embodiments PC1 to PC11, wherein the pharmaceutical composition is administered without regard to consumption of food. Embodiment MT3 is a method of treating a proliferative disorder in a patient in need thereof, the method comprising administering to the patient a pharmaceutical composition according to any of Embodiments PC1 to PC11, wherein the pharmaceutical composition is administered without regard to whether the patient is in a fasted state or a fed state. Embodiment MT4 is a method of treating a proliferative disorder in a patient in need thereof, the method comprising administering to the patient a pharmaceutical composition according to any of Embodiments PC1 to PC11, without a food effect.

Embodiment MT5 is a method of safely delivering nilotinib to a patient in need thereof, the method comprising: (a) administering to the patient a therapeutically effective amount of a pharmaceutical composition according to any of Embodiments PC1 to PC11, and (b) administering a meal to the patient; wherein steps (a) and (b) occur within less than two hours of each other.

Embodiment MT6 is a method of delivering a therapeutically effective amount of nilotinib to a patient without regard to consumption of food, comprising administering to the patient a pharmaceutical composition according to any of Embodiments PC1 to PC11. Embodiment MT7 is a method of delivering a therapeutically effective amount of nilotinib to a patient without regard to whether the patient is in a fasted state or a fed state, comprising administering to the patient a pharmaceutical composition according to any of Embodiments PC1 to PC11.

Embodiment MT8 is the method according to any of Embodiments MT1 to MT7, wherein administration of the pharmaceutical composition to the patient in a fed state results in plasma $C_{max}$ of nilotinib that is less than the plasma $C_{max}$ of nilotinib resulting from administration of the pharmaceutical composition to the patient in a fasted state. Embodiment MT9 is the method according to any of Embodiments MT1 to MT7, wherein administration of the pharmaceutical composition to the patient in a fed state results in plasma $C_{max}$ of nilotinib that is within 30% of the plasma $C_{max}$ of nilotinib resulting from administration of the pharmaceutical composition to the patient in a fasted state.

Embodiment MT10 is the method according to any of Embodiments MT1 to MT9, wherein administration of the pharmaceutical composition to the patient in a fed state results in plasma AUC of nilotinib that is less than the plasma AUC of nilotinib resulting from administration of the pharmaceutical composition to the patient in a fasted state. Embodiment MT11 is the method according to any of Embodiments MT1 to MT9, wherein administration of the pharmaceutical composition to the patient in a fed state results in plasma AUC of nilotinib that is within 30% of the plasma AUC of nilotinib resulting from administration of the pharmaceutical composition to the patient in a fasted state.

Embodiment MT12 is the method according to any of Embodiments MT1 to MT9, wherein administration of the pharmaceutical composition to the patient in a fed state results in plasma AUC of nilotinib that is within 15% of the plasma AUC of nilotinib resulting from administration of the pharmaceutical composition to the patient in a fasted state. Embodiment MT13 is the method according to any of Embodiments MT10 to MT12, wherein AUC is $AUC_{0-12h}$. Embodiment MT14 is the method according to any of Embodiments MT10 to MT12, wherein AUC is $AUC_{0-24h}$. Embodiment MT15 is the method according to any of Embodiments MT10 to MT12, wherein AUC is $AUC_{0-last}$. Embodiment MT16 is the method according to any of Embodiments MT10 to MT12, wherein AUC is $AUC_{0-inf}$.

Embodiment MT17 is the method according to any of Embodiments MT1 to MT7, wherein administration of the pharmaceutical composition to the patient in a fasted state results in plasma $C_{max}$ of nilotinib that is greater than the plasma $C_{max}$ of nilotinib resulting from administration of an immediate-release crystalline nilotinib formulation that has two times to four times the amount of nilotinib as the pharmaceutical composition. Embodiment MT18 is the method according to any of Embodiments MT1 to MT7, wherein administration of the pharmaceutical composition to the patient in a fed state results in plasma $C_{max}$ of nilotinib that is within 25% of the plasma $C_{max}$ of nilotinib resulting from administration of an immediate-release crystalline nilotinib formulation that has two times to four times the amount of nilotinib as the pharmaceutical composition.

Embodiment MT19 is the method according to any of Embodiments MT1 to MT7, wherein administration of the pharmaceutical composition to the patient in a fasted state results in plasma AUC of nilotinib that is greater than the plasma AUC of nilotinib resulting from administration of an immediate-release crystalline nilotinib formulation that has two times to four times the amount of nilotinib as the pharmaceutical composition. Embodiment MT20 is the method according to any of Embodiments MT1 to MT7, wherein administration of the pharmaceutical composition to the patient in a fed state results in plasma AUC of nilotinib that is within 25% of the plasma AUC of nilotinib resulting from administration of an immediate-release crystalline nilotinib formulation that has two times to four times the amount of nilotinib as the pharmaceutical composition. Embodiment MT21 is the method according to any of Embodiments MT1 to MT7, wherein administration of the pharmaceutical composition to the patient in a fed state results in plasma AUC of nilotinib that is within 20% of the plasma AUC of nilotinib resulting from administration of an immediate-release crystalline nilotinib formulation that has two times to four times the amount of nilotinib as the pharmaceutical composition. Embodiment MT22 is the method according to any of Embodiments MT19 to MT21, wherein AUC is $AUC_{0-12h}$. Embodiment MT23 is the method according to any of Embodiments MT19 to MT21, wherein AUC is $AUC_{0-24h}$. Embodiment MT24 is the method according to any of Embodiments MT19 to MT21, wherein AUC is $AUC_{0-last}$. Embodiment MT25 is the method according to any of Embodiments MT19 to MT21, wherein AUC is $AUC_{0-inf}$.

Embodiment MT26 is a method of treating a proliferative disorder in a patient in need thereof, the method comprising administering to the patient a pharmaceutical composition according to any of Embodiments PC1 to PC11, without regard to whether the patient is co-administered a proton pump inhibitor. Embodiment MT27 is a method of delivering a therapeutically effective amount of nilotinib to a patient who is co-administered a proton pump inhibitor, comprising administering to the patient (a) a pharmaceutical composition according to any of Embodiments PC1 to PC11, and (b) a proton pump inhibitor.

Embodiment MT28 is the method according to any of Embodiments MT1 to MT27, wherein the proliferative disorder is cancer. Embodiment MT29 is the method according to any of Embodiments MT1 to MT27, wherein the proliferative disorder is Philadelphia chromosome positive chronic myeloid leukemia. Embodiment MT30 is the method according to any of Embodiments MT1 to MT27, wherein the proliferative disorder is chronic phase Philadelphia chromosome positive chronic myeloid leukemia resistant or intolerant to prior tyrosine kinase inhibitor therapy.

Embodiment MS1 is a method of delivering a therapeutically relevant exposure of nilotinib to a subject without regard to whether the subject is in a fasted state or a fed state, the method comprising administering to the subject a pharmaceutical composition according to any of Embodiments PC1 to PC11.

Embodiment MS2 is the method according to Embodiment MS1, wherein administration of the pharmaceutical composition to the subject in a fed state results in plasma $C_{max}$ of nilotinib that is less than the plasma $C_{max}$ of nilotinib resulting from administration of the pharmaceutical composition to the subject in a fasted state. Embodiment MS3 is the method according to Embodiment MS1, wherein administration of the pharmaceutical composition to the subject in a fed state results in plasma $C_{max}$ of nilotinib that is within 30% of the plasma $C_{max}$ of nilotinib resulting from administration of the pharmaceutical composition to the subject in a fasted state.

Embodiment MS4 is the method according to Embodiment MS1, wherein administration of the pharmaceutical composition to the subject in a fed state results in plasma AUC of nilotinib that is less than the plasma AUC of nilotinib resulting from administration of the pharmaceutical composition to the subject in a fasted state. Embodiment MS5 is the method according to Embodiment MS1, wherein administration of the pharmaceutical composition to the subject in a fed state results in plasma AUC of nilotinib that is within 30% of the plasma AUC of nilotinib resulting from administration of the pharmaceutical composition to the subject in a fasted state. Embodiment MS6 is the method according to Embodiment MS1, wherein administration of the pharmaceutical composition to the subject in a fed state results in plasma AUC of nilotinib that is within 15% of the plasma AUC of nilotinib resulting from administration of the pharmaceutical composition to the subject in a fasted state. Embodiment MS7 is the method according to any of Embodiments MS4 to MS6, wherein AUC is $AUC_{0-12h}$. Embodiment MS8 is the method according to any of Embodiments MS4 to MS6, wherein AUC is $AUC_{0-24h}$. Embodiment MS9 is the method according to any of Embodiments MS4 to MS6, wherein AUC is $AUC_{0-last}$. Embodiment MS10 is the method according to any of Embodiments MS4 to MS6, wherein AUC is $AUC_{0-inf}$.

Embodiment MS11 is the method according to Embodiment MS1, wherein administration of the pharmaceutical composition to the subject in a fasted state results in plasma $C_{max}$ of nilotinib that is greater than the plasma $C_{max}$ of nilotinib resulting from administration of an immediate-release crystalline nilotinib formulation that has two times to four times the amount of nilotinib as the pharmaceutical composition. Embodiment MS12 is the method according to Embodiment MS1, wherein administration of the pharmaceutical composition to the subject in a fed state results in plasma $C_{max}$ of nilotinib that is within 25% of the plasma $C_{max}$ of nilotinib resulting from administration in a fasted state of an immediate-release crystalline nilotinib formulation that has two times to four times the amount of nilotinib as the pharmaceutical composition.

Embodiment MS13 is the method according to Embodiment MS1, wherein administration of the pharmaceutical composition to the subject in a fasted state results in plasma AUC of nilotinib that is greater than the plasma AUC of nilotinib resulting from administration of an immediate-release crystalline nilotinib formulation that has two times to four times the amount of nilotinib as the pharmaceutical composition. Embodiment MS14 is the method according to Embodiment MS1, wherein administration of the pharmaceutical composition to the subject in a fed state results in plasma AUC of nilotinib that is within 25% of the plasma AUC of nilotinib resulting from administration in a fasted state of an immediate-release crystalline nilotinib formulation that has two times to four times the amount of nilotinib as the pharmaceutical composition. Embodiment MS15 is the method according to Embodiment MS1, wherein administration of the pharmaceutical composition to the subject in a fed state results in plasma AUC of nilotinib that is within 20% of the plasma AUC of nilotinib resulting from administration in a fasted state of an immediate-release crystalline nilotinib formulation that has two times to four times the amount of nilotinib as the pharmaceutical composition. Embodiment MS16 is the method according to any of Embodiments MS13 to MS15, wherein AUC is $AUC_{0-12h}$. Embodiment MS17 is the method according to any of Embodiments MS13 to MS15, wherein AUC is $AUC_{0-24h}$. Embodiment MS18 is the method according to any of Embodiments MS13 to MS15, wherein AUC is $AUC_{0-last}$. Embodiment MS19 is the method according to any of Embodiments MS13 to MS15, wherein AUC is $AUC_{0-inf}$.

Embodiment TR1 is a treatment regimen for treating a proliferative disorder in a patient in need thereof, the regimen comprising: (a) administering to the patient a first dose, the first dose comprising a proton pump inhibitor; and (b) within 12 hours of the first dose, administering a second dose to the patient, the second dose comprising a pharmaceutical composition according to any of Embodiments PC1 to PC11.

Embodiment TR2 is a treatment regimen for treating a proliferative disorder and a condition caused by the overproduction of stomach acid or exacerbated by stomach acid in a patient in need thereof, the regimen comprising: (a) administering to the patient a first dose, the first dose comprising therapeutically effective amount of a proton pump inhibitor; and (b) within 12 hours of the first dose, administering a second dose to the patient, the second dose comprising a pharmaceutical composition according to any of Embodiments PC1 to PC11.

Embodiment TR3 is the treatment regimen according to any of Embodiments TR1 to TR2, wherein the first dose comprises a standard dosage of a proton pump inhibitor selected from rabeprazole, esomeprazole, lansoprazole, omeprazole, pantoprazole, dexlansoprazole, or a combination thereof. Embodiment TR4 is the treatment regimen according to any of Embodiments TR1 to TR2, wherein the first dose comprises a standard dosage of omeprazole.

Embodiment TR5 is the treatment regimen according to any of Embodiments TR1 to TR4, wherein step (a) occurs before step (b). Embodiment TR6 is the treatment regimen according to any of Embodiments TR1 to TR4, wherein step (b) occurs before step (a). Embodiment TR7 is the treatment regimen according to any of Embodiments TR1 to TR6, wherein the second dose is administered within 8 hours of the first dose. Embodiment TR8 is the treatment regimen according to any of Embodiments TR1 to TR6, wherein the second dose is administered within 6 hours of the first dose. Embodiment TR9 is the treatment regimen according to any of Embodiments TR1 to TR6, wherein the second dose is administered within 4 hours of the first dose. Embodiment TR10 is the treatment regimen according to any of Embodiments TR1 to TR6, wherein the second dose is administered within 2 hours of the first dose. Embodiment TR11 is the treatment regimen according to any of Embodiments TR1 to TR6, wherein the first dose and the second dose are administered concurrently.

Embodiment TR12 is a treatment regimen for treating a proliferative disorder in a patient in need thereof, the regimen comprising: (a) administering to the patient a first dose, the first dose comprising an $H_2$ antagonist; and (b) within 10 hours after the first dose, administering a second dose to the patient, the second dose comprising a pharmaceutical composition according to any of Embodiments PC1 to PC11. Embodiment TR13 is a treatment regimen for treating a proliferative disorder and a condition caused by the overproduction of stomach acid or exacerbated by stomach acid in a patient in need thereof, the regimen comprising: (a) administering to the patient a first dose, the first dose comprising a therapeutically effective amount of an $H_2$ antagonist; and (b) within 10 hours after the first dose, administering a second dose to the patient, the second dose comprising a pharmaceutical composition according to any of Embodiments PC1 to PC11. Embodiment TR14 is the treatment regimen according to any of Embodiments TR12 to TR13, wherein the second dose is administered within 8 hours of the first dose. Embodiment TR15 is the treatment regimen according to any of Embodiments TR12 to TR13, wherein the second dose is administered within 6 hours of the first dose. Embodiment TR16 is the treatment regimen according to any of Embodiments TR12 to TR13, wherein the second dose is administered within 4 hours of the first dose. Embodiment TR17 is the treatment regimen according to any of Embodiments TR12 to TR13, wherein the second dose is administered within 2 hours of the first dose. Embodiment TR18 is the treatment regimen according to any of Embodiments TR12 to TR13, wherein the first dose and the second dose are administered concurrently.

Embodiment TR19 is a treatment regimen for treating a proliferative disorder in a patient in need thereof, the regimen comprising: (a) administering to the patient a first dose, the first dose comprising a pharmaceutical composition according to any of Embodiments PC1 to PC11; and (b) within 2 hours after the first dose, administering a second dose to the patient, the second dose comprising an $H_2$ antagonist. Embodiment TR20 is a treatment regimen for treating a proliferative disorder and a condition caused by the overproduction of stomach acid or exacerbated by stomach acid in a patient in need thereof, the regimen comprising: (a) administering to the patient a first dose, the first dose comprising a pharmaceutical composition according to any of Embodiments PC1 to PC11; and (b) within 2 hours after the first dose, administering a second dose to the patient, the second dose comprising a therapeutically effective amount of an $H_2$ antagonist. Embodiment TR21 is the treatment regimen according to any of Embodiments TR19 to TR20, wherein the first dose and the second dose are administered concurrently. Embodiment TR22 is the treatment regimen according to any of Embodiments TR12 to TR21, wherein the $H_2$ antagonist is selected from famotidine, cimetidine, nizatidine, ranitidine, or a combination thereof. Embodiment TR23 is the treatment regimen according to any of Embodiments TR12 to TR21, wherein the $H_2$ antagonist is famotidine.

Embodiment TR24 is a treatment regimen for treating a proliferative disorder in a patient in need thereof, the regimen comprising: (a) administering to the patient a first dose, the first dose comprising an antacid; and (b) within 2 hours of the first dose, administering a second dose to the patient, the second dose comprising a pharmaceutical composition according to any of Embodiments PC1 to PC11. Embodiment TR25 is a treatment regimen for treating a proliferative disorder and a condition caused by the overproduction of stomach acid or exacerbated by stomach acid in a patient in need thereof, the regimen comprising: (a) administering to the patient a first dose, the first dose comprising a pharmaceutical composition according to any of Embodiments PC1 to PC 11; and (b) within 2 hours of the first dose, administering a second dose to the patient, the second dose comprising a therapeutically effective amount of an antacid. Embodiment TR26 is the treatment regimen according to any of Embodiments TR24 to TR25, wherein the first dose and the second dose are administered concurrently. Embodiment TR27 is the treatment regimen according to any of Embodiments TR24 to TR26, wherein the antacid is selected from aluminum hydroxide, magnesium hydroxide, and combinations thereof.

Embodiment TR28 is the treatment regimen according to any of Embodiments TR1 to TR27, wherein the proliferative disorder is cancer. Embodiment TR29 is the treatment regimen according to any of Embodiments TR1 to TR27, wherein the proliferative disorder is Philadelphia chromosome positive chronic myeloid leukemia. Embodiment TR30 is the treatment regimen according to any of Embodiments TR1 to TR27, wherein the proliferative disorder is chronic phase Philadelphia chromosome positive chronic myeloid leukemia resistant or intolerant to prior tyrosine kinase inhibitor therapy.

Embodiment TR31 is the treatment regimen according to any of Embodiments TR1 to TR30, wherein administration of the pharmaceutical composition provides a therapeutically relevant exposure of nilotinib to the patient.

Embodiment KT1 is a kit for sale to a user, the kit comprising a pharmaceutical composition according to any of Embodiments PC1 to PC11 and a package insert, wherein the package insert informs the user that the pharmaceutical composition can be administered with food. Embodiment KT2 is a kit for sale to a user, the kit comprising a pharmaceutical composition according to any of Embodiments PC1 to PC11 and a package insert, wherein the package insert informs the user that the pharmaceutical composition can be administered with or without food. Embodiment KT3 is a kit for sale to a user, the kit comprising a pharmaceutical composition according to any of Embodiments PC1 to PC11 and a package insert, wherein the package insert does not include a warning that the pharmaceutical composition should not be administered with food.

Embodiment KT4 is a kit for sale to a user, the kit comprising a pharmaceutical composition according to any of Embodiments PC1 to PC11 and a package insert, wherein the package insert that informs the user that a proton pump inhibitor can be co-administered with the pharmaceutical composition. Embodiment KT5 is a kit for sale to a user, the kit comprising a pharmaceutical composition according to any of Embodiments PC1 to PC11 and a package insert, wherein the package insert does not include a warning that concomitant use of a proton pump inhibitor with the pharmaceutical composition should be avoided.

Embodiment KT6 is a kit for sale to a user, the kit comprising a pharmaceutical composition according to any of Embodiments PC1 to PC11 and a package insert, wherein the package insert informs the user that an $H_2$ antagonist can be co-administered with the pharmaceutical composition. Embodiment KT7 is a kit for sale to a user, the kit comprising a pharmaceutical composition according to any of Embodiments PC1 to PC11 and a package insert, wherein the package insert does not inform a user of the kit to use an $H_2$ antagonist approximately 10 hours before or approximately 2 hours after administration of the pharmaceutical composition. Embodiment KT8 is a kit for sale to a user, the kit comprising a pharmaceutical composition according to any of Embodiments PC1 to PC11 and a package insert, wherein the package insert informs a user of the kit that an $H_2$ antagonist can be used within approximately 10 hours before or within approximately 2 hours after administration of the pharmaceutical composition.

Embodiment KT9 is a kit for sale to a user, the kit comprising a pharmaceutical composition according to any of Embodiments PC1 to PC11 and a package insert, wherein the package insert informs the user that an antacid can be co-administered with the pharmaceutical composition. Embodiment KT10 is a kit for sale to a user, the kit comprising a pharmaceutical composition according to any of Embodiments PC1 to PC11 and a package insert, wherein the package insert does not inform a user of the kit to use an antacid approximately 2 hours before or approximately 2 hours after administration of the pharmaceutical composition. Embodiment KT11 is a kit for sale to a user, the kit comprising a pharmaceutical composition according to any of Embodiments PC1 to PC11 and a package insert, wherein the package insert informs a user of the kit that an antacid can be used within approximately 2 hours before or within approximately 2 hours after administration of the pharmaceutical composition.

Embodiment KT12 is a kit for sale to a user, the kit comprising a pharmaceutical composition according to any of Embodiments PC1 to PC11 and a package insert, wherein the package insert informs the user that the pharmaceutical composition can be suitably administered if the user has chronically elevated gastric pH. Embodiment KT13 is a kit for sale to a user, the kit comprising a pharmaceutical composition according to any of Embodiments PC1 to PC11 and a package insert, wherein package insert informs the user that the pharmaceutical composition can be suitably administered if the user has been diagnosed with or is afflicted by achlorhydria or hypochlorhydria. Embodiment KT14 is a kit for sale to a user, the kit comprising a pharmaceutical composition according to any of Embodiments PC1 to PC11 and a package insert, wherein the package insert informs the user that the pharmaceutical composition can be suitably administered if the user has been diagnosed with or is afflicted by *Helicobacter pylori* infection.

EXAMPLES

Example 1. Preparation of Nilotinib ASDs and Stability Study Under Harsh Conditions Nilotinib ASDs were prepared according to embodiments of the present disclosure. A study was then performed to assess the chemical and physical stability of the nilotinib ASDs under harsh accelerated conditions.

Nilotinib ASDs were prepared with either EUDRAGIT L100-55 or HPMC-AS as the polymer, in the ratios shown in Table 2. To prepare each composition, appropriate quantities of the polymer and nilotinib were dissolved in a 50:50 (v/v) solvent mixture of tetrahydrofuran and methanol to provide a liquid feedstock. (The tetrahydrofuran was stabilized with a small quantity of BHT as an antioxidant; therefore, the ASDs prepared in this example will contain a small, unquantified amount of BHT along with nilotinib and polymer.)

TABLE 2

Composition of the nilotinib ASDs for Example 1.

| Components | Nilotinib:Polymer Ratio (w/w) |
|---|---|
| Nilotinib EUDRAGIT L100-55 | 50:50 |
|  | 60:40 |
|  | 70:30 |
|  | 80:20 |
| Nilotinib HPMC-AS | 50:50 |
|  | 60:40 |
|  | 70:30 |
|  | 80:20 |

The resulting feedstocks were sprayed at a total solid concentration of 20 mg/ml using the Nanocopoeia ES machine ENS-P. For each spray run, the spray process parameters, such as extractor voltage and flow rate, were adjusted to achieve an acceptable spray plume.

Following the electrospray processing, each ASD (now in the form of a powder) was subjected to a secondary drying procedure to reduce the levels of residual solvents and moisture. For secondary drying, the ASD powders were placed in an appropriate container and placed into an oven (Lindberg Blue M, Model V01218A) which was heated to 80° C. The powders were dried under vacuum (negative 20" to 28" Hg) for six hours.

For compositions that required multiple spray sub-batches in order to provide enough ASD material to support the stability study, material obtained from sub-batches was combined into a single blend using a Resodyn LabRam II acoustic mixer. Sub-batches were placed into a single container and blended for 2 minutes at a force setting of 40 G.

The resulting ASDs were placed on stability in an open dish under aggressive conditions at 50° C./80% RH. The ASD powders were assessed at t=0, 1 week, 2 weeks, and 4 weeks for amorphicity (XRD), water content (Karl Fisher), glass transition temperature (DSC), and assay/related substances (HPLC).

Amorphicity

Amorphicity (i.e., the lack of crystallinity) for the ASDs was assessed by XRD. Diffraction patterns were obtained by x-ray diffraction using a Rigaku MiniFlex 600. The X-ray source was a long anode Cu Kα. Samples were prepared by placing a small amount of ASD powder on a Rigaku zero-background sample holder with a 0.1 mm indent. A glass slide was then used to firmly pack the powder and ensure the surface of the sample was level with the edge of the sample holder. Instrument details and measurement conditions are specified in Table 3.

TABLE 3

Rigaku MiniFlex instrument and measurement conditions.

| Parameter | Condition | | | |
|---|---|---|---|---|
| Spin | On | | | |
| Slit condition | Variable and fixed slit system | | | |
| Optical device | Soller (inc.): 5.0°<br>Soller (rec.): 5.0° | IHS: 10.0 mm<br>IHS: 13.0 mm | DS: 1.250°<br>Monochromatization: Kb filter (X2, 0.03 mm) | SS: 8.0 mm |
| Detector | D/tex | | | |
| Measurement condition | Scan axis: theta/2-theta<br>Step: 0.02° | Mode: continuous<br>Speed: 5.0°/min | Start: 5.0°<br>Voltage: 40 kV | Stop: 40°<br>Current: 15 mA |

The ASDs were evaluated for amorphicity post-spray (t=0) and after stability. Each XRD scan was assessed for the presence of crystalline peaks, with the results listed in Table 4.

TABLE 4

Summary of ASD amorphicity data for ASDs of Example 1.

| Time Point | Nilotinib:EUDRAGIT L100-55 | | | | Nilotinib:HPMC-AS | | | |
|---|---|---|---|---|---|---|---|---|
| | 50:50 | 60:40 | 70:30 | 80:20 | 50:50 | 60:40 | 70:30 | 80:20 |
| 0 | Amorphous | Amorphous | Amorphous | Amorphous | Amorphous | Amorphous | Amorphous | Amorphous |
| 1 week | Amorphous | Amorphous | Crystalline | Crystalline | Amorphous | Amorphous | Amorphous | Crystalline |
| 2 weeks | Amorphous | Amorphous | Crystalline | Crystalline | Amorphous | Crystalline | Crystalline | Crystalline |
| 4 weeks | Amorphous | Amorphous | Crystalline | Crystalline | Amorphous | Crystalline | Crystalline | Crystalline |

As shown in Table 4, each ASD was amorphous post-electrospray processing. After one week on stability at 50° C./80% RH, the ASDs with a lower drug load (Nilotinib:EUDRAGIT L100-55 at 50:50 and 60:40; Nilotinib:HPMC-AS at 50:50, 60:40 and 70:30) remained amorphous; however, the ASDs with a higher drug load had begun to show signs of crystallization in the XRD scans. Only the ASD formulations with the lowest drug loads (Nilotinib:EUDRAGIT L100-55 at 50:50 and 60:40; Nilotinib:HPMC-AS at 50:50) were amorphous at week 2, and remained amorphous throughout the entire four-week study; all other ASDs showed the presence of crystalline peaks by week 2. Despite the fact that crystallinity was observed after some time for many of these ASDs, this result was considered promising because of the harsh accelerated storage conditions (which are not reflective of real-world storage conditions).

Water Content

Water content was determined by Karl Fischer coulometric titration method, using a Mettler Toledo C30S Karl Fischer with Stromboli Oven Sampler. Approximately 40-50 mg of ASD powder was weighed into a glass Stromboli sample vial and vial was immediately sealed. The vial was then placed onto instrument and analysis was conducted using nitrogen carrier gas. Instrument details and measurement conditions are specified in Table 5.

TABLE 5

Karl Fisher instrument and measurement conditions

| Parameter | Condition |
|---|---|
| Drift duration | 3 min |
| Drift wait time | 60 sec |
| Maximum drift allowance | 25 μg/min |

TABLE 5-continued

Karl Fisher instrument and measurement conditions

| Parameter | Condition |
|---|---|
| Oven temperature | 110° C. |
| Mix time | 60 sec |
| Stir speed | 50% |

The initial moisture levels were very consistent for all eight ASDs, as shown in Table 6. Likewise, all ASDs demonstrated a rapid increase in water content after exposure for one week to high humidity, which leveled off and remained fairly constant (3.5%-5%) for the remainder of the study. Despite some variability in the data, the ASDs comprising either EUDRAGIT L100-55 or HPMC-AS exhibited some hygroscopic character.

TABLE 6

Summary of ASD water content (KF) data for ASDs of Example 1.

| Time Point | Nilotinib:EUDRAGIT L100-55 | | | | Nilotinib: HPMC-AS | | | |
|---|---|---|---|---|---|---|---|---|
| | 50:50 | 60:40 | 70:30 | 80:20 | 50:50 | 60:40 | 70:30 | 80:20 |
| 0 | 0.7% | 1.3% | 1.2% | 1.2% | 1.2% | 1.2% | 1.2% | 1.2% |
| 1 week | 4.4% | 4.1% | 4.1% | 4.5% | 4.7% | 5.1% | 4.8% | 3.5% |
| 2 weeks | 4.6% | 3.9% | 4.0% | 4.1% | 5.4% | 4.9% | 4.9% | 3.7% |
| 4 weeks | 4.1% | 4.1% | 4.3% | 4.5% | 4.6% | 4.1% | 4.1% | 4.1% |

Glass Transition Temperature

Modulated differential scanning calorimetry (mDSC) analysis was run on a TA Instruments Model Q200, equipped with a RCS90 refrigerated cooling system, to assess glass transition temperatures. In general, about 5-10 mg of ASD powder was loaded in a TA $T_{zero}$ low-mass aluminum pan and sealed with a $T_{zero}$ lid. Instrument details and measurement conditions are specified in Table 7. Results are provided in Table 8.

TABLE 7

TA Q200 DSC instrument and measurement conditions.

| Parameter | Condition |
|---|---|
| DSC Model | Modulated |
| Test | MD SC heat only |
| Method | Modulate ±0.48° C. every 60 sec<br>Temperature ramp 3° C./min from 0° C. to 200° C. |
| Data sampling interval | 0.20 sec |

TABLE 8

Summary of observed glass transition temperature (DSC) data ($T_g$) for ASDs of Example 1.

| Time Point | Nilotinib:EUDRAGIT L100-55 | | | | Nilotinib:HPMC-AS | | | |
|---|---|---|---|---|---|---|---|---|
| | 50:50 | 60:40 | 70:30 | 80:20 | 50:50 | 60:40 | 70:30 | 80:20 |
| 0 | 131.3° C. | 130.1° C. | 124.5° C. | 103.2° C. | 101.2° C. | 100.6° C. | 99.1° C. | 98.1° C. |
| 1 week | 133.5° C. | 132.7° C. | 126.5° C. | 115.7° C. | 101.0° C. | 100.5° C. | 98.8° C.[1] | ND |
| 2 weeks | 134.9° C. | 131.6° C. | 124.3° C. | 116.7° C. | 101.5° C. | 100.2° C. | 98.6° C.[1] | ND |
| 4 weeks | 135.4° C. | 134.8° C. | 126.2° C. | 117.0° C. | 100.2° C. | ND | ND | ND |

[1] possible second $T_g$ observed near 60° C.
ND = none detected

As can be seen from the results in Table 8, the ASDs comprising EUDRAGIT L100-55 exhibited decreasing $T_g$ value with increasing drug load. For all four drug load levels, there was essentially no change in $T_g$ on stability.

In the case of the ASDs comprising HPMC-AS, $T_g$ values were similar across the four drug-load levels. The 60:40 ASD had stable $T_g$ for the first two weeks; however, no $T_g$ was detected at four weeks. The 70:30 ASD also had a stable $T_g$ for the first two weeks; however, a weak thermal event that may indicate a second $T_g$ near 60° C. was observed, suggesting that the sample may have been undergoing a phase separation while on stability. No $T_g$ could be detected for the 80:20 ASD sample on stability. The lack of a measurable $T_g$ for these samples suggested that some type of physical change may have occurred with the HPMC-AS ASDs held under accelerated conditions during stability testing.

Assay Related Substances

Assay and related substances (e.g., impurities) were determined using an Agilent 1200 HPLC utilizing an Agilent Poroshell C18 3.0 mm×150 mm×2.7 μm column. Sample solutions of each ASD were prepared by accurately weighing approximately 50 mg of ASD powder into a 50 ml volumetric flask. The ASD powder was initially dissolved in a flask in approximately 40 ml of methanol, and then the flask was vortexed and sonicated until the ASD powder was completely dissolved. The sample flasks were then brought to volume with methanol and mixed well. This sample solution was then diluted 10× in diluent (50:50 acetonitrile (ACN):0.1% phosphoric acid in water). The final concentration of the analyte (nilotinib) in the sample was approximately 0.05 mg/ml. The instrument and measurement conditions are specified in Table 9, while the gradient profile is listed in Table 10.

TABLE 9

HPLC instrument and measurement conditions.

| Parameter | Condition |
|---|---|
| Mobile Phase A | 0.29% TEA and 0.1% AA in water |
| Mobile Phase B | 0.29% TEA and 0.1% AA in acetonitrile |
| Flow | 0.5 ml/min, gradient |
| Injection volume | 16.0 μL |
| Column temperature | 45° |
| Wavelength | 260 nm |
| Run-time | 40 min |

TEA = triethylamine
AA = acetic acid

TABLE 10

HPLC instrument gradient profile.

| Time (min) | % Mobile Phase A | % Mobile Phase B |
|---|---|---|
| 0 | 80.0 | 20.0 |
| 5 | 80.0 | 20.0 |
| 30 | 20.0 | 80.0 |
| 35 | 20.0 | 80.0 |
| 36 | 80.0 | 20.0 |
| 40 | 80.0 | 20.0 |

Assay results are provided in Table 11. Assay values for the ASDs comprising EUDRAGIT L100-55 (96.2%-98.4%) and the ASDs comprising HPMC-AS (96.5%-97.9%) were as expected given the relatively high total related substances levels observed for the as-supplied drug substance (~2%) and the measured initial water content of the ASD samples (~1%). In general, all ASDs demonstrated a decrease in assay over time on stability. This decrease was more pronounced for the ASDs comprising HPMC-AS as compared to the ASDs comprising EUDRAGIT L100-55. With reference to Table 6, increased moisture content was likely responsible for some of the measured potency loss, as ASDs on stability were found to contain between 4%-5% water after one week, and assay measurements were not corrected for water content. Nilotinib peaks were abundant enough to enable determination of percent impurities for each sample.

TABLE 11

Summary of assay (HPLC) data for ASDs of Example 1.

| Time Point | Nilotinib:EUDRAGIT L100-55 | | | | Nilotinib:HPMC-AS | | | |
|---|---|---|---|---|---|---|---|---|
| | 50:50 | 60:40 | 70:30 | 80:20 | 50:50 | 60:40 | 70:30 | 80:20 |
| 0 | 98.0% | 96.3% | 96.2% | 98.4% | 100.8% | 97.9% | 97.2% | 96.5% |
| 1 week | 96.0% | 93.9% | 94.8% | 92.7% | 96.7% | 92.9% | 93.7% | 94.4% |

TABLE 11-continued

Summary of assay (HPLC) data for ASDs of Example 1.

| Time Point | Nilotinib:EUDRAGIT L100-55 | | | | Nilotinib:HPMC-AS | | | |
|---|---|---|---|---|---|---|---|---|
| | 50:50 | 60:40 | 70:30 | 80:20 | 50:50 | 60:40 | 70:30 | 80:20 |
| 2 weeks | 91.4% | 95.7% | 95.5% | 94.0% | n/a | 91.9% | 95.0% | 94.3% |
| 4 weeks | 87.1% | 91.1% | 91.2% | 93.3% | 91.8% | 87.2% | 91.3% | 85.7% | n/a - data not available

Related substances results are provided in Table 12. Levels of related substances were similar for all eight ASDs at all time points. Based on this data, the electrospray process did not appear to increase the level of related substances, and all ASDs appeared chemically stable under accelerated conditions on stability despite exposure to high levels of heat and humidity.

TABLE 12

Summary of total related substances (HPLC) data for ASDs of Example 1.

| Time Point | Nilotinib:EUDRAGIT L100-55 | | | | Nilotinib:HPMC-AS | | | |
|---|---|---|---|---|---|---|---|---|
| | 50:50 | 60:40 | 70:30 | 80:20 | 50:50 | 60:40 | 70:30 | 80:20 |
| 0 | 1.9% | 2.2% | 2.0% | 1.9% | 1.9% | 2.1% | 2.1% | 1.9% |
| 1 week | 1.8% | 2.4% | 2.1% | 2.1% | 1.6% | 2.3% | 2.3% | 2.0% |
| 2 weeks | 1.8% | 2.3% | 2.1% | 2.0% | 1.9% | 2.2% | 2.3% | 2.0% |
| 4 weeks | 1.8% | 2.4% | 1.9% | 1.9% | 1.7% | 2.2% | 2.3% | 2.0% |

Example 2. Stability of Nilotinib ASD Under Accelerated Storage Conditions

A study was performed to evaluate the stability of a nilotinib ASD according to embodiments of the present disclosure under different accelerated storage conditions.

The ASD was prepared similarly to the ASDs described in Example 1, except the solvent mixture was tetrahydrofuran and methanol in a 60:40 (v/v) ratio. (The tetrahydrofuran was stabilized with a small quantity of BHT as an antioxidant; therefore, the ASDs prepared in this example will contain a small, unquantified amount of BHT along with nilotinib and polymer.) Equal quantities of nilotinib and HPMC-AS were dissolved in the solvent mixture to prepare a liquid feedstock, which was electrosprayed to provide the ASD powder.

The resulting ASD powder contained nilotinib and HPMC-AS in a ratio of 50:50 (w/w), and was stored under accelerated conditions at 25° C./60% RH for 24 months, and at 40° C./75% RH for six months. The ASD powder was assessed for each storage condition at t=0 and at 1 month, 2 months, 3 months, and 6 months for amorphicity (XRD), water content (Karl Fisher), glass transition temperature (DSC), and assay/related substances (HPLC). For the samples stored at 25° C./60% RH, additional assessments were done at later time points up to 24 months.

Amorphicity

Amorphicity was assessed as in Example 1, above. The ASD remained amorphous throughout the entire stability study for both sets of storage conditions.

Water Content

Water content was measured by coulometric Karl Fischer titration, as in Example 1, except that sample size was approximately 50-100 mg of ASD powder.

As indicated in Table 13, water content remained substantially consistent across stability timepoints, and no adverse hygroscopicity is observed for the ASDs.

TABLE 13

Summary of water content (KF) data for ASD of Example 2.

| Time Point (months) | Storage Condition | |
|---|---|---|
| | 25° C./60% RH | 40° C./75% RH |
| 0 | 1.52% | 1.52% |
| 1 | 3.25% | 3.71% |
| 2 | 3.41% | 3.63% |
| 3 | 3.37% | 3.51% |
| 6 | 3.15% | 3.70% |
| 9 | 0.88% | |
| 12 | 2.82% | |

Glass Transition Temperature

Glass transition temperature ($T_g$) of the ASD stored under accelerated conditions was assessed as in Example 1. Results are provided in Table 14.

TABLE 14

Summary of glass transition (mDSC) data ($T_g$) for ASD of Example 2

| Time Point (months) | Storage Condition | |
|---|---|---|
| | 25° C./60% RH | 40° C./75% RH |
| 0 | 98.8° C. | 98.8° C. |
| 1 | 101.7° C. | 101.2° C. |
| 2 | 101.4° C. | 101.4° C. |
| 3 | 100.1° C. | 102.8° C. |
| 6 | 100.2° C. | 102.3° C. |
| 9 | 100.6° C. | |
| 12 | 99.7° C. | |
| 18 | 100.5° C. | |
| 24 | 100.6° C. | |

The results show that, for each storage condition, the glass transition temperature of the ASD was generally unchanged over time, which indicates that the ASD was physically stable.

Assay/Related Substances

Assay and related substances (e.g., impurities) of the ASD were assessed through TPLC, utilizing an Agilent Poroshell HPH-C18 3.0 mm×150 mm×2.7 μm column. Sample solutions were prepared by accurately weighing approximately the equivalent of 10 mg of the ASD powder into a 100 ml volumetric flask. The ASD powder was dissolved in approximately 90 ml of methanol (MeOH):water (80:20). The sample flasks were then brought to volume with 80:20 MeOH:water and mixed well until the ASD powder was fully dissolved. The final concentration of the analyte (nilotinib) in the sample was approximately 0.1 mg/ml. The instrument and measurement conditions are specified in Table 15, while the gradient profile is listed in Table 16.

TABLE 15

HPLC instrument and measurement conditions.

| Parameter | Condition |
|---|---|
| Column | Agilent Poroshell HPH-C18, 3.0 mm × 150 mm × 2.7 μm |
| Flow rate | 0.5 ml/min |
| Mobile Phase A | 20 mM ammonium bicarbonate, pH 9.0 |
| Mobile Phase B | ACN:MeOH (80:20) |
| Mobile Phase C | ACN:MeOH (90:10) |
| Elution program | Gradient |
| Injection Volume | 5 μL (assay); 10 μL (related substances) |
| Column Temperature | 45° C. |
| Detector Wavelength | 260 nm |

TABLE 16

HPLC instrument gradient program.

| Analysis | Time (min) | % Mobile Phase A | % Mobile Phase B |
|---|---|---|---|
| Assay Method | 0 | 55 | 45 |
| | 7 | 30 | 70 |
| | 8 | 0 | 100 |
| | 9 | 0 | 100 |
| | 9.1 | 55 | 45 |
| | 12 | 55 | 45 |
| Related Substances Method | 0 | 90 | 10 |
| | 2 | 90 | 10 |
| | 5 | 65 | 35 |
| | 35 | 52 | 48 |
| | 40 | 0 | 100 |
| | 41 | 0 | 100 |
| | 41.1 | 90 | 10 |
| | 44 | 90 | 10 |

Assay values were determined for the ASD post-spray (t=0) and at designated stability timepoints under each storage condition. Measured assay values of the ASD for each storage condition are listed in Table 17. The reported assay values are not corrected for water content.

TABLE 17

Summary of assay (HPLC) data for ASD of Example 2.

| Time Point | Storage Condition | |
|---|---|---|
| (months) | 25° C./60% RH | 40° C./75% RH |
| 0 | 95.8% | 95.8% |
| 1 | 93.5% | 93.7% |
| 2 | 95.0% | 94.7% |
| 3 | 95.5% | 95.3% |
| 6 | 95.6% | 96.4% |
| 9 | 97.7% | |
| 12 | 95.0% | |
| 18 | 93.3% | |
| 24 | 94.4% | |

Total related substances measured values for the ASD under each storage condition are listed in Table 18.

TABLE 18

Summary of total related substances (HPLC) data for ASD of Example 2

| Time Point | Storage Condition | |
|---|---|---|
| (months) | 25° C./60% RH | 40° C./75% RH |
| 0 | 0.60% | 0.60% |
| 1 | 0.56% | 0.63% |
| 2 | 0.72% | 0.81% |

TABLE 18-continued

Summary of total related substances (HPLC) data for ASD of Example 2

| Time Point | Storage Condition | |
|---|---|---|
| (months) | 25° C./60% RH | 40° C./75% RH |
| 3 | 0.80% | 0.78% |
| 6 | 0.52% | 0.57% |
| 9 | 0.68% | |
| 12 | 0.71% | |
| 18 | 0.62% | |
| 24 | 0.71% | |

As demonstrated in Tables 17 and 18, the ASD exhibited suitably high assay values and suitably low related substances values that did not appreciably change over time, indicating that the ASD was chemically stable.

Example 3. Stability of Nilotinib ASD Suspension Formulations

A study was performed to evaluate the stability of two pharmaceutical compositions according to embodiments of the disclosure, in the form of suspensions. The components of the two pharmaceutical compositions, labeled as "Composition 1" and "Composition 2", are shown in Table 19.

TABLE 19

Components of the pharmaceutical compositions for Example 3.

| Components | Composition 1 | Composition 2 |
|---|---|---|
| Nilotinib ASD (Nilotinib:HPMC-AS 50:50 w/w) | 11.340 g | 11.340 g |
| SOLUPLUS (solubilizer) | - 0 - | 5.5625 g |
| 0.5% methylcellulose in 0.5 mM citric acid buffer (pH 4) (carrier) | 435 ml | 435 ml |

The ASD powder contained nilotinib free base (49.78% by weight of the ASD), HPMC-AS (49.78%), and BHT (0.44%). (The BHT amount was quantitated by analysis of the as-prepared ASD.) Composition 1 was prepared by mixing the ASD powder into 0.5% methylcellulose in 0.5 mM citric acid buffer to form a suspension. Composition 2 was prepared by mixing the ASD and the SOLUPLUS (commercially available from BASF North America) until blended, and then mixing into the 0.5% methylcellulose in 0.5 mM citric acid buffer to form a suspension. For both compositions, the nominal concentration of nilotinib was 12.5 mg/ml.

Each composition was stored in a closed container on a bench at standard room temperature and humidity throughout this study. The assay of each pharmaceutical composition was assessed over a 4-hour period by HPLC as described above for Example 2. The measured assay values for each pharmaceutical composition are provided in Table 20.

TABLE 20

Summary of suspension assay data over a 24-hour period for compositions of Example 3.

| Time Point (hours) | Composition 1 | Composition 2 |
|---|---|---|
| 0 | 101.7% | 99.0% |
| 2 | 102.7% | 99.0% |
| 4 | 99.9% | 98.1% |

Amorphicity of each pharmaceutical composition was assessed by XRD as described above for Example 1 at T=0, 2, and 4. Both pharmaceutical compositions remained amorphous throughout the entire stability study, regardless of the presence or absence of SOLUPLUS.

Example 4. Canine In Vivo Studies

Studies were performed in beagle dogs to investigate the impact of stomach pH and food on the in vivo exposure obtained using pharmaceutical compositions of the disclosure (formulated as a suspension, capsule, and tablet) compared to exposures obtained by dosing a conventional immediate-release formulation of nilotinib, such as TASIGNA IR Capsule.

For selected conditions, the studies incorporated pretreatments to adjust the stomach pH of the dogs prior to dosing. Based on published protocols, pretreatment of the canines with pentagastrin would control the pH to a range between 1 and 2, while pretreatment with a phosphate buffer would achieve a pH between 2 and 3.

The study design is provided in Table 21. For Legs A1 and A3, a suspension ("TASIGNA Suspension") was prepared at a nilotinib concentration of 10 mg/mL using the decanted contents of TASIGNA IR Capsules, in a vehicle comprising 0.5% methylcellulose in 0.5 mM citric acid buffer (pH 4). For Leg B1, a quantity of decanted contents in powder form from TASIGNA IR Capsules was weighed to accurately provide a dose of 5 mg/kg, and the weighed powder was then filled into a conventional gelatin capsule for dosing ("TASIGNA Capsule").

Legs B2, B3, B4, C2, and C3 employed an ASD comprising nilotinib and HPMC-AS in a nilotinib:HPMC-AS ratio of 50:50 (w/w) (prepared as in Example 2 above), in a suitable pharmaceutical composition, prepared as follows. For Leg B2, the ASD was mixed with suitable excipients and formulated into granules (nilotinib drug load of 15%) by slugging; a suitable quantity of granules was then filled into a conventional gelatin capsule for dosing ("ASD Capsule"). For Legs B3 and C3, an ASD suspension was prepared according to Composition 1 of Example 3 (Table 19). For Leg B4, granules (as for Leg B2) were combined with conventional excipients and manually pressed into a slug tablet (nilotinib drug load of 7.7%) using a tablet press ("ASD Tablet"). For Leg C2, an ASD suspension comprising SOLUPLUS was prepared according to Composition 2 of Example 3 (Table 19).

For Leg C1, an ASD suspension was prepared according to Composition 2 of Example 3 (Table 19), except the nilotinib ASD comprised nilotinib and EUDRAGIT L100-55 in a nilotinib:EUDRAGIT L100-55 ratio of 50:50 (w/w). This suspension had been prepared by electrospraying from a methanol:THF solvent mixture (1:1 v/v).

TABLE 21

Canine in vivo study design for Example 4.

| Study Leg | Study Product | Fed/Fasted | Pretreatment |
|---|---|---|---|
| A1 | TASIGNA Suspension | Fasted | Pentagastrin |
| A3 | TASIGNA Suspension | Fed | None |
| B1 | TASIGNA Capsule | Fasted | Phosphate Buffer |
| B2 | ASD Capsule | Fasted | Phosphate Buffer |
| B3 | ASD suspension (HPMC-AS) (Composition 1) | Fasted | Phosphate Buffer |
| B4 | ASD Tablet | Fasted | Phosphate Buffer |
| C1 | ASD suspension (EUDRAGIT L100-55) with SOLUPLUS | Fasted | Phosphate Buffer |
| C2 | ASD suspension (HPMC-AS) with SOLUPLUS (Composition 2) | Fasted | Phosphate Buffer |
| C3 | ASD suspension (HPMC-AS) (Composition 1) | Fasted | Phosphate Buffer |

All dogs were fasted for a minimum of ten hours prior to dose administration. The animals were supplied with water ad libitum. Each study leg had ten dogs. The study employed a cross-over study design, with the same dogs receiving each dose following a one-week washout period between each leg of the study.

For the fasted legs, food was withheld from the animals for a minimum of twelve hours prior to dosing. In addition, water was removed two hours prior to dosing.

For the fed study Leg A3, animals were acclimated to a high fat meal for five days prior to dosing. Animals were fasted for a minimum of ten hours overnight and then fed a pre-weighed portion (~50 grams) of a puree consisting of McDonald's Bacon and Egg McMuffin. Animals were allowed 30 minutes to consume the food, after which time any remaining food was removed and the test articles administered.

Normal dog chow was provided to the animals four hours post-dose. Water was provided immediately following dosing for all study legs.

In study Leg A1, each dog received an intramuscular injection of pentagastrin (6 µg/kg) approximately 30 minutes prior to dosing to ensure the gastric pH of the fasted animals would be acidic (pH 1-2).

For study legs incorporating a phosphate buffer pretreatment, each dog received 25 mL of 100 mM phosphate buffer (pH 2.5) via gavage tube prior to dosing. After dosing, each dog received an additional 10 mL of the buffer as a flush.

For each study leg, all dogs received the appropriate oral dose of the appropriate study product to deliver 5 mg/kg nilotinib, at t=0. Following dosing, blood samples were collected at 30 minutes, 1, 1.5, 2, 3, 4, 6, 8, 12, 18, and 24 hours.

Pharmacokinetic parameters were calculated from the time course of the plasma concentrations. Pharmacokinetic analysis was conducted by Absorption Systems by a non-compartmental model using Phoenix WinNonlin (v7.0) software. $C_{max}$ and the time to reach maximum plasma drug concentration ($T_{max}$) after dosing were observed from the data. AUC was calculated using the linear trapezoidal rule with calculation to the last quantifiable data point, and with extrapolation to infinity. Plasma half-life ($t_{1/2}$) was calculated from 0.693/slope of the terminal elimination phase. Mean residence time (MRT) was calculated by dividing the area under the moment curve (AUMC) by the AUC. Any samples below the limit of quantitation (0.5 ng/mL) were treated as zero for pharmacokinetic data analysis.

Table 22 provides the key pharmacokinetic parameters calculated from pooled data, and comparisons between select legs of the study are shown in FIGS. 1-4.

TABLE 22

Key pharmacokinetic parameters from canine in vivo studies of Example 4.

| Regimen | $C_{max}$* (ng/ml) | $T_{max}$ (hr) | $t_{1/2}$ (h) | $MRT_{(0\text{-}last)}$ (hr) | $AUC_{(0\text{-}last)}$ (ng · h/ml) | $AUC_{(0\text{-}inf)}$ (ng · h/ml) |
|---|---|---|---|---|---|---|
| Leg A1: TASIGNA Suspension - fasted (pretreat: pentagastrin) | 1215 (403) | 1.8 (0.6) | 4.13 (1-17) | 4.09 (1.19) | 5054 (2432) | 5129 (2514) |
| Leg A3: TASIGNA Suspension - fed (pretreat: none) | 1203 (471) | 2.3 (0.8) | 4.36 (1.34) | 5.08 (1.16) | 6784 (4156) | 6978 (4448) |
| Leg B1: TASIGNA Capsule - fasted (pretreat: phosphate buffer, pH 2.5) | 265 (240) | 2.5 (1.1) | 3.27 (0.804) | 5.35 (1.61) | 1331 (1334) | 1243 (1518) |
| Leg B2: ASD Capsule - fasted (pretreat: phosphate buffer, pH 2.5) | 372 (201) | 2.1 (0.55) | 3.69 (1.27) | 4.62 (0.772) | 1586 (997) | 1619 (1053) |
| Leg B3: ASD suspension (HPMC-AS) - fasted (pretreat: phosphate buffer, pH 2.5) | 661 (277) | 1.5 (0.33) | 3.68 (ill) | 4.53 (1.12) | 3116 (2170) | 3208 (2361) |
| Leg B4: ASD Tablet - fasted (pretreat: phosphate buffer, pH 2.5) | 427 (180) | 1.8 (0.89) | 4.05 (0.998) | 4.60 (0.849) | 1897 (1316) | 1937 (1385) |
| Leg C1: ASD suspension (EUDRAGIT L100-55) with SOLUPLUS - fasted (pretreat: phosphate buffer, pH 2.5) | 948 (482) | 1.8 (0.9) | 3.80 (0.916) | 4.35 (0.958) | 4497 (3478) | 4655 (4306) |
| Leg C2: ASD suspension (HPMC-AS) with SOLUPLUS - fasted (pretreat: phosphate buffer, pH 2.5) | 953 (293) | 1.4 (0.4) | 3.56 (1.15) | 4.34 (1-18) | 4876 (2880) | 5334 (3181) |
| Leg C3: ASD suspension (HPMC-AS) - fasted (pretreat: phosphate buffer, pH 2.5) | 473 (251) | 1.4 (0.7) | 5.11 (4.85) | 5.08 (2.35) | 2337 (1992) | 1617 (801) |

*mean (SD)

As shown in FIG. 1, the TASIGNA Capsule-fasted exposure (Leg B1) was dramatically reduced as compared to the TASIGNA TR Suspension-fasted exposure following pretreatment with pentagastrin (Leg A1). These results demonstrate that the pentagastrin pretreatment increased nilotinib solubility in the dog stomach by reducing the gastric pH, resulting in higher exposure in the fasted state. These results also indicate that the 100 mM phosphate buffer (pH 2.5) pretreatment was effective at creating gastric conditions in the dog that were more discriminating for the TASIGNA Capsule under fasting conditions.

Figure 2:
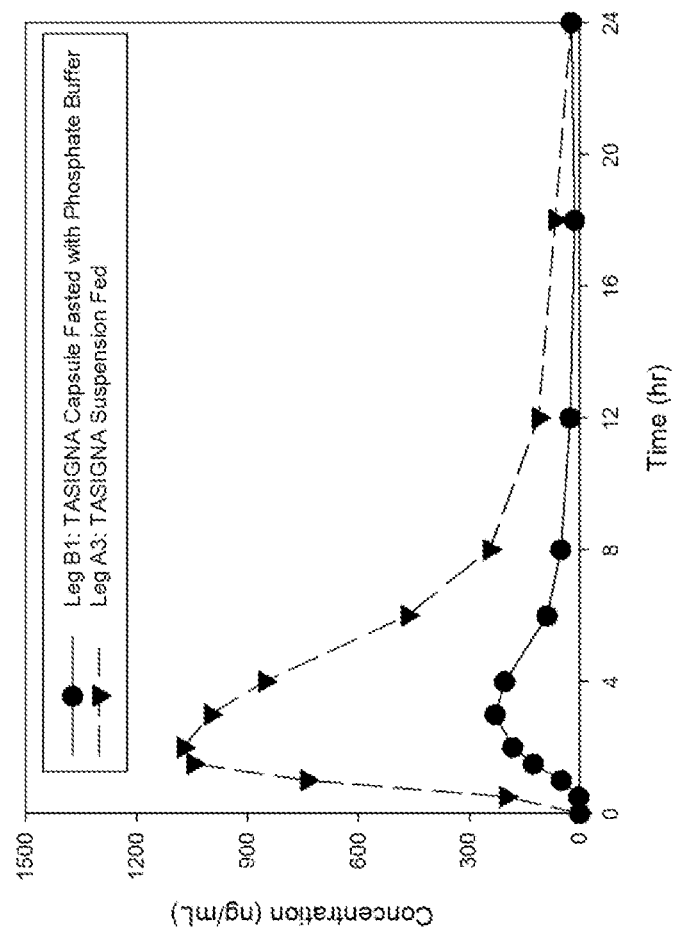
FIG. 2 shows pharmacokinetic profiles for (a) male beagles in a fasted state administered TASIGNA Capsule after pretreatment with phosphate buffer (pH ~2.5) (Leg B1); and (b) male beagles in a fed state administered TASIGNA Suspension (Leg A3); as described in Example 4.

FIG. 2 compares TASIGNA Capsule-fasted exposure (Leg B1) and TASIGNA TR Suspension-fed exposure (Leg A3). These results show that the protocol in this study using phosphate buffer pretreatment was successful at creating conditions that enabled the dog model to successfully demonstrate the known large, positive food effect observed in human for conventional immediate-release nilotinib. A statistical analysis of these results shows that $C_{max}$ (p-value: <0.0001) and AUC (p-value: <0.0019) was significantly greater following fed dosing versus fasted-dosing.

Figure 3:
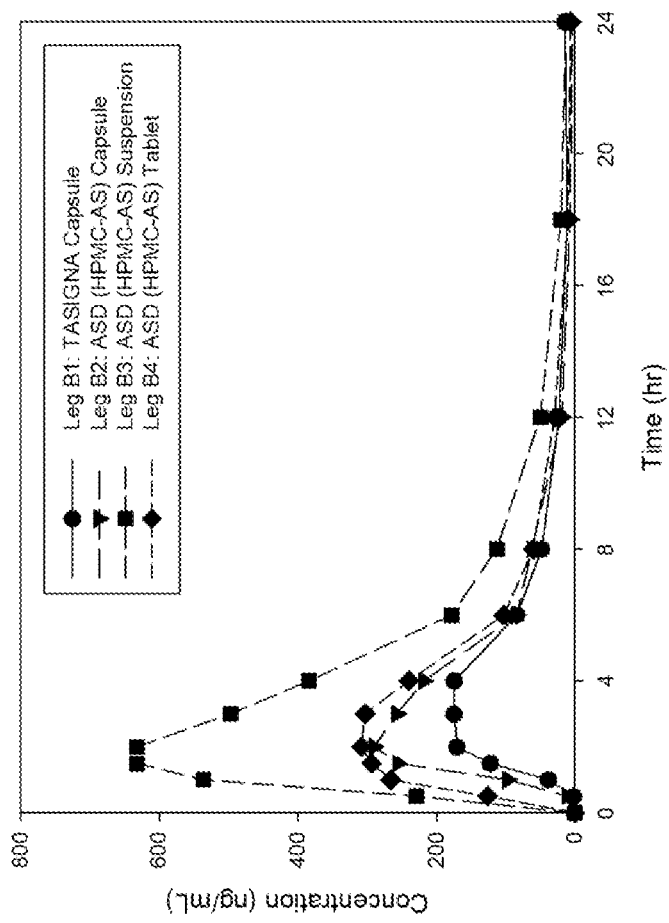
FIG. 3 shows pharmacokinetic profiles for (a) male beagles in a fasted state administered TASIGNA Capsule after pretreatment with phosphate buffer (pH ~2.5) (Leg B1); (b) male beagles in a fasted state administered ASD Capsule (nilotinib and HPMC-AS) after pretreatment with phosphate buffer (pH ~2.5) (Leg B2); (c) male beagles in a fasted state administered ASD Suspension (nilotinib and HPMC-AS) after pretreatment with phosphate buffer (pH ~2.5) (Leg B3); and (d) male beagles in a fasted state administered ASD Tablet (nilotinib and HPMC-AS) after pretreatment with phosphate buffer (pH ~2.5) (Leg B4); as described in Example 4.

FIG. 3 shows the pharmacokinetic profiles for three nilotinib ASD compositions (ASD Capsule—Leg B2; ASD suspension (HPMC-AS)—Leg B3; ASD Tablet—Leg B4), along with the TASIGNA Capsule (Leg B1), under fasting conditions at pH ~2.5. All three ASD compositions demonstrated increased exposure compared to the TASIGNA Capsule under fasting conditions. The ASD Tablet and ASD Capsule showed increases in $C_{max}$ and AUC compared to the TASIGNA Capsule, while the ASD suspension (HPMC-AS) showed significant increases in both $C_{max}$ and AUC.

Figure 4:
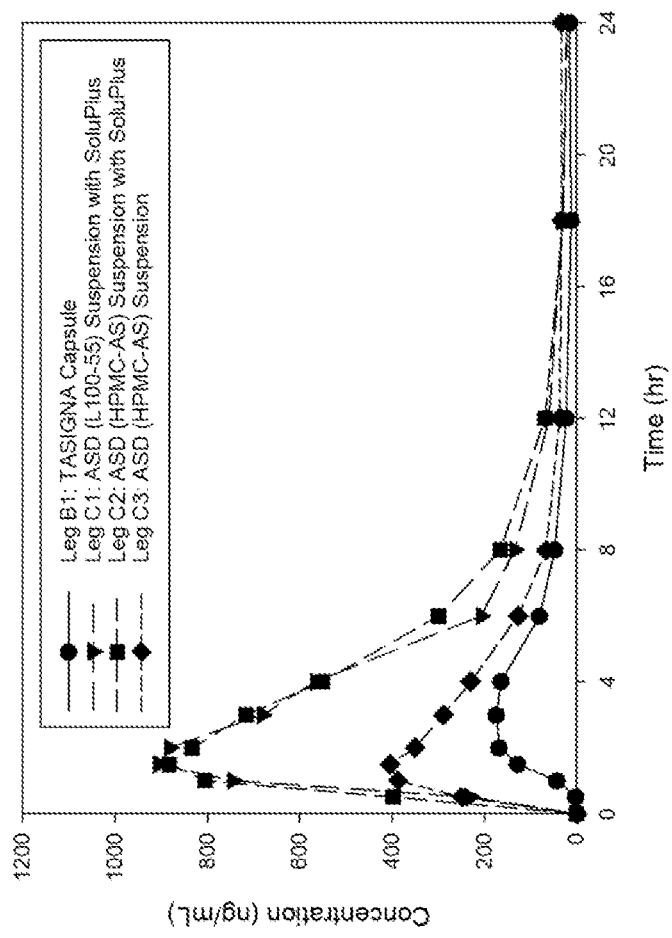
FIG. 4 shows pharmacokinetic profiles for (a) male beagles in a fasted state administered TASIGNA Capsule after pretreatment with phosphate buffer (pH ~2.5) (Leg B1); (b) male beagles in a fasted state administered ASD Suspension (nilotinib and EUDRAGIT L100-55) with SOLUPLUS after pretreatment with phosphate buffer (pH ~2.5) (Leg C1); (c) male beagles in a fasted state administered ASD Suspension (nilotinib and HPMC-AS) with SOLUPLUS after pretreatment with phosphate buffer (pH ~2.5) (Leg C2); and (d) male beagles in a fasted state administered ASD Suspension (nilotinib and HPMC-AS) after pretreatment with phosphate buffer (pH ~2.5) (Leg C3); as described in Example 4.

FIG. 4 shows the pharmacokinetic profiles for three nilotinib ASD suspension compositions (ASD suspension of nilotinib and EUDRAGIT L100-55 with SOLUPLUS—Leg C1; ASD suspension of nilotinib and HPMC-AS with SOLUPLUS—Leg C2; ASD suspension of nilotinib and HPMC-AS—Leg C3), along with the TASIGNA Capsule (Leg B1), administered under fasting conditions at pH ~2.5. All three ASD suspension compositions demonstrated increased exposure compared to the TASIGNA Capsule under fasting conditions. The ASD suspension without SOLUPLUS showed increases in $C_{max}$ and AUC compared to the TASIGNA Capsule, while the two suspension formulations with SOLUPLUS showed significant increases in both $C_{max}$ and AUC.

These results showed that nilotinib ASD according to the disclosure can be used to increase nilotinib exposure in the fasted state, potentially facilitating a lower delivered dose and improved food effect profile compared to the TASIGNA Capsule.

Example 5. Human In Vivo Studies

A study was performed in human subjects to assess the pharmacokinetics observed upon administration of Compositions 1 and 2 of Example 3, as compared to pharmacokinetics observed upon administration of conventional commercially available 200 mg TASIGNA IR Capsule; and to assess the effect of food on the pharmacokinetics observed upon administration of the pharmaceutical compositions.

Healthy subjects (n=26) were orally administered either TASIGNA IR Capsule (200 mg) or an appropriate quantity of Composition 1 or Composition 2 (Example 3) in accordance with the regimens described in Table 23. The study employed a cross-over study design, in which each subject participated in each regimen for each period of the study.

(Note that TASIGNA IR Capsule could not be dosed under fed conditions in accordance with the product's labeling).

TABLE 23

Human in vivo dosing regimens for Example 5.

| Regimen | Study Product | Dose | Administration Condition |
|---------|---------------|------|--------------------------|
| A | TASIGNA IR Capsule | 200 mg | fasted |
| B | Composition 1 | 50 mg | fasted |
| C | Composition 2 | 50 mg | fasted |
| D | Composition 1 | 50 mg | fed |
| E | Composition 2 | 65 mg | fasted |
| F | Composition 2 | 65 mg | fed |

Subjects were screened for inclusion in the study up to 28 days before dosing. Each study period followed the same design. Subjects were admitted to the clinical unit on the morning of the day prior to administration of the study product (Day −1) where eligibility was reviewed and confirmed. After an overnight fast of a minimum of 10 hours, subjects were dosed on the morning of Day 1 of each period, and subjects continued to fast for approximately 4 hours post-dose. For fed regimens, subjects were dosed 30 minutes after the start of a high-fat breakfast. Following oral administration, plasma samples were taken at the following time points to assess the plasma concentration of nilotinib: 0 (prior to administration), 0.5, 1, 2, 3, 4, 5, 6, 8, 10, 12, 18, 24, 36, 48, and 72 hours. Subjects remained on site for the first 48 hours post-dose and returned to the clinical unit for a pharmacokinetic blood sample and safety assessments at 72 hours post-dose. There was a minimum washout of 7 days between each study period.

A subject was considered evaluable for the pharmacokinetic assessment if the subject received the TASIGNA IR Capsule and at least one of test Compositions 1 and 2 in the fasted state, and if pharmacokinetic and safety data up to 72 hours post-dose were obtained. A subject was considered evaluable for the food effect assessment if the subject received at least one of test Compositions 1 and 2 in both the fed and fasted state (i.e., the same composition in both states) at the same dose level, and if pharmacokinetic and safety data up to 72 hours post-dose were obtained.

Figure 5:
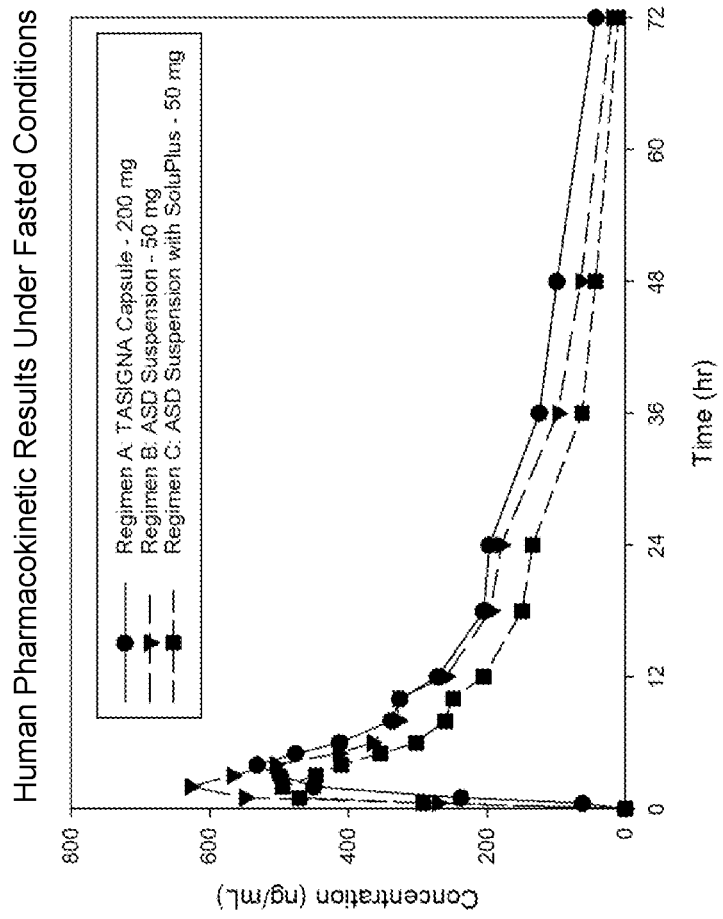
FIG. 5 shows pharmacokinetic profiles for (a) healthy human subjects in a fasted state orally administered 200 mg TASIGNA IR Capsule; (b) healthy human subjects in a fasted state orally administered 50 mg Composition 1 (ASD of nilotinib and HPMC-AS); and (c) healthy human subjects in a fasted state orally administered 50 mg Composition 2 (ASD of nilotinib and HPMC-AS, with SOLUPLUS); as described in Example 5.

Key pharmacokinetic parameters were calculated using pooled data for evaluable subjects (n=24 to 26). Table 24 provides the geometric mean of key pharmacokinetic parameters and Table 25 shows geometric mean of non-dose adjusted relative bioavailabilities ($F_{rel}$) in subjects following administrations of each regimen. A comparison of Regimens A-C (see FIG. 5) shows that Compositions 1 (Regimen B) and 2 (Regimen C) exhibited AUC and $C_{max}$ values that are comparable or higher than the AUC and $C_{max}$ of the 200 mg TASIGNA IR Capsule (Regimen A), despite that the TASIGNA IR Capsule contained 200 mg of nilotinib and Compositions 1 and 2 contained only 50 mg of nilotinib. In addition, Composition 1 (Regimen B), which did not contain SOLUPLUS, exhibited higher AUC and $C_{max}$ values than Composition 2 (Regimen C).

Figure 6:
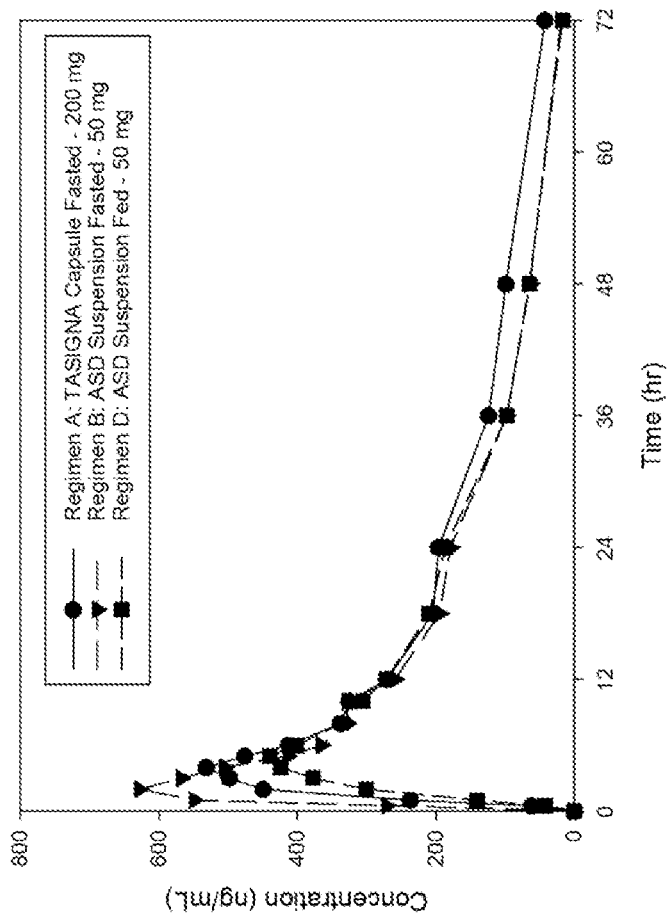
FIG. 6 shows pharmacokinetic profiles for (a) healthy human subjects in a fasted state orally administered 200 mg TASIGNA IR Capsule; (b) healthy human subjects in a fasted state orally administered 50 mg Composition 1 (ASD of nilotinib and HPMC-AS); and (c) healthy human subjects in a fed state orally administered 50 mg Composition 1 (ASD of nilotinib and HPMC-AS); as described in Example 5.

A comparison among Regimens B and D (see FIG. 6) shows that administration of the nilotinib pharmaceutical compositions under fed conditions did not result in appreciably elevated nilotinib plasma concentration levels relative to administration under fasting conditions, as the concentration levels and key pharmacokinetic parameters resulting from Regimen D (50 mg of Composition 1 administered under fed conditions) were not significantly greater than those resulting from Regimen B (50 mg of Composition 1 administered under fasting conditions) (see FIG. 6, Tables 24 and 25).

Figure 7:
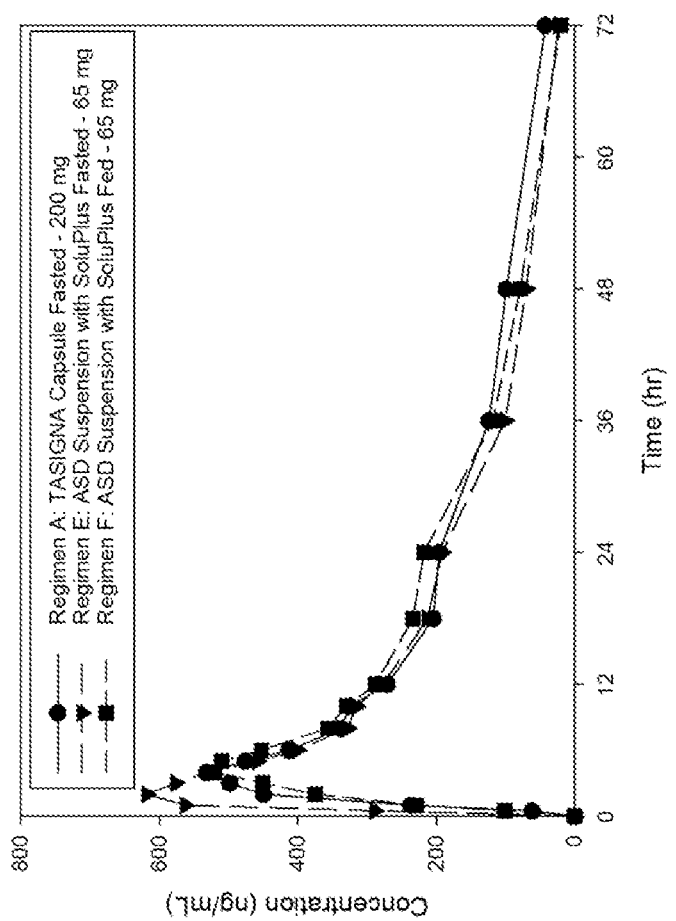
FIG. 7 shows pharmacokinetic profiles for (a) healthy human subjects in a fasted state orally administered 200 mg TASIGNA IR Capsule; (b) healthy human subjects in a fasted state orally administered 65 mg Composition 2 (ASD of nilotinib and HPMC-AS, with SOLUPLUS); and (c) healthy human subjects in a fed state orally administered 65 mg Composition 2 (ASD of nilotinib and HPMC-AS, with SOLUPLUS); as described in Example 5.

A similar result is evident in the comparison of Regimens E and F (see FIG. 7), as the nilotinib plasma concentration levels and key pharmacokinetic parameters resulting from Regimen F (65 mg of Composition 1 administered under fed conditions) are similar or lower than the nilotinib plasma concentration levels and key pharmacokinetic parameters resulting from Regimen E (65 mg of Composition 2 administered under fed conditions) (see Tables 24 and 25). These results are surprising in light of the food effect associated with conventional commercially available immediate-release compositions of nilotinib (such as TASIGNA IR Capsule) that is known in the art.

TABLE 24

Geometric mean (coefficient of variation, or CV %) key pharmacokinetic parameters of nilotinib in healthy volunteers following oral administration of TASIGNA IR Capsule and select nilotinib ASD compositions according to embodiments of the disclosure.

| Regimen | $T_{max}$* (h) | $C_{max}$ (ng/ml) | $AUC_{(0-12)}$ (ng · h/ml) | $AUC_{(0-24)}$ (ng · h/ml) | $AUC_{(0-last)}$ (ng · h/ml) | $AUC_{(0-inf)}$ (ng · h/ml) | $t_{1/2}$ (h) |
|---------|----------------|-------------------|----------------------------|----------------------------|------------------------------|-----------------------------|---------------|
| A: 200 mg TASIGNA IR Capsule - fasted | 4.00 (2.00-6.00) | 537 (39.5) | 4170 (35.4) | 6620 (38.4) | 11100 (45.3) | 12600 (53.6) | 19.8 (62.3) |
| B: 50 mg Nilotinib ASD Composition 1 - fasted | 2.00 (1.00-5.00) | 621 (27.4) | 4670 (22.2) | 7050 (25.2) | 10200 (38.3) | 10500 (42.3) | 12.4 (42.3) |
| C: 50 mg Nilotinib ASD Composition 2 - fasted | 2.00 (1.00-5.00) | 501 (25.9) | 3790 (23.0) | 5590 (28.5) | 7610 (40.1) | 7760 (42.1) | 11.3 (30.8) |
| D: 50 mg Nilotinib ASD Composition 1 - fed | 4.00 (3.00-12.00) | 456 (19.9) | 3770 (18.6) | 6310 (23.3) | 9490 (38.6) | 9840 (4E3) | 12.9 (33.5) |
| E: 65 mg Nilotinib ASD Composition 2 - fasted | 2.00 (1.00-4.00) | 616 (25.5) | 4820 (24.0) | 7340 (29.5) | 10600 (44.4) | 11000 (48.9) | 13.2 (42.1) |
| F: 65 mg Nilotinib ASD Composition 2 - fed | 4.50 (3.00-6.00) | 525 (23.0) | 4320 (22.2) | 7130 (25.7) | 11000 (39.6) | 11300 (42.4) | 12.4 (33.9) |

*median (range)

TABLE 25

Geometric mean (CV%) non-dose adjusted relative bioavailabilities ($F_{rel}$) of nilotinib in healthy volunteers following oral administration of nilotinib ASD compositions according to the disclosure.

| Regimen | Comparator | $F_{rel}$ $C_{max}$ (%) | $F_{rel}$ $AUC_{(0-last)}$ (%) | $F_{rel}$ $AUC_{(0-inf)}$ (%) |
|---|---|---|---|---|
| B: 50 mg Nilotinib ASD Composition 1 - fasted | A: 200 mg TASIGNA IR Capsule - fasted | 116 (28.1) | 91.9 (26.0) | 83.4 (28.6) |
| C: 50 mg Nilotinib ASD Composition 2 - fasted | A: 200 mg TASIGNA IR Capsule - fasted | 93.3 (31.8) | 68.7 (26.5) | 61.6 (24.7) |
| D: 50 mg Nilotinib ASD Composition 1 - fed | B: 50 mg Nilotinib ASD Composition 1 - fasted | 74.3 (22.2) | 92.5 (17.9) | 92.5 (18.7) |
| E: 65 mg Nilotinib ASD Composition 2 - fasted | A: 200 mg TASIGNA IR Capsule - fasted | 111 (30.1) | 93.4 (29.1) | 86.9 (31.9) |
|  | B: 50 mg Nilotinib ASD Composition 1 - fasted | 99.6 (17.8) | 103 (18.9) | 104 (20.3) |
| F: 65 mg Nilotinib ASD Composition 2 - fed | A: 200 mg TASIGNA IR Capsule - fasted | 94.8 (38.0) | 96.6 (28.8) | 89.3 (30.3) |
|  | E: 65 mg Nilotinib ASD Composition 2 - fasted | 85.2 (16.6) | 103 (15.4) | 103 (16.7) |

The foregoing description is given for clearness of understanding only, and no unnecessary limitations should be understood therefrom. Various modifications and alterations to this disclosure will become apparent to those skilled in the art without departing from the scope and spirit of this disclosure. It should be understood that this disclosure is not intended to be unduly limited by the illustrative embodiments and examples set forth herein, and such examples and embodiments are presented by way of example only.

Reference throughout this specification to "one embodiment," "an embodiment," "certain embodiments," or "some embodiments," etc., means that a particular feature, configuration, composition, or characteristic described in connection with the embodiment is included in at least one embodiment of the disclosure. Thus, the appearances of such phrases in various places throughout this specification are not necessarily referring to the same embodiment of the disclosure. Furthermore, the particular features, configurations, compositions, or characteristics may be combined in any suitable manner in one or more embodiments.

Throughout the specification, where compositions are described as including components or materials, it is contemplated that the compositions can also consist essentially of, or consist of, any combination of the recited components or materials, unless described otherwise. Likewise, where methods are described as including particular steps, it is contemplated that the methods can also consist essentially of, or consist of, any combination of the recited steps, unless described otherwise.

The practice of a method disclosed herein, and individual steps thereof, can be performed manually and/or with the aid of or automation provided by electronic equipment. Although processes have been described with reference to particular embodiments, a person of ordinary skill in the art will readily appreciate that other ways of performing the acts associated with the methods may be used. For example, the order of various steps may be changed without departing from the scope or spirit of the method, unless described otherwise. In addition, some of the individual steps can be combined, omitted, or further subdivided into additional steps.

The term "comprises" and variations such as "comprises" and "comprising" do not have a limiting meaning where these terms appear in the description and claims. Such terms will be understood to imply the inclusion of a stated step or element or group of steps or elements but not the exclusion of any other step or element or group of steps or elements.

By "consists of" (or similarly "consisting of") is meant including, and limited to, whatever follows the phrase "consists of" Thus, the phrase "consists of" in dictates that the listed elements are required or mandatory, and that no other elements may be present. By "consists essentially of" (or similarly "consisting essentially of") is meant including any elements listed after the phrase, and limited to other elements that do not interfere with or contribute to the activity or action specified in the disclosure for the listed elements. Thus, the phrase "consists essentially of" indicates that the listed elements are required or mandatory, but that other elements are optional and may or may not be present depending upon whether or not they materially affect the activity or action of the listed elements.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure.

In this application, terms such as "a," "an," and "the" are not intended to refer to only a singular entity, but include the general class of which a specific example may be used for illustration. The terms "a," "an," and "the" are used interchangeably with the term "at least one." The phrases "at least one of" and "comprises at least one of" followed by a list refer to any one of the items in the list and any combination of two or more items in the list.

As used herein, the term "or" is generally employed in its usual sense including "and/or" unless the content clearly dictates otherwise. The term "and/or" means one or all of the listed elements or a combination of any two or more of the listed elements (e.g., preventing and/or treating an affliction means preventing, treating, or both treating and preventing further afflictions).

Also herein, all numbers are assumed to be modified by the term "about" and preferably by the term "exactly." As used herein in connection with a measured quantity, the term "about" refers to that variation in the measured quantity as would be expected by the skilled artisan making the measurement and exercising a level of care commensurate with the objective of the measurement and the precision of the measuring equipment used. Herein, "up to" a number (e.g., up to 50) includes the number (e.g., 50). Also herein, the recitations of numerical ranges by endpoints include all numbers subsumed within that range as well as the endpoints (e.g., 1 to 5 includes 1, 1.5, 2, 2.75, 3, 3.80, 4, 5, etc.) and any sub-ranges (e.g., 1 to 5 includes 1 to 4, 1 to 3, 2 to 4, etc.).

The complete disclosures of the patents, patent documents, and publications cited herein are incorporated by reference in their entirety as if each were individually incorporated. To the extent that there is any conflict or discrepancy between the present disclosure and the disclosure in any document that is incorporated by reference, this disclosure as written will control.

What is claimed is:

1. A treatment regimen for treating a proliferative disorder in a patient in need thereof, the regimen comprising:
   (a) administering to the patient a first dose, the first dose comprising a standard dosage of a proton pump inhibitor; and
   (b) within 10 hours after the first dose, administering a second dose to the patient, the second dose comprising a pharmaceutical composition comprising an amorphous solid dispersion, the amorphous solid dispersion comprising nilotinib and one or more polymers, wherein the one or more polymers comprises an anionic polymer comprising phthalate functionality;
   wherein the nilotinib and the anionic polymer comprising phthalate functionality are present in the amorphous solid dispersion in a w/w ratio of 20:80 to 95:5 (nilotinib:polymer);
   wherein the amount of nilotinib in the second dose is 50 to 80% less than a dose required for delivering a therapeutically effective amount of nilotinib in the fasted state using a conventional immediate-release crystalline nilotinib formulation; and
   wherein the second dose provides a therapeutically relevant exposure of nilotinib to the patient.

2. The treatment regimen of claim 1, wherein the proliferative disorder is Philadelphia chromosome positive chronic myeloid leukemia.

3. The treatment regimen of claim 1, wherein the first dose comprises a standard dosage of a proton pump inhibitor selected from rabeprazole, esomeprazole, lansoprazole, omeprazole, pantoprazole, dexlansoprazole, or a combination thereof.

4. The treatment regimen of claim 1, wherein the first dose comprises a standard dosage of omeprazole.

5. The treatment regimen of claim 1, wherein the second dose is administered within 4 hours after the first dose.

6. The treatment regimen of claim 1, wherein the second dose is administered within 2 hours after the first dose.

7. The treatment regimen of claim 1, wherein the first dose and the second dose are administered concurrently.

8. The treatment regimen of claim 1, wherein the nilotinib is present in the amorphous solid dispersion as nilotinib free base or nilotinib hydrochloride.

9. The treatment regimen of claim 1, wherein the anionic polymer comprising phthalate functionality includes hydroxypropyl methylcellulose phthalate.

10. The treatment regimen of claim 1, wherein the anionic polymer comprising phthalate functionality includes polyvinyl acetate phthalate.

11. The treatment regimen of claim 1, wherein the amorphous solid dispersion includes one or more functional components selected from the group consisting of antioxidants, wetting agents, and solubilizers.

12. The treatment regimen of claim 1, wherein the amorphous solid dispersion includes one or more solubilizers.

13. The treatment regimen of claim 12, wherein the one or more solubilizers comprises polyvinyl caprolactam-polyvinyl acetate-polyethylene glycol graft copolymer.

14. The treatment regimen of claim 12, wherein the one or more solubilizers comprises d-α-tocopherol acid polyethylene glycol (PEG) 1000 succinate.

15. The treatment regimen of claim 1, wherein the amorphous solid dispersion consists essentially of nilotinib and the anionic polymer comprising phthalate functionality.

16. The treatment regimen of claim 1, wherein the amorphous solid dispersion consists essentially of nilotinib and hydroxypropyl methylcellulose phthalate.

17. The treatment regimen of claim 1, wherein the amorphous solid dispersion consists essentially of nilotinib and polyvinyl acetate phthalate.

18. The treatment regimen of claim 1, wherein the nilotinib and the anionic polymer comprising phthalate functionality are present in the amorphous solid dispersion in a w/w ratio of 25:75 to 90:10 (nilotinib:polymer).

19. The treatment regimen of claim 1, wherein the pharmaceutical composition comprises the amorphous solid dispersion and one or more pharmaceutically acceptable additives.

20. The treatment regimen of claim 19, wherein the one or more pharmaceutically acceptable additives includes one or more solubilizers.

21. The treatment regimen of claim 20, wherein the one or more solubilizers comprises polyvinyl caprolactam-polyvinyl acetate-polyethylene glycol graft copolymer.

22. The treatment regimen of claim 20, wherein the one or more solubilizers comprises d-α-tocopherol acid polyethylene glycol (PEG) 1000 succinate.

* * * * *